(12) United States Patent
Jiang et al.

(10) Patent No.: US 11,359,025 B2
(45) Date of Patent: Jun. 14, 2022

(54) ANTI-IL1-RAP ANTIBODIES

(71) Applicant: Cantargia AB, Lund (SE)

(72) Inventors: Ying Ping Jiang, Lafayette, CA (US); Jagath R. Junutula, Fremont, CA (US); Leonard G. Presta, San Carlos, CA (US)

(73) Assignee: Cantargia AB, Lund (SE)

( * ) Notice: Subject to any disclaimer, the term of this patent is extended or adjusted under 35 U.S.C. 154(b) by 0 days.

(21) Appl. No.: 16/342,176

(22) PCT Filed: Oct. 16, 2017

(86) PCT No.: PCT/US2017/056808
§ 371 (c)(1),
(2) Date: Apr. 16, 2019

(87) PCT Pub. No.: WO2018/071910
PCT Pub. Date: Apr. 19, 2018

(65) Prior Publication Data
US 2019/0338038 A1 Nov. 7, 2019

Related U.S. Application Data

(60) Provisional application No. 62/425,970, filed on Nov. 23, 2016, provisional application No. 62/408,807, filed on Oct. 16, 2016.

(30) Foreign Application Priority Data

Oct. 10, 2017 (WO) ................ PCT/US2017/055994

(51) Int. Cl.
*C07K 16/28* (2006.01)
*G01N 33/68* (2006.01)
*A61K 47/68* (2017.01)

(52) U.S. Cl.
CPC ...... *C07K 16/2866* (2013.01); *A61K 47/6801* (2017.08); *A61K 47/6849* (2017.08); *G01N 33/6857* (2013.01); *C07K 2317/24* (2013.01); *C07K 2317/30* (2013.01); *C07K 2317/76* (2013.01)

(58) Field of Classification Search
None
See application file for complete search history.

(56) References Cited

U.S. PATENT DOCUMENTS

| 4,811,845 | A | 3/1989 | Baggett |
| 8,709,715 | B2 | 4/2014 | Karsunky |
| 8,715,619 | B2 | 5/2014 | Karsunky |
| 9,371,390 | B2 | 6/2016 | Karsunky |
| 9,403,906 | B2 | 8/2016 | Fioretos et al. |
| 9,458,237 | B2* | 10/2016 | Fioretos ................. A61P 35/02 |
| 9,796,783 | B2* | 10/2017 | Ågerstam et al. ...... A61P 37/06 |
| 10,005,841 | B2 | 6/2018 | Fioretos et al. |
| 10,005,842 | B2 | 6/2018 | Fioretos et al. |
| 10,100,119 | B2 | 10/2018 | Ågerstam et al. |
| 10,287,357 | B2 | 5/2019 | Ågerstam et al. |
| 10,562,971 | B2 | 2/2020 | Ågerstam et al. |
| 2002/0058247 | A1 | 5/2002 | Sallberg |
| 2003/0007976 | A1 | 1/2003 | Watson et al. |
| 2010/0272731 | A1 | 10/2010 | Presta et al. |
| 2015/0165063 | A1 | 6/2015 | Flygare et al. |
| 2015/0315279 | A1* | 11/2015 | Jiang ................. C07K 16/2866 424/1.49 |
| 2016/0271142 | A1 | 9/2016 | Junutula et al. |
| 2018/0293895 | A1 | 10/2018 | Fioretos et al. |
| 2018/0334506 | A1 | 11/2018 | Fioretos et al. |
| 2019/0202924 | A1 | 7/2019 | Gerstam et al. |

FOREIGN PATENT DOCUMENTS

| WO | 2010036959 | 4/2010 |
| WO | 2011021014 | 2/2011 |
| WO | 2014100772 A1 | 6/2014 |
| WO | 2015132602 | 9/2015 |
| WO | 2016020502 | 2/2016 |
| WO | 2018071455 | 4/2018 |
| WO | 2012098407 | 7/2020 |

OTHER PUBLICATIONS

Vajdos et al. (J Mol Biol. Jul. 5, 2002;320(2):415-28) (Year: 2002).*
Brown et al. (J Immunol. May 1996;156(9):3285-91) (Year: 1996).*
Notice of Recordation, recording assignment from Cellerant Therapeutics, Inc. to Cantargia AB for U.S. Pat. No. 8,709,715, recorded on Apr. 21, 2020 at Reel/Frame: 052454/0470.
Notice of Recordation, recording assignment from Cellerant Therapeutics, Inc. to Cantargia AB for U.S. Pat. No. 8,715,619, recorded on Apr. 21, 2020 at Reel/Frame: 052454/0472.
Notice of Recordation, recording assignment from Cellerant Therapeutics, Inc. to Cantargia AB for U.S. Pat. No. 9,371,390, recorded on Apr. 21, 2020 at Reel/Frame: 052454/0474.
Gregson et al., Linker Length Modulates DNA Cross-Linking Reactivity and Cytotoxic Potency of C8/C8¢ Ether-Linked C2-exo-Unsaturated Pyrrolo[2,1-c][1,4]benzodiazepine (PBD) Dimers, Journal of Medicinal Chemistry, Jan. 30, 2004, 47(5), 1161-1174.
Hartley, The development of pyrrolobenzodiazepines as antitumour agents, Expert Opinion on Investigational Drugs, Apr. 4, 2011, 20(6), 733-744.
Hopton et al., Nuclear Magnetic Resonance Solution Structures of Inter- and Intrastrand Adducts of DNA Cross-Linker SJG-136, Biochemistry, Apr. 13, 2011, 50(21), 4720-4732.
Rahman, et al., Effect of base sequence on the DNA cross-linking properties of pyrrolobenzodiazepine (PBD) dimers, Nucleic Acids Research, Mar. 21, 2011, 39(13), 5800-5812.
"UniProtKB—A0A0C9YH80", Retrived from Internet, URL: http://www.uniprot.org/uniprot/A0A0C9YH80, amino acids 7-13, Apr. 29, 2015.

(Continued)

*Primary Examiner* — Brian Gangle
*Assistant Examiner* — Andrea K McCollum
(74) *Attorney, Agent, or Firm* — McNeill Baur PLLC

(57) ABSTRACT

Provided herein are antibodies specific for Interleukin-1 receptor accessory protein (IL1-RAP).

17 Claims, 21 Drawing Sheets

Specification includes a Sequence Listing.

(56) References Cited

OTHER PUBLICATIONS

"UniProtKB—F8X0L8", Retrived from Internet, URL: http://www.uniprot.org/uniprot/F8X0L8, amino acids 134-143, Oct. 19, 2011.
"UniProtKB—K7U5TO", Retrived from Internet, URL: http://www.uniprot.org/uniprot/K7U5T0, amino acids 91-100, Feb. 6, 2013.
PCT/US2017/056808, "International Search Report and Written Opinion Received", Apr. 12, 2018, 11 pages.
Cipolla et al., Pyrrolo[2,1c][1,4]benzodiazepine as a Scaffold for the Design and Synthesis of Anti-Tumour Drugs, Anti-Cancer Agents in Medicinal Chemistry, Jan. 2009, 9(1), 1-31.
PCT/US2017/055994, "International Search Report and Written Opinion Received", Dec. 7, 2017, 20 pages.
Barreyro et al., "Overexpression of IL-1 receptor accessory protein in stem and progenitor cells and outcome correlation in AML and MDS," Blood 2012; 120(6): 1290-1298.
Dinarello, et al., "Interleukin-1 in the pathogenesis and treatment of inflammatory diseases", Blood, vol. 117, No. 14, Apr. 7, 2011.
Dinarello et al., "Treating inflammation by blocking interleukin-1 in a broad spectrum of diseases" Nature Reviews Drug Discovery, vol. 11(8), Aug. 2012, p. 633-652.
Jiang, Ping et al.: "Abstract 3337: Targeting acute myeloid leukemia via anti-IL1RAP antibodies", American Association for Cancer Research, vol. 76, No. 14 Suppl (2016).
Jiang, Ping et al.: "Abstract 662: Generation and characterization of antibodies specific for IL1RAP antigen to target quiescent and proliferating AML leukemic stem cells", American Association for Cancer Research, vol. 74, No. 19 Suppl (2014).
Uniprot accession No. Q9NPH3-I, as retrieved from the internet at https://www.uniprot.org/uniprot/Q9NPH3 (entered 2003).
Askmyr, M. et al: "Selective killing of candidate AML stem cells by antibody targeting of IL1RAP", Blood, pp. 3709-3713, May 2, 2013, vol. 121, No. 18.
Ågerstam, H. et al: "Antibodies targeting human IL1RAP (IL1R3) show therapeutic effects in xenograft models of acute myeloid leukemia", PNAS p. 10786-10791, Aug. 25, 2015, vol. 112, No. 34.

\* cited by examiner

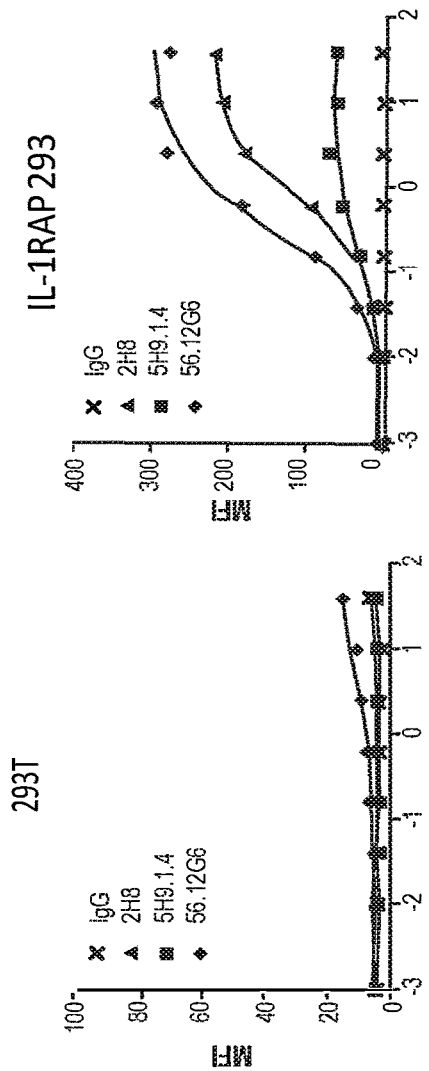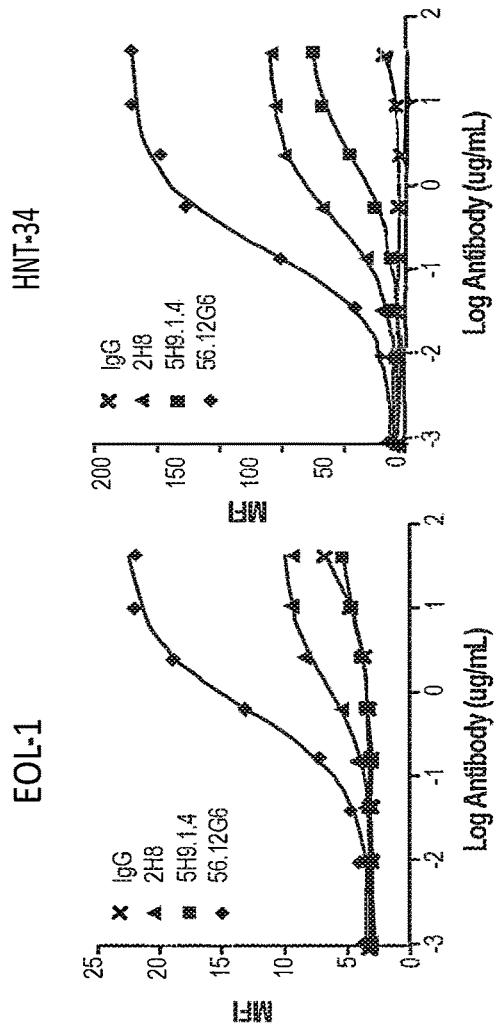
Figure 4A, Figure 4B, Figure 4C, Figure 4D

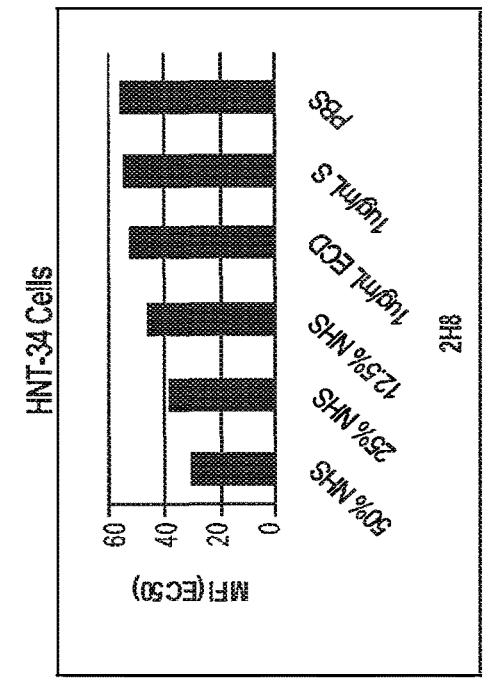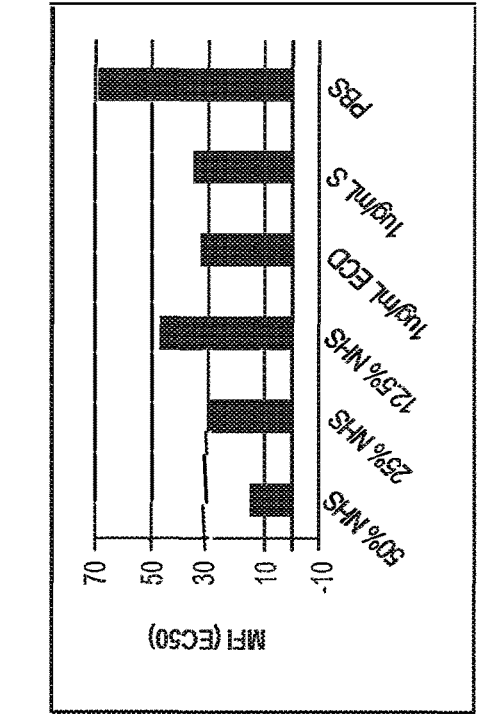
Figure 5B
Figure 5D
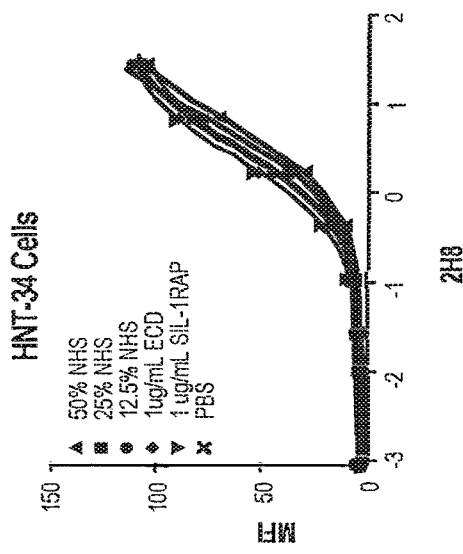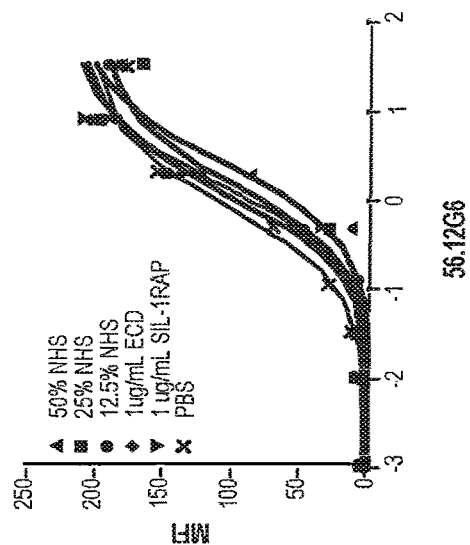
Figure 5A
Figure 5C

1) Clone 54.9D7

54.9D7HC
HVQLQQSGPELVRPGASVKLSCKASGYIFITYWMNWVKQRPGQGLEWVGQIFPASGTTYYNELFEGKATLTVDTS
SNTAYMHLTSLTSEDSAVYYCARTDFYRYDGGYALDYWGQGTSLTVSS 54.9D7LC
DIVLTQSPISLAVFLGQRATISCRASQSVSTSGYSSMHWYQQKAGQPPKLLIKYASDLESGVPVRFSGSGSGTDF
ILNIHPVEVEDIATYYCHHSWGIPMYTFGGGTKLEIKR

Figure 12A

2) Clone 56.12G6

56. 12G6 HC
RSNYSSLGAELVKPGASVTLSCEASGYTFTSYWIHWVKQRPGQGLEWIGEINPSHGHTTYNEKFKNKATLTVDKS
SSTAYMQVSSLTSEDSAVYYCTRHYGSYYFDLWGQGTTLTVSS 56.12G6 LC
QIVLTQSPAIMSAFPGEKVTMTCRASSSVSYMHWYRQKSGTFPKRWIYDTSKLASGVPARFSGSGSGTSYSLTIS
SMEAEDAATYYCQQWSTNPITFGAGTKLELK

Figure 12B

3) Clone 2H8

2H8HC
QIQLVQSGPELKKPGETVKISCKASGYTFTDYSMHWVKQAPGKGLKWMGWINTETGEPTYADDFKGRFAFSLETS
ASTAYLQINNLKNEDTATYFCARYYGYFDYWGQGTTLTVSS

2H8LC
DIVLTQSPASLAVSLGQRATISCRASESVDSYGNSFMHWYQQKPGQPPKLLIYRASNLESGIPARFSGSGSRTDF
TLTINPVEADDVATYYCQQSNEDPWTFGGGTKLEIK

Figure 12C

4) Clone 50.3G7

50.3G7HC

QIQLVQSGPELKKPGETVKISCKASGYTFTNYGMHWVKQSPGEGLKWMGWINTYTGEPTYADDFKGRFGFSLETS
ASSAYLQINDLKNEDMATYFCARYYGNFDYWGQGTTLTVSS 50.3G7LC

DIVLTQSPATLSVTPGDSVSLSCRASQSISNNLHWYQQKSHESPRLLIKYASQSISGIPSRFSGSGSGTDFTLSI
NSVETEDFGVYFCQQSHNWPHTFGGGTKLEIKR

Figure 12D

5) Clone 54.15B5

54.15B5HC

KWSWWSLGGGLAKPGGSLKLSCTASGFTFTSYVMSWVRQSPEKRLEWVAEISRGGSHTYYSDTVTGRFTISRDNA
NNALYLEMSSVRSADTAMYFCTRAYGNSEMDFWGQGTSVTVSS 54.15B5 LC

QIVLTQSPAIMSASPGEKVTMTCSASSSISYIHWYRQKPGTSPKRWIYDTSNLASGVPARFSGSGSGTSYSLTII
NMEAEDAATYYCHQRTYYPLTFGGGTRLELK

Figure 12E

6) Clone 42.1D3

42.1D3 HC

QIQLVQSGPELKKPGETVNISCKASGYTFTDFSMHWVKQAPGKGLQWMGWINTETGEPTYADDFEARFAFSLATS
ANTAYLKINNLKNEDTATYFCARFFLHFDYWGQGTTLTVSS 42.1D3 LC

DIVLTQSPATLSVTPGDSVSLSCRASQSINNDLHWYQQKSHESPRLLIKYASQSISGIPSRFSGSGSGTDFTLRI
NSVETEDFRMYFCQQSNNWPLTFGAGTKLEVK

Figure 12F

7) Clone 54.8H8

54.8H8 HC

EVQLVESGGGLVKPGGSLKLSCAASGFSFSSYGMSWVRQSPEKRLEWVAEITSGGSHTYYPDTVTGRFTISRDNA
KNTLYLEMSSLRSEDTAMYYCSRSYGNYVMDYWGQGTSVTVSS 54.8H8LC

QIVLTQSPAIMSASPGEKVTMTCSASSSVIYIYWFQQKPGSSPRLLIYDTSNLASGVPLRFSGSGSGTSYSLTIS
RMETEDVSTYYCQQWNSYPPTFGGGTKLEIK

Figure 12G

8) Clone 54.9E9

54.9E9 HC
QIQLVQSGPELKKPGETVKISCKASSYTFTDYSMHWVKQAPGKGLKWMGWINTETGEPRYADDFKGRFAFSLETS
ASTAYLQINNLKNEDTATYFCARFLLHFDYWGQGTILTVSS

54.9E9 LC
QIVLTQSPAIMSASPGEKVTMTCSASSSVSYMHWYQQKTGTSPKRLIYDTSKLASGVPARFSGSGSGTSYSLTIS
SMEAEDAATYYCHQRSYYPLTFGAGAKLELK

Figure 12H

9) Clone 50.6C12

50.6C12 HC
EVQLQQSGPELVKPGDSVKMSCKASGYTFTDYYMDWVKQSHGKSLEWIGYIYPHNGGTTYNQKFKGKATLTVDKS
SSTAYMELHSLTSEDSAVYYCARSPFNYKDPMDWWGQGTSVTVSS

50.6C12 LC
DIQMTQSPASLSASVGETVTITCRASGNIHNYLAWYQQKQGKSPHLLVYNAETLADGVPSRFSGSGSGTQYSLKI
NSLQPEDFGTYYCQHFWSTPWTFGGGTKLEIK

57.7A9HC
QVQLQQPGAELVKPGASVTLSCEASGYTFTSYWIHWVKQRPGQGLEWIGEINPSHGHTTYNEKFKNKATLTVDKS
SSTAYMQVSSLTSEDSAVYYCTRHYGSYYFDLWGQGTTLTVSS

57.7A9LC
QIVLTQSPAIMSAFPGEKVTMTCRASSSVSYMHWYRQKSGTFPKRWIYDTSKLASGVPARFSGSGSGTSYSLTIS
SMEAEDAATYYCQQWSTNPITFGAGTKLELK

46.8G1HC
QVQLQQSGPELVKPGASVKISCTASGYAFSTSWMNWVKQRPGKGLEWIGRIYPGDGDSNYNGKFKGKATLTADKS
SSTAYMQLSSLTSEDSAVYFCARRDYYGFFDVWGAGTTVTVSS

46.8G1LC
DIQMTQSPASLSVSVGETVTITCRASENIYSNLVWYQQKQGKSPQLLVYAATNLADGVPSRFSGSGSDTQYSLKI
NSLQSEDFGSYYCLHFWGPPYMYTFGGGTNLEMKR

42.3G6HC
QIQLVQSGPELKKPGETVKISCKASGYTFTDYSMHWVKQAPEKGLKWMGWINTETGEPTYADDFKGRFAFSLETS
ASTAYLQINNLKNEDTATYFCARGSFPWFTYWGQGTLVTVSA

42.3G6LC
DIVMTQAAFSNPVTLGTSASISCRSSKSLLHSNGITYLYWYLQKPGQSPQLLIYQMSNLASGVPDRFSSSGSGTD
FTLRISRVEAEDVGVYYCAQNLELPFTFGSGTKLEIK

Figure 12L

13) Clone 46.1D2

46.1D2HC
QVQLQQSGPELVKPGASVKISCKASGYGFSSSWMNWVKQRPGKGLEWIGRIYPGDGNTNYYGEFKGKATLTADKS
SSTAYMQLNSLTSEDSAVYFCARNDGYPAWFTYWGQGTLVTVSA

46.1D2LC
DIQMTQTTSSLSASLGDRVTISCSASQGISNYLNWYQQKPDGSVKLLIYYTSTLHSGVPSRFSGSGSGTDYSLTI
SNLEPEDIATYYCQQYSYLPWTFGGGTKLEIK

41.10C2 HC
QVTLKESGPGILQPSQTLSLTCSFSGFSLSTFGVGVGWIRQPSGKGLEWLAHIWWDDDKYYKSALKSRLTISKDT
SKNQVFLKIANVDTADTATYFCARLKLGPYYFDYWGQGTTLTVSS

41.10C2 LC
DSVLTQSLTSLVVSLGQRATISCRASESVDNHGNSFMHWYQQKPGQPPKLLIFLASNLESGIPARFSGSGSRTDF
TLTINPVEGDEGATYYCHQINAHPYTFGGGTKLEIKR

46.2C2HC
DVKLVESGGGLVKLGGSLKLSCAASGFTFSSYYMSWVRQTPEKRLEWVATISNSGGSTYYADSVKDRFTISRDSA
KNTLYLQMNSLISEDTAVYYCALYYGNFGFDYWGQGTSLTVSS

46.2C2LC
QIVLTQSPAIMSASPGEKVTMTCSARSSVDYMYWYQQKPGSSPRLLIYATSNLASGVPVRFSGSGSGTSYSLTIV
RVEAEDAATYYCQQWNTYPLTFGAGTKLELK

Figure 12O

16) 44.5D2
44.5D2HC
TVVDSGKCRSKGFGYTLGGCGVLWSKQRPGQGLEWIGEINPSNGFTNYNEKFNYKATLTVDKSSSTAYMQLSSLT
SADSAVYYCTTGGHYFDYWGQGTTLTVSS 44.5D2LC
DIVMTQSHKFMSTSVGDRVSITCKASQDVGTAVAWYQQKSGQSPKLLIYWASTRHTEVPDRFTGSGSGTDFTLTI
SNVQSEDLTDYFCQQYSSYPLYTFGGGTKLEIKR

Figure 12P

ANTI-IL1-RAP ANTIBODIES

REFERENCE TO RELATED APPLICATIONS

This application claims the benefit of the filing dates of U.S. Provisional application 62/408,807, filed Oct. 16, 2016, U.S. Provisional application 62/425,970, filed Nov. 23, 2016, and International Application PCT/US2017/055994, filed Oct. 10, 2017, all of which are incorporated by reference in their entirety.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on Apr. 16, 2021, is named 2021-04-16_01177-0007-00US_Seq_List_ST25.txt and is 82,384 bytes in size.

BACKGROUND OF THE INVENTION

Interleukin-1 (IL1) is a central regulator of both acute and chronic inflammatory responses mediated by the immune system. Interleukin-1 receptor accessory protein (IL1-RAP, aka IL-1R3) is a co-receptor for IL1 that functions in the IL1 receptor signal transduction complex and in some contexts is necessary to link cell membrane events to downstream signaling pathways. IL-1 induces synthesis of acute phase and proinflammatory proteins during infection, tissue damage and stress, playing an important role in mammalian immunity.

IL1-RAP is also expressed on cancer cells and cancer stem cells ("CSCs"), which are cells that can give rise to additional cancer cells. In particular, IL1-RAP is highly expressed in CSCs that are prevalent in acute myeloid leukemia (AML) and myelodysplastic syndromes (MDSs) with poor prognosis. As a result, IL1-RAP has been a proposed as a promising target. Barreyro et al., *Blood* 2012; 120(6): 1290-1298.

One of the major limitations of chemotherapy is the general inability of anticancer drugs to discriminate between normal and cancer cells. Almost all members of the major categories of antineoplastic agents have considerable toxicity for normal cells.

Compositions that specifically target cancer cells can avoid this problem. However, existing cancer treatments do not target CSCs. For this reason, existing chemotherapeutic strategies, even when specifically delivered to cancer cells, do not effectively eliminate the cancer. Risk of recurrence remains because the surviving CSCs can give rise to new cancer cells.

By differentially targeting disease tissue, antibodies present considerable therapeutic opportunity to improve the targeted discrimination between diseased and non-diseased tissue.

US2015/0315279 refers to anti-ILRAP antibodies that bind an extracellular membrane-anchor-proximal region of human IL1RAP.

SUMMARY OF THE INVENTION

In one aspect provided herein is an isolated anti-IL1-RAP antibody comprising a variable light chain and a variable heavy chain, wherein: a) the variable light chain comprises a sequence with at least 90% sequence identity to a murine antibody light chain sequence selected from the group consisting of: 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2, 44.5D2; and/or b) the variable heavy chain comprises a sequence with at least 90% sequence identity to a murine antibody heavy chain sequence selected from the group consisting of: 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2, 44.5D2. In one embodiment the antibody binds receptor IL1-RAP with greater affinity than it binds soluble IL1-RAP (e.g., at least any of 2 times, 5 times, 10 times or 100 times greater affinity). In another embodiment the sequence identity is at least 95%, 96%, 97%, 98% or 99%.

In another aspect provided herein is an anti-IL-RAP antibody comprising a variable light chain and a variable heavy chain, wherein: a) the variable light chain comprises a sequence having a CDRL1, CDRL2 and CDRL3 having at least 95% sequence identity to a murine antibody light chain CDRL1, CDRL2 and CDRL3 sequence of an antibody selected from the group consisting of: 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2, 44.5D2; and/or b) the variable heavy chain comprises a sequence having a CDRH1, CDRH2, CDRH3 having at least 95% sequence identity to a murine antibody heavy chain CDRH1, CDRH2, CDRH3 sequence of an antibody selected from the group consisting of: 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2, 44.5D2, wherein the antibody binds receptor IL1-RAP with greater affinity than it binds soluble IL1-RAP (e.g., at least any of 2 times, 5 times, 10 times or 100 times greater affinity). In one embodiment the CDRL1, CDRL2, CDRL3, CDRH1, CDRH2 and CDRH3 have sequences from an antibody selected from:

| Clone ID | HC | | | LC | | | SEQ ID NOS: |
|---|---|---|---|---|---|---|---|
| | CDRH1 | CDRH2 | CDRH3 | CDRL1 | CDRL2 | CDRLC3 | |
| 54.9D7 | GYIFITY | FPASGT | TDFYRYDGGYAL | RASQSVSTSGYSSMH | YASDLES | HHSWGIPMYT | 7-12 |
| 56.12G6 | GYTFTSY | NPSHGH | HYGSYYFDL | RASSSVSYMH | DTSKLAS | QQWSTNPIT | 15-20 |
| 2H8 | GYTFTDYSMH | NTETGE | YYGYFDY | RASESVDSYGNSFMHW | RASNLES | QQSNEDPWT | 21-26 |
| 50.3G7 | GYTFTNY | NTYTGE | YYGNFDY | RASQSISNNLH | YASQSIS | QQSHNWPHT | 29-34 |
| 54.15B5 | GFTFTSY | SRGGSH | AYGNSEMDF | SASSSISYIH | DTSNLAS | HQRTYYPLT | 35-40 |

| Clone ID | HC CDRH1 | CDRH2 | CDRH3 | LC CDRL1 | CDRL2 | CDRLC3 | SEQ ID NOS: |
|---|---|---|---|---|---|---|---|
| 42.1D3 | GYTFTDF | NTETGE | FFLHFDY | RASQSINNDLH | YASQSIS | QQSNNWPLT | 43, 22, 44, 45, 33, 46 |
| 54.8H8 | GFSFSSYG | TSGGSH | SYGNYVMDY | SASSSVIYIY | DTSNLAS | QQWNSYPPT | 47-50, 39, 51 |
| 549E 9 | SYTFTDY | NTETGE | FLLHFDY | SASSSVSYMH | DTSKLAS | HQRSYYPLT | 54, 22, 55, 56, 19, 57 |
| 50.6C12 | GYTFTDY | YPHNGG | SPFNYKDPMDW | RASGNIHNYLA | NAETLAD | QHFWSTPWT | 60-65 |
| 57.7A9 | GYTFTSY | NPSHGH | HYGSYYFDL | RASSSVSYMH | DTSKLAS | QQWSTNPIT | 15-20 |
| 46.8G1 | GYAFSTS | YPGDGD | RDYYGFFDV | RASENIYSNLV | AATNLAD | LHFWGPPYMYT | 69-74 |
| 42.3G6 | GYTFTDY | NTETGE | GSFPWFTY | RSSKSLLHSNGITYLY | QMSNLAS | AQNLELPFT | 60, 22, 77-80 |
| 46.1D2 | GYGFSSS | YPGDGN | NDGYPAWFTY | SASQGISNYLN | YTSTLHS | QQYSYLPWT | 83-88 |
| 41.10C2 | GFSLSTFGV | WWDDD | LKLGPYYFDY | RASESVDNHGNSFMH | LASNLES | HQINaHPYT | 91-96 |
| 46.2C2 | GFTFSSY | SNSGGS | YYGNFGFDY | SARSSVDYMY | ATSNLAS | QQWNTYPLT | 99-104 |
| 44.5D2 | GYTLGGC | NPSNGF | GGHYFDY | KASQDVGTAVA | WASTRHT | QQYSSYPLYT | 107-112 |

In another aspect, provided is an (optionally isolated) anti-IL1-RAP antibody comprising: (1) a light chain variable region comprising a CDR L1, a CDR L2, and a CDR L3 and (2) a heavy chain variable region comprising a CDR H1, a CDR H2, and a CDR H3, wherein the CDR L1 has a sequence having at least 90% sequence identity (e.g., having zero, one or two conservative or nonconservative amino acid substitution compared to) the sequence of RASQSVSTSGYSSMH (SEQ ID NO: 10), the CDR L2 has a sequence having at least 90% sequence identity (e.g., having zero, one or two conservative or nonconservative amino acid substitution compared to) the sequence of YASDLES (SEQ ID NO: 11), the CDR L3 has a sequence having at least 90% sequence identity to (e.g., having zero, one or two conservative or nonconservative amino acid substitution compared to) the sequence of HHSWGIPMYT (SEQ ID NO: 12), the CDR H1 a sequence having at least 90% sequence identity to (e.g., having zero, one or two conservative or nonconservative amino acid substitution compared to) the sequence of GYIFITY (SEQ ID NO: 7), the CDR H2 a sequence having at least 90% sequence identity to (e.g., having zero, one or two conservative or nonconservative amino acid substitution compared to) the sequence of FPASGT (SEQ ID NO: 8), and the CDR H3 has a sequence having at least 90% sequence identity to (e.g., having zero, one or two conservative or nonconservative amino acid substitution compared to) the sequence of TDFYRYDGGYALDY (SEQ ID NO: 9).

In some embodiments of this aspect, the CDR L1 of the isolated antibody has the sequence of RASQSVST-SGYSSMH (SEQ ID NO: 10), the CDR L2 of the isolated antibody has the sequence of YASDLES (SEQ ID NO: 11), the CDR L3 of the isolated antibody has the sequence of HHSWGIPMYT (SEQ ID NO: 12), the CDR H1 of the isolated antibody the sequence of GYIFITY (SEQ ID NO: 7), the CDR H2 of the isolated antibody the sequence of FPASGT (SEQ ID NO: 8), and the CDR H3 of the isolated antibody has the sequence of TDFYRYDGGYALDY (SEQ ID NO: 9).

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 5)
DIVLTQSPISLAVFLGQRATISCRASQSVSTSGYSSMHWYQQKAGQPPKL

LIKYASDLESGVPVRFSGSGSGTDFILNIHPVEVEDIATYYCHHSWGIPM

YTFGGGTKLEIKR.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 115)
DIQMTQSPSSLSASVGDRVTITCRASQSVSTSGYSSMHWYQQKPGKAPKL

LIYYASDLESGVPSRFSGSGSGTDFTLTISSLQPEDFATYYCHHSWGIPM

YTFGQGTKLEIKR.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 116)
DIQLTQSPSSLSASVGDRATITCRASQSVSTSGYSSMHWYQQKPGKAPKL

LIYYASDLESGVPSRFSGSGSGTDFTLTISSVQPEDFATYYCHHSWGIPM

YTFGQGTKLEIKR.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 117)
DIQLTQSPSSLSASVGDRATITCRASQSVSTSGYSSMHWYQQKPGKAPKL

LIKYASDLESGVPSRFSGSGSGTDFTLTISSVQPEDFATYYCHHSWGIPM

YTFGQGTKLEIKR.

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 6)
HVQLQQSGPELVRPGASVKLSCKASGYIFITYWMNWVKQRPGQGLEWVGQ

IFPASGTTYYNELFEGKATLTVDTSSNTAYMHLTSLTSEDSAVYYCARTD

FYRYDGGYALDYWGQGTSLTVSS.

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 118)
QVQLVQSGAEVKKPGASVKVSCKASGYIFITYWMNWVRQAPGQGLEWMGQ

IFPASGTTYYAQKFQGRVTMTRDTSTSTVYMELSSLRSEDTAVYYCARTD

FYRYDGGYALDYWGQGTLVTVSS.

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 119)
QVQLVQSGAEVKKPGASVKVSCKASGYIFITYWMNWVRQAPGQGLEWVGQ

IFPASGTTYYAQKFQGRVTMTVDTSTSTVYMELSSLRSEDTAVYYCARTD

FYRYDGGYALDYWGQGTLVTVSS.

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 120)
QVQLVQSGAEVKKPGASVKLSCKASGYIFITYWMNWVRQAPGQGLEWVGQ

IFPASGTTYYAQKFQGRATLTVDTSTSTAYMELSSLRSEDTAVYYCARTD

FYRYDGGYALDYWGQGTLLTVSS.

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of (SEQ ID NO: 121)
EVQLVQSGAEVKKPGASVKVSCKASGYIFITYWMNWVRQAPGQGLEWVGQ

IFPASGTTYYAQKFQGRVTMTVDTSTSTVYMELSSLRSEDTAVYYCARTD

FYRYEGGYALDYWGQGTLVTVSS.

In another aspect, provided is an (optionally isolated) anti-IL1-RAP antibody comprising a light chain variable region and a heavy chain variable region, wherein the light chain variable region has a sequence having at least 90% (e.g., at least 91%, 92%, 93%, 94%, 95%, 96%, 97%, 98%, or 99% or 100%) sequence identity to the sequence of any one of SEQ ID NOs: 5 and 115-117, and the heavy chain variable region has a sequence having at least 90% (e.g., at least 91%, 92%, 93%, 94%, 95%, 96%, 97%, 98%, or 99% or 100%) sequence identity to the sequence of any one of SEQ ID NOs: 6 and 118-121.

In some embodiments of this aspect, the light chain variable region of the isolated antibody has a sequence of any one of SEQ ID NOs: 5 and 115-117, and the heavy chain variable region of the isolated antibody has a sequence of any one of SEQ ID NOs: 6 and 118-121.

In some embodiments of this aspect, the light chain variable region of the isolated antibody has a sequence having at least 90% sequence identity to the sequence of SEQ ID NO: 5, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 6. In some embodiments, the light chain variable region of the isolated antibody has a sequence of SEQ ID NO: 5, and the heavy chain variable region of the isolated antibody has a sequence of SEQ ID NO: 6.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 117, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 118. In some embodiments, the light chain variable region of the isolated antibody has a sequence of SEQ ID NO: 117, and the heavy chain variable region of the isolated antibody has a sequence of SEQ ID NO: 118.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 117, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 119. In some embodiments, the light chain variable region of the isolated antibody has a sequence of SEQ ID NO: 117, and the heavy chain variable region of the isolated antibody has a sequence of SEQ ID NO: 119.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 117, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 120. In some embodiments, the light chain variable region of the isolated antibody has a sequence of SEQ ID NO: 117, and the heavy chain variable region of the isolated antibody has a sequence of SEQ ID NO: 120.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 117, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 121. In some embodiments, the light chain variable region of the isolated antibody has a sequence of SEQ ID NO: 117, and the heavy chain variable region of the isolated antibody has a sequence of SEQ ID NO: 121.

In another aspect, the invention features an isolated anti-IL1-RAP antibody comprising: (1) a light chain variable region comprising a CDR L1, a CDR L2, and a CDR L3 and (2) a heavy chain variable region comprising a CDR H1, a CDR H2, and a CDR H3, wherein the CDR L1 has a sequence having at least 90% sequence identity (e.g., having zero, one or two conservative or nonconservative amino acid substitution compared to) to the sequence of RASQSISNNLH (SEQ ID NO: 32), the CDR L2 has a sequence having at least 90% sequence identity (e.g., having zero, one or two conservative or nonconservative amino acid substitution compared to) to the sequence of YASQSIS (SEQ ID NO: 33), the CDR L3 has a sequence having at least 90% sequence identity (e.g., having zero, one or two conservative or nonconservative amino acid substitution compared to) the sequence of QQSHNWPHT (SEQ ID NO: 34), the CDR H1 a sequence having at least 90% sequence identity (e.g., having zero, one or two conservative or nonconservative amino acid substitution compared to) the sequence of GYTFTNY (SEQ ID NO: 29), the CDR H2 a sequence having at least 90% sequence identity (e.g., having zero, one or two conservative or nonconservative amino acid substitution compared to) to the sequence of NTYTGE (SEQ ID NO: 30), and the CDR H3 has a sequence having at least 90% sequence identity (e.g., having zero, one or two conservative or nonconservative amino acid substitution compared to) to the sequence of YYGNFDY (SEQ ID NO: 31).

In some embodiments of this aspect, the CDR L1 of the isolated antibody has the sequence of RASQSISNNLH (SEQ ID NO: 32), the CDR L2 of the isolated antibody has the sequence of YASQSIS (SEQ ID NO: 33), the CDR L3 of the isolated antibody has the sequence of QQSHNWPHT (SEQ ID NO: 34), the CDR H1 of the isolated antibody the sequence of GYTFTNY (SEQ ID NO: 29), the CDR H2 of the isolated antibody the sequence of NTYTGE (SEQ ID NO: 30), and the CDR H3 of the isolated antibody has the sequence of YYGNFDY (SEQ ID NO: 31).

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of

```
                                        (SEQ ID NO: 27)
DIVLTQSPATLSVTPGDSVSLSCRASQSISNNLHWYQQKSHESPRLLIKY

ASQSISGIPSRFSGSGSGTDFTLSINSVETEDFGVYFCQQSHNWPHTFGG

GTKLEIKR.
```

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of

```
                                       (SEQ ID NO: 122)
EIVMTQSPATLSVSPGERATLSCRASQSISNNLHWYQQKPGQAPRLLIYY

ASQSISGIPARFSGSGSGTEFTLTISSLQSEDFAVYYCQQSHNWPHTFGQ

GTKLEIKR.
```

In some embodiments of this aspect, the heavy chain variable region of the isolated antibody has a sequence having at least 90% sequence identity to the sequence of

```
                                        (SEQ ID NO: 28)
HVQLQQSGPELVRPGASVKLSCKASGYIFITYWMNWVKQRPGQGLEWVGQ

IFPASGTTYYNELFEGKATLTVDTSSNTAYMHLTSLTSEDSAVYYCARTD

FYRYDGGYALDYWGQGTSLTVSS.
```

In some embodiments of this aspect, the heavy chain variable region of the isolated antibody has a sequence having at least 90% (e.g., at least 91%, 92%, 93%, 94%, 95%, 96%, 97%, 98%, or 99% or 100%) sequence identity to the sequence of

```
                                       (SEQ ID NO: 123)
EVQLVQSGAEVKKPGASVKISCKASGYTFTNYGMHWVRQAPGQGLEWMGW

INTYTGEPTYAQKFQGRFTFTLDTSTSTAYLEIRSLRSDDTAVYYCARYY

GNFDYWGQGTLLTVSS.
```

In another aspect, the invention features an isolated anti-IL1-RAP antibody comprising a light chain variable region and a heavy chain variable region, wherein the light chain variable region has a sequence having at least 90% (e.g., at least 91%, 92%, 93%, 94%, 95%, 96%, 97%, 98%, or 99% or 100%) sequence identity to the sequence of any one of SEQ ID NOs: 27 and 122, and the heavy chain variable region has a sequence having at least 90% (e.g., at least 91%, 92%, 93%, 94%, 95%, 96%, 97%, 98%, or 99% or 100%) sequence identity to the sequence of any one of SEQ ID NOs: 28 and 123.

In some embodiments of this aspect, the light chain variable region of the isolated antibody has a sequence of any one of SEQ ID NOs: 27 and 122, and the heavy chain variable region of the isolated antibody has a sequence of any one of SEQ ID NOs: 28 and 123.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 27, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 28. In some embodiments, the light chain variable region of the isolated antibody has a sequence of SEQ ID NO: 27, and the heavy chain variable region of the isolated antibody has a sequence of SEQ ID NO: 28.

In some embodiments of this aspect, the light chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 122, and the heavy chain variable region of the isolated antibody has a sequence having at least 90% (e.g., at least 91%, 92%, 93%, 94%, 95%, 96%, 97%, 98%, or 99% or 100%) sequence identity to the sequence of SEQ ID NO: 123. In some embodiments, the light chain variable region of the isolated antibody has a sequence of SEQ ID NO: 122, and the heavy chain variable region of the isolated antibody has a sequence of SEQ ID NO: 123.

In another embodiment the (optionally isolated) antibody is monospecific. In another embodiment the (optionally isolated) antibody is multispecific or bispecific. In another embodiment the multispecific or bispecific (optionally isolated) antibody binds to an antigen selected from the group consisting of: CD45, CD38 and CD34. In another embodiment the (optionally isolated) antibody is humanized. In another embodiment the (optionally isolated) antibody is a whole immunoglobulin. In another embodiment the (optionally isolated) antibody is an antibody fragment, e.g., selected from the group consisting of: Fab, F(ab')2, Fab' or single chain Fv.

In another aspect provided herein is a nucleic acid molecule comprising a nucleotide sequence encoding any of the anti-IL1-RAP antibodies or antibody fragments as described herein. In one embodiment the nucleic acid sequence is operably linked to an expression control sequence. In another embodiment the nucleic acid molecule is comprised in an expression vector.

In another aspect provided herein is a host cell comprising an expression vector as disclosed herein. In one embodiment the host cell is a Chinese Hamster Ovary (CHO) cell.

In another aspect provided herein is a process for creating an anti-IL1-RAP antibody comprising culturing a host cell as provided herein. In one embodiment the process further comprises isolating the antibody.

In another aspect provided herein is an antibody as disclosed herein that is conjugated to a chemical moiety. In one embodiment the conjugated moiety is a label. In another embodiment the conjugated moiety is chemotherapeutic or cytotoxic agent. In another embodiment the chemotherapeutic or cytotoxic agent is selected from the group consisting of: alkylating agent, anti-metabolite, antibiotic, hydroxyurea, platinum-based chemotherapeutic agent, taxane, bortezomib, lenalidomine, thalidomide, metanzinoid.

In another aspect provided herein is a composition comprising and aduvant and an antibody or a conjugated antibody as provided herein. In one embodiment the composition is pharmaceutically acceptable.

In another aspect provided herein is a method of detecting a cell expressing receptor IL1-RAP comprising: contacting a cell with an effective amount of an antibody, antibody fragment or antibody conjugate as disclosed herein that is capable of binding the cell, and detecting binding of the antibody to the cell, wherein binding indicates the presence of the cell of interest.

In another aspect provided herein is a method of diagnosing a disease comprising: contacting a biological sample from an individual with an effective amount an antibody, antibody fragment or antibody conjugate as disclosed herein that is capable of binding to diseased cells, and detecting binding of the antibody to a diseased cell, wherein binding indicated the presence of the disease. In one embodiment the antibody is conjugated to a detectable moiety. In another embodiment the disease is cancer. In another embodiment the cell is a tumor cell or a cancer stem cell. In another embodiment the disease is a myeloproliferative disorder. In another embodiment the myeloproliferative disorder is selected from the group consisting of; AML, CML, CMML, multiple myeloma, plasmacytoma and myelofibrosis.

In another aspect provided herein is a method of inhibiting cell division comprising contacting a cell with at least an effective amount of an antibody, antibody fragment or antibody conjugate as disclosed herein that is capable of binding the cell. In one embodiment the inhibition of cell division results in cell death. In another embodiment the cell is a tumor or cancer stem cell. In another embodiment the tumor or cancer stem cells are from a myeloproliferative disorder. In another embodiment the myeloproliferative disorder is selected from the group consisting of: AML, CML, CMML, multiple myeloma, plasmacytoma and myelofibrosis.

In another aspect provided herein is a method of inhibiting NF-kB signaling comprising contacting a cell with at least an effective amount of an antibody or antibody fragment as disclosed herein that is capable of binding the cell. In one embodiment the inhibition of cell division results in cell death. In another embodiment the cell is a tumor or cancer stem cell. In another embodiment the tumor or cancer stem cells are from a myeloproliferative disorder. In another embodiment the myeloproliferative disorder is selected from the group consisting of: AML, CML, CMML, multiple myeloma, plasmacytoma and myelofibrosis.

In another aspect provided herein is a method of treating cancer comprising administering to a patient a therapeutically effective amount of an antibody or antibody conjugate as disclosed herein. In one embodiment the antibody is an antibody conjugate which is conjugated with a chemotherapeutic or cytotoxic drug via a cleavable, non-cleavable or traceless linker. In another embodiment the drug is selected from the group consisting of: maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof. In another embodiment the cancer is a myeloproliferative disorder. In another embodiment the myeloproliferative disorder is selected from the group consisting of: AML, CML, CMML, multiple myeloma, pasmocytoma and myelofibrosis. In another embodiment the antibody described herein binds to a tumor associated antigen or cancer stem cell antigen. In some embodiments, the tumor associated antigen or cancer stem cell antigen is CLL-1.

In another aspect provided herein is a method of reducing tumor burden comprising administering an effective amount of an antibody, antibody fragment or antibody conjugate as disclosed herein.

BRIEF DESCRIPTION OF THE DRAWINGS

FIGS. 4A-4D show plots of binding specificity of clones 2H8, 5H9.1.4 and 56.12G6, which were tested against various cell lines (i.e., 293T, IL1-RAP transfected 293, EOL-1, HNT-34) by FACS.

FIGS. 5A-5D are FACS plots and histograms showing the binding of anti-IL1-RAP antibodies 2H8 and 56.12G6 to HNT-34 cells in the presence of various levels of normal human serum (NHS) isolated from healthy patients and soluble IL1-RAP (Q9NPH3-2) or extracellular domain (ECD) of IL1-RAP (Q9NPH3-4). Left: Antibody binding titration on HNT-34 cells. Right: EC50 values for treatment conditions.

FIGS. 12A-12P show the light and heavy chain variable region sequences of the 54.9D7 (SEQ ID NOS:5 and 28), 56.12G6 (SEQ ID NOS:13 and 14), 2H8 (SEQ ID NOS:126 and 127), 50.3G7 (SEQ ID NOS:27 and 134), 54.15B5 (SEQ ID NOS:128 and 129), 42.1D3 (SEQ ID NOS:41 and 42), 54.8H8 (SEQ ID NOS:130 and 131), 54.9E9 (SEQ ID NOS:52 and 53), 50.6C12 (SEQ ID NOS:58 and 59), 57.7A9 (SEQ ID NOS:13 and 66), 46.8G1 (SEQ ID NO:67 and 68), 42.3G6 (SEQ ID NOS:75 and 76), 46.1D2 (SEQ ID NOS:81 and 82), 41.10C2 (SEQ ID NOS:89 and 90), 46.2C2 (SEQ ID NOS:97 and 98), 44.5D2 (SEQ ID NOS: 105 and 106), respectively. The CDRs are bolded and underlined.

DETAILED DESCRIPTION OF THE INVENTION

I. Introduction

Figure 1:
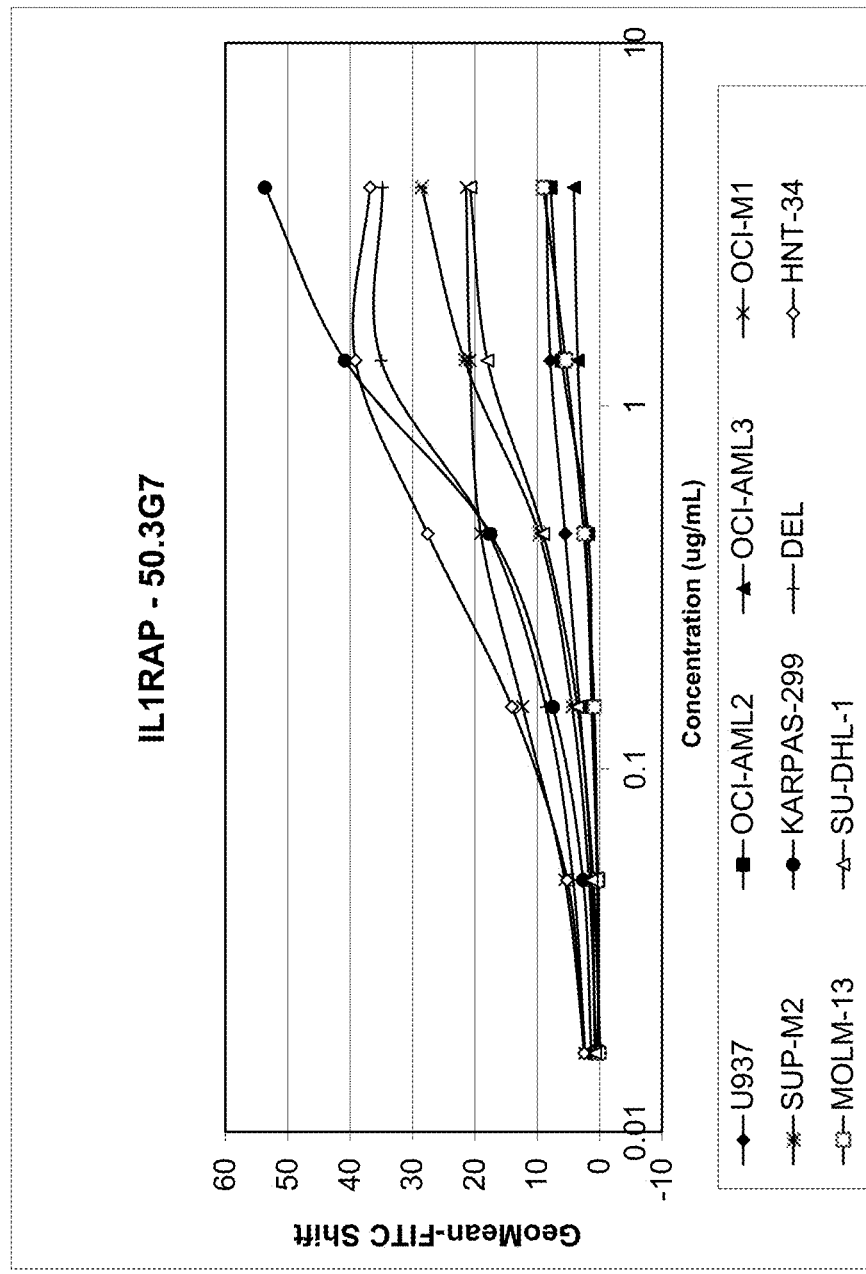
FIG. 1 is a FACS plot of the binding of anti-IL1-RAP antibody 50.3G7 to IL1-RAP, as shown by increased fluorescence, in various AML cell lines.

Provided herein are antibodies that specifically bind to IL1-RAP. Anti-IL1-RAP antibodies can be used in conjugated form to deliver a cytotoxic agent specifically to IL1-RAP-expressing cells, for example, cancer cells such as cancer stem cells (CSC), leukemias, lymphomas, and solid tumors.

Also provided are anti-IL1-RAP specific antibodies that inhibit cancer cell growth and/or reduce tumor burden in the absence conjugation to a cytoxic agent. Such antibodies can inhibit signaling mediated by interleukin 1 family members 5, 6, 8 or 9 (IL-1F5, IL-1F6, IL1F8 or IL1F9), induce antibody dependent cell-mediated cytotoxicity, block IL-1 dependent signaling, or a combination thereof. In some embodiments, the antibodies of the disclosure provide complement dependent cytotoxicity (CDC) or antibody-dependent cell-mediated cytotoxicity (ADDC)

Also provided are anti-IL1-RAP specific antiobdies that are effective for reducing cancer growth or cancer stem cell growth, metabolic activity, viability or division. In addition to, or in combination with the therapeutic applications, anti-IL1-RAP antibodies of the disclosure are useful for in vivo and in vitro diagnostic agents.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein "IL1-RAP" refers to human interleukin 1 receptor accessory protein. A sequence of IL1-RAP can be as shown in Uniprot accession number Q9NPH3-1 (isoform 1):

```
                                          (SEQ ID NO: 1)
         10         20         30         40
    MTLLWCVVSL YFYGILQSDA SERCDDWGLD TMRQIQVFED 50         60         70         80
    EPARIKCPLF EHFLKFNYST AHSAGLTLIW YWTRQDRDLE 90        100        110        120
    EPINFRLPEN RISKEKDVLW FRPTLLNDTG NYTCMLRNTT 130        140        150        160
    YCSKVAFPLE VVQKDSCFNS PMKLPVHKLY IEYGIQRITC 170        180        190        200
    PNVDGYFPSS VKPTITWYMG CYKIQNFNNV IPEGMNLSFL 210        220        230        240
    IALISNNGNY TCVVTYPENG RTFHLTRTLT VKVVGSPKNA 250        260        270        280
    VPPVIHSPND HVVYEKEPGE ELLIPCTVYF SFLMDSRNEV 290        300        310        320
    WWTIDGKKPD DITIDVTINE SISHSRTEDE TRTQILSIKK 330        340        350        360
    VTSEDLKRSY VCHARSAKGE VAKAAKVKQK VPAPRYTVEL 370        380        390        400
    ACGFGATVLL VVILIVVYHV YWLEMVLFYR AHFGTDETIL 410        420        430        440
    DGKEYDIYVS YARNAEEEEF VLLTLRGVLE NEFGYKLCIF 450        460        470        480
    DRDSLPGGIV TDETLSFIQK SRRLLVVLSP NYVLQGTQAL 490        500        510        520
    LELKAGLENM ASRGNINVIL VQYKAVKETK VKELKRAKTV 530        540        550        560
    LTVIKWKGEK SKYPQGRFWK QLQVAMPVKK SPRRSSSDEQ

570
    GLSYSSLKNV
```

In the 570 aa polypeptide shown above, residues 1-20 is the signal sequence, residues 21-367 are extracellular, residues 368-388 are transmembrane, while residue 389-570 are cytoplasmic. One of skill will understand that IL1-RAP variants (e.g., species homologs, allelic variants, etc.) can be optimally aligned, e.g., for identification of conserved residues and domains.

As used herein, "membrane-anchor proximal region" refers to amino acids of the IL1-RAP protein that are proximal to, but N-terminal of the transmembrane region. In some cases, receptor IL1-RAP includes a membrane-anchor proximal region. One of skill in the art will know how to determine membrane-anchor proximal regions which can include, by way of example only, amino acids 300-370, 301-370, 302-370, 303-370, 304-370, 305-370, 306-370, 307-370, 308-370, 309-370, 310-370, 311-370, 312-370, 313-370, 314-370, 315-370, 316-370, 317-370, 318-370, 319-370, 320-370, 321-370, 322-370, 323-370, 324-370, 325-370, 326-370, 327-370, 328-370, 329-370, 330-370, 331-370, 332-370, 333-370, 334-370, 335-370, 336-370, 337-370, 338-370, 339-370, 340-370, 340-369, 340-368, 340-367, 340-366, 340-365, 340-364, 340-363, 340-362, 340-361, 340-360, 341-370, 341-369, 341-368, 341-367, 341-366, 341-365, 341-364, 341-363, 341-362, 341-361, 341-360, 342-370, 342-369, 342-368, 342-367, 342-366, 342-365, 342-364, 342-363, 342-362, 342-361, 342-360, 343-370, 343-369, 343-368, 343-367, 343-366, 343-365, 343-364, 343-363, 343-362, 343-361, 343-360, 344-370, 344-369, 344-368, 344-367, 344-366, 344-365, 344-364, 344-363, 344-362, 344-361, 344-360, 345-370, 345-369, 345-368, 345-367, 345-366, 345-365, 345-364, 345-363, 345-362, 345-361, 345-360, 346-370, 346-369, 346-368, 346-367, 346-366, 346-365, 346-364, 346-363, 346-362, 346-361, 346-360, 347-370, 347-369, 347-368, 347-367, 347-366, 347-365, 347-364, 347-363, 347-362, 347-361, or amino acids 347-360 of Uniprot accession Q9NPH3-1. The membrane-anchor proximal region may include regions of the IL1-RAP primary sequence that are 15, 14, 13, 12, 11, 10 or fewer amino acids in the carboxy or amino direction from the above-mentioned residues. In some cases, anti-IL1-RAP antibodies provided herein bind to IL1-RAP proteins comprising one or more of these membrane-anchor proximal regions. In some cases, anti-IL1-RAP antibodies provided herein bind to IL1-RAP proteins comprising one or more of these membrane-anchor proximal regions, but do not bind, or do not substantially bind IL1-RAP proteins that do not comprise one or more of these membrane-anchor proximal regions.

As used herein "receptor IL1-RAP", "membrane IL1-RAP," and "membrane-bound IL1-RAP" and refer to the form of the protein that is present on the surface of cells that express IL1-RAP, e.g., a protein having the amino acid sequence of IL1-Rap (SEQ ID NO:1) (Q9NPH3-1). As such, receptor IL1-RAP, membrane IL1-RAP or membrane-bound IL1-RAP also refer to this form of IL1-RAP when it has been purified from the membrane or is otherwise membrane-free.

As used herein "soluble IL1-RAP" refers to a naturally occurring IL1-RAP protein that is not membrane bound. Specific examples of soluble IL1-RAP proteins include IL1-RAP proteins that do not include the above-mentioned transmembrane region, IL1-RAP proteins that do not include the above-mentioned membrane-anchor proximal regions, IL1-RAP proteins that are not present on the surface of IL1-RAP expressing cells, IL1-RAP proteins that have been proteolytically cleaved such that they are not membrane anchored, cytosolic IL1-RAP, and IL1-RAP proteins that are present in (e.g., secreted into) normal human serum.

One soluble form of IL1-RAP (isoform 2) (Q9NPH3-2) is a 356 amino acid sequence with residues VPAPRY (SEQ ID NO:135) replaced with C-terminal peptide GNRCGQ (SEQ ID NO:4; residues 351-356) and is missing residues 357-570 (relative to isoform 1).

```
                                        (SEQ ID NO: 113)
         10         20         30         40
    MTLLWCVVSL YFYGILQSDA SERCDDWGLD TMRQIQVFED 50         60         70         80
    EPARIKCPLF EHFLKFNYST AHSAGLTLIW YWTRQDRDLE 90        100        110        120
    EPINFRLPEN RISKEKDVLW FRPTLLNDTG NYTCMLRNTT 130        140        150        160
    YCSKVAFPLE VVQKDSCFNS PMKLPVHKLY IEYGIQRITC 170        180        190        200
    PNVDGYFPSS VKPTITWYMG CYKIQNFNNV IPEGMNLSFL 210        220        230        240
    IALISNNGNY TCVVTYPENG RTFHLTRTLT VKVVGSPKNA
```

```
              250        260        270        280
     VPPVIHSPND HVVYEKEPGE ELLIPCTVYF SFLMDSRNEV 290        300        310        320
     WWTIDGKKPD DITIDVTINE SISHSRTEDE TRTQILSIKK 330        340        350
     VTSEDLKRSY VCHARSAKGE VAKAAKVKQK

GNRCGQ
```

Another soluble form (isoform 3) (Q9NPH3-3) is a 346 aa sequence with the sequence ISHSRTEDET (SEQ ID NO:136) . . . GLSYSSLKNV (SEQ ID NO:137) replaced with ASSKIHSGTG (SEQ ID NO:138) . . . PILPGSFWNR (SEQ ID NO:139).

```
                                         (SEQ ID NO: 114)
              10         20         30         40
     MTLLWCVVSL YFYGILQSDA SERCDDWGLD TMRQIQVFED 50         60         70         80
     EPARIKCPLF EHFLKFNYST AHSAGLTLIW YWTRQDRDLE 90        100        110        120
     EPINFRLPEN RISKEKDVLW FRPTLLNDTG NYTCMLRNTT 130        140        150        160
     YCSKVAFPLE VVQKDSCFNS PMKLPVHKLY IEYGIQRITC 170        180        190        200
     PNVDGYFPSS VKPTITWYMG CYKIQNFNNV IPEGMNLSFL 210        220        230        240
     IALISNNGNY TCVVTYPENG RTFHLTRTLT VKVVGSPKNA 250        260        270        280
     VPPVIHSPND HVVYEKEPGE ELLIPCTVYF SFLMDSRNEV 290        300        310        320
     WWTIDGKKPD DITIDVTINE HVVYEKEPGE ELLIPCTVYF 330        340        350
     SFLMDSRNEV WWTIDGKKPD DITIDVTINE
```

In some cases, receptor IL1-RAP includes an intact transmembrane (or membrane anchor) region, or a portion thereof. For example, receptor IL1-RAP may contain the transmembrane spanning region denoted by amino acids 370-388, 369-388, 368-388, 367-388, 366-388, 365-388, 364-388, 363-388, 362-388, 361-388, 370-395, 369-395, 368-395, 368-394, 368-393, 368-392, 368-391, 368-390, or 368-389 of UniprotAccession Q9NPH3-1. Transmembrane regions may include regions of the IL1-RAP primary sequence that are 20 or fewer (e.g., 19, 18, 17, 16, 15, 14, 13, 12, 11, 10, 9, 8, 7, 6, 5, 4, 3, 2, or 1) amino acids in the carboxy or amino direction distal from the above-mentioned residues. In some cases, anti-IL1-RAP antibodies provided herein bind to IL1-RAP proteins comprising one or more of these transmembrane regions. In some cases, receptor IL1-RAP is membrane-bound. For example, the receptor IL1-RAP, or a portion thereof, can be anchored into the membrane of a cell.

In some cases, receptor IL1-RAP is distinguished from soluble IL1-RAP by the presence of the VPAPRYTVELAC (SEQ ID NO: 2) sequence at the carboxy-terminus, which sequence soluble IL1-RAP can lack. In some cases, receptor IL1-RAP is distinguished from soluble IL1-RAP by presence of the HARSAKGEVAKAAKVKQKVPAPRYTVELACGFGATC (SEQ ID NO: 3) sequence at the carboxy-terminus, which sequence soluble IL1-RAP can lack. In some cases, receptor IL1-RAP is distinguished from soluble IL1-RAP by the absence of the GNRCGQ (SEQ ID NO: 4) sequence at the carboxy-terminus, which sequence soluble IL1-RAP can contain.

The terms "receptor IL1-RAP-specific antibody," "anti-receptor IL1-RAP antibody," "membrane IL1-RAP specific antibody," "anti-membrane IL1-RAP antibody," "membrane IL1-RAP antibody," and "antibody that binds to a membrane-bound form of IL1-RAP but does not bind to a soluble form" and the like are used synonymously herein to refer to an antibody that specifically binds to the receptor (i.e., membrane-bound) form of IL1-RAP. In some embodiments, the specific binding to receptor IL1-RAP includes binding to receptor IL1-RAP, but substantially not binding to the soluble form of IL1-RAP found in (e.g., secreted into) normal human serum. In some embodiments, the specific binding to receptor IL1-RAP includes binding to receptor IL1-RAP, but substantially not binding to the soluble form of IL1-RAP comprising the sequence GNRCGQ (SEQ ID NO: 4).

In some embodiments, anti-IL1-RAP antibodies provided herein bind to amino acid residues within the membrane-anchor proximal regions described herein. For example, in some cases, anti-IL1-RAP antibodies provided herein can bind to residues within amino acids 300-368, 320-360, 330-350, or 347-362. In some cases, the anti-IL1-RAP antibodies provided herein bind to regions of the IL1-RAP primary sequence that are 15, 14, 13, 12, 11, 10, 9, 8, 7, 6, 5, 4, 3, 2, or 1 amino acids in the carboxy or amino terminal direction from the above mentioned membrane-anchor proximal region. For example, the antibody can bind to the polypeptides VPAPRYTVELAC (SEQ ID NO: 2) or HARSAKGEVAKAAKVKQKVPAPRYTVELACGFGATC (SEQ ID NO: 3).

In some cases, receptor IL1-RAP-specific antibodies can bind to certain non-natural soluble forms of IL1-RAP, such as a protein that contains the extracellular domain of receptor IL1-RAP (ECD IL1-RAP), including one or more membrane anchor proximal regions, but does not contain a transmembrane region, and/or does not contain GNRCGQ (SEQ ID NO: 4).

In some cases, anti-IL1-RAP antibodies provided herein bind to IL1-RAP proteins comprising one or more of these transmembrane regions, but do not bind IL1-RAP proteins that do not comprise one or more of these transmembrane regions. In some cases, anti-IL1-RAP antibodies provided herein bind IL1-RAP proteins comprising one or more of the above transmembrane regions with a substantially lower dissociation constant (i.e., tighter binding) than IL1-RAP proteins that do not comprise one or more of these transmembrane regions. For example, in some embodiments, anti-IL1-RAP antibodies provided herein can bind IL1-RAP proteins comprising a transmembrane region with a 2, 3, 4, 5, 6, 8, 10, 15, 20, 25, 30, 40, 50, 100, or 1000-fold or greater affinity than IL1-RAP proteins that do not include a transmembrane region.

In some cases, the receptor IL1-RAP antibodies specifically bind to IL1-RAP present on the surface of cells such as certain cancer cells (e.g., cancer stem cells (CSCs) or hematopoietic tumor cells (HTCs)), but not to most mature peripheral blood cells. As discussed in more detail below, in some embodiments the present anti-IL1-RAP antibodies can bind IL1-RAP expressing cells, inhibit their proliferation and/or mediate their destruction.

An "IL1-RAP-associated disorder" (or IL1-RAP related disorder, IL1-RAP disorder, IL1-RAP related condition or disease, etc.) refers to conditions and diseases correlated with elevated or reduced cell surface expression of IL1-RAP as compared to IL1-RAP expression in a standard control (e.g., a normal, non-disease, non-cancer cell). Elevated IL1-RAP levels are associated with cancer cells, in particular, cancer stem cells, in particular, leukemias such as AML (acute myelogenous leukemia), MDS (myelodysplastic syndrome), and CML (chronic myelogenous leukemia), and in hematopoietic CSCs (e.g., LSCs).

The terms "engraft" or "engraftment" refers to the ability of a cell to survive, proliferate, and/or properly localize upon introduction into an individual or tissue. In the case of a cancer stem cell (CSC), the term can refer to the ability of the CSC to generate a tumor de novo or to spread to a different site. The term is commonly used to describe the ability of a population of cells to survive and function in a xenograft model (e.g., engraftment of human cells in a mouse). Engraftment of hematopoietic cells can be determined as described, e.g., in WO2006/047569. Engraftment of tumor cells can be determined as described, e.g., in Beckhove et al. (2003) *Int. J. Cancer* 105:444.

The term "antibody" refers to a polypeptide comprising a framework region from an immunoglobulin gene, or fragments thereof ("antibody fragment"), that specifically bind and recognize an antigen. Typically, the "variable region" contains the antigen-binding region of the antibody (or its functional equivalent) and is most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The term can refer to a whole immunoglobulin (two light chains and two heavy chains, e.g., a tetramer), an immunoglobulin polypeptide (a light chain or a heavy chain), fusion protein comprising a binding portion of an immunoglobulin e.g., chimeric or bispecific antibodies or scFv's or fused to another amino acid sequence, such as a fluorescent protin), and antibody fragments, such as Fab, F(ab')2, Fv, scFv, Fd, dAb, all retaining antigen binding activity. The term includes but is not limited to polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies.

An "isotype" is a class of antibody defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

The term "chimeric antigen receptor" or "CAR" refers to a polypeptide comprising (1) a target binding domain (e.g., a binding portion of an antibody, such as scFV) ; (2) a hinge region; (3) a transmembrane domain (TM); and (4) an intracellular domain comprising at least one signal transduction domain (e.g., CD4).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively. The variable region contains the antigen-binding region of the antibody (or its functional equivalent) and is most critical in specificity and affinity of binding. See Paul, *Fundamental Immunology* (2003).

Antibodies can exist as intact immunoglobulins or as any of a number of well-characterized fragments that include specific antigen-binding activity. For the sake of clarity, a tetrameric antibody with heavy and light chains is referred to herein as an "intact immunoglobulin," and can be naturally occurring, polyclonal, monoclonal, or recombinantly produced. Fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies or those identified using phage display libraries (see, e.g., McCafferty et al., *Nature* 348: 552-554 (1990)).

As used herein, the term "Fv" refers to a monovalent or bi-valent variable region fragment, and can encompass only the variable regions (e.g., $V_L$ and/or $V_H$), as well as longer fragments, e.g., an Fab, Fab' or F(ab')2, which also includes $C_L$ and/or $C_H$1. Unless otherwise specified, the term "Fc" refers to a heavy chain monomer or dimer comprising $C_H$1 and $C_H$2 regions.

A single chain Fv (scFv) refers to a polypeptide comprising a $V_L$ and $V_H$ joined by a linker, e.g., a peptide linker. ScFvs can also be used to form tandem (or di-valent) scFvs or diabodies. Production and properties of tandem scFvs and diabodies are described, e.g., in Asano et al. (2011) *J Biol. Chem.* 286:1812; Kenanova et al. (2010) *Prot Eng Design Sel* 23:789; Asano et al. (2008) *Prot Eng Design Sel* 21:597.

As used herein "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising both the $V_L$ and $V_H$ region. Each $V_L$ and $V_H$ further comprises the segments of Framework 1, CDR1, Framework 2, CDR2, and Framework 3, including CDR3 and Framework 4, which segments are added to the V-segment as a consequence of rearrangement of the respective heavy chain and light chain V-region genes during B-cell differentiation.

As used herein, "variable light chain" and "variable heavy chain" refers to the variable region of the antibody light chain and antibody heavy chain, respectively.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each light and heavy chain are typically referred to as CDRL1, CDRL2, CDRL3 and CDRH1, CDRH2, CDRH3, respectively. Thus, CDRH3 is typically the third CDR located in the variable domain of the heavy chain of the antibody, whereas CDRL1 is the first CDR1 in the variable domain of the light chain.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) *J Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). A helpful guide for locating CDRs using the Kabat system can be found at the website available at bioinforg.uk/abs. Definitions of antigen combining sites are also described in the following: Ruiz et al. *Nucleic Acids Res.,* 28, 219-221 (2000); and Lefranc *Nucleic Acids Res. January* 1; 29(1):207-9 (2001); MacCallum et al., *J. Mol. Biol.,* 262: 732-745 (1996); and Martin et al, *Proc. Natl Acad. Sci.* USA, 86, 9268-9272 (1989); Martin, et al, *Methods Enzymol.,* 203: 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996). In some embodiments, the CDRs of the receptor IL1-RAP antibodies of the disclosure are identified in FIG. 12.

A "chimeric antibody" refers to an antibody in which (a) the constant region, or a portion thereof, is altered, replaced or exchanged so that the antigen binding site (variable region, CDR, or portion thereof) is linked to a constant region of a different or altered class, effector function and/or species; or (b) the variable region, or a portion thereof, is altered, replaced or exchanged with a variable region having a different or altered antigen specificity (e.g., CDR and framework regions from different species). Chimeric antibodies can include variable region fragments, e.g., a recombinant antibody comprising two Fab or Fv regions or an scFv. A chimeric can also, as indicated above, include an Fc region from a different source than the attached Fv regions. In some cases, the chimeric antibody includes chimerism within the Fv region. An example of such a chimeric antibody would be a humanized antibody where the Fvs and CDRs are from different sources.

Humanized antibodies are antibodies in which the antigen binding loops, i.e., CDRs, obtained from the $V_H$ and $V_L$ regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

As used herein, the term "percent (%) identity" refers to the percentage of amino acid (or nucleic acid) residues of a candidate sequence, e.g., an isolated anti-IL1-RAP antibody of the invention, that are identical to the amino acid (or nucleic acid) residues of a reference sequence, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved using BLAST® 2.0 software using standard settings. Alignment can be performed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of A/B})$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody target will typically bind the primary antibody with at least a 2-fold greater affinity than a non-primary antibody target target (e.g., an antibody from a different species or of a different isotype, or a non-antibody target). For example, an antibody that specifically binds the receptor form of IL1-RAP will typically bind to the receptor form of IL1-RAP with at least a 2-fold greater affinity than a non-target molecules (e.g., the soluble form of IL1-RAP, proteins related to IL1-RAP, or other proteins).

As used herein, an antibody does not "substantially bind" a target if it binds the target with a KD greater than $10^{-6}$ M.

The term "binds" with respect to a cell type (e.g., an antibody that binds lymphoma cells), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%) if the antibody is in high enough concentration. In some cases, receptor-IL1-RAP specific binding can be assayed by comparing binding of the antibody to a cell that expresses membrane-bound IL1-RAP to binding (or lack thereof) of the antibody to a cell that does not express membrane-bound IL1-RAP. One of skill will recognize that some variability will arise depending on the method and/or threshold of determining binding.

The term "captures" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The term "cross-linked" with respect to an antibody refers to attachment of the antibody to a solid or semisolid matrix (e.g., sepharose, beads, culture plate), or to another protein or antibody. For example, the antibody can be multimerized to create an antibody complex with multiple (more than 2) antigen-binding sites. The antibody can be multimerized by expressing the antibody as a high-valency isotype (e.g., IgA or IgM, which typically form complexes of 2 or 5 antibodies, respectively). Antibody multimerization can also be carried out by using a cross-linker comprising a reactive group capable of linking proteins (e.g., carbodiimide, NHS esters, etc.). Methods and compositions for cross-linking an antibody to a matrix are described, e.g., in the Abcam and New England Biolab catalogs and websites (available at abcam.com and neb.com). Cross-linker compounds with various reactive groups are described, e.g., in Thermo Fisher Scientific catalog and website (available at piercenet.com).

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., at least any of 20%, 30%, 40%, 50%, 60%, 70%, 80%, or more, e.g., so that binding of the second antibody to target is undetectable in the presence of the first (competitor) antibody.

The terms "label," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}$P, $^{3}$H), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target analyte. Any method known in the art for conjugating an antibody to the label may be employed, e.g., using methods described in Hermanson, *Bioconjugate Techniques* 1996, Academic Press, Inc., San Diego. The term "tag" can be used synonymously with the term "label," but generally refers to an affinity-based moiety, e.g., a "His tag" for purification, or a "streptavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "differentially expressed" or "differentially regulated" refers generally to a protein or nucleic acid biomarker that is overexpressed (upregulated) or underexpressed (downregulated) in one sample compared to at least one other sample. In the context of the present disclosure, the term generally refers to overexpression of receptor IL1-RAP on a cancer cell (e.g., an AML cell or AML CSC) as opposed to soluble IL-1RAP, as present in undiseased tissue.

For example, the terms "overexpressed" or "upregulated" interchangeably refer to a protein or nucleic acid, generally a biomarker that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be at least any of 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased at least any of 10%, 20%, 30%, 40%, 50%, 60%, 70%, 80%, 90% 100% or more than that in a control. In certain instances, the activation is any of 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be any of 10%, 20%, 30%, 40%, 50%, 60%, 70%, 80%, 90% or less than that in a control. In certain instances, the inhibition is any of 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). In the context of the present disclosure, an example of a negative control would be a biological sample from a known healthy (non-cancer) individual, and an example of a positive control would be a biological sample from a known AML patient. A control can also represent an average value or a range gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a subject has a disorder such as cancer. Similarly, the term "prognosis" refers to a relative probability that a certain future outcome may occur in the subject. For example, in the context of the present disclosure, prognosis can refer to the likelihood that an individual will develop cancer, have recurrence, be cured, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, an IL1-RAP associated disorder. The sample can also be a blood sample or blood fraction, e.g., white blood cell fraction, serum, or plasma. In some embodiments, the sample may be a tissue biopsy, such as needle biopsy, fine needle biopsy, surgical biopsy, etc. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating cancer (e.g., AML), treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

"Inhibits" or "inhibition" as used herein, e.g., inhibition of characteristics such as cellular growth, proliferation, metabolic activity, viability, survival or division refers to a decrease in the characteristic relative to a control. In some cases, a compound of the present invention may inhibit one of the foregoing characteristics. For example, a cell treated with an antibody described herein may exhibit a decrease in one of the foregoing characteristics of approximately 1%, 2%, 3%, 4%, 5%, 6%, 7%, 8%, 9%, 10%, 12%, 15%, 20%, 25%, 30%, 35%, 40%, 45%, 50%, 60%, 70%, 75%, 80%, 85%, 90%, 95%, 97.5%, 99%, 99.5%, 99.9% or more as compared to an untreated cell. In some cases, a cell treated with a compound of the present invention may exhibit a growth, proliferation, metabolic activity, viability, survival or division that is less than about 1%, 2%, 3%, 4%, 5%, 6%, 7%, 8%, 9%, 10%, 12%, 15%, 20%, 25%, 30%, 35%, 40%, 45%, 50%, 60%, 70%, 75%, 80%, 85%, 90%, 95%, 97.5%, 99%, 99.5%, 99.9% of a control (e.g. untreated) cell.

"Inhibitors," of IL1-RAP activity refer to inhibitory molecules identified using in vitro and in vivo assays for IL1-RAP activity, e.g., antagonists, and their homologs and mimetics. Inhibitors can, e.g., bind to or inactivate the activity of IL1-RAP. Inhibitors include naturally occurring and synthetic antagonists (e.g., small chemical molecules, antibodies and the like that function as antagonists). Such assays for inhibitors include, e.g., applying putative inhibitor compounds to cells expressing IL1-RAP and then determining the binding to the cells or measuring the functional activity of IL1-RAP, as described herein. Functional activity of IL1-RAP can include cellular proliferation or cell survival. Cells expressing IL1-RAP that are treated with a potential inhibitor are compared to control samples without the inhibitor to examine the extent of effect. Control cells (untreated) are assigned a relative IL1-RAP activity value of 100%.

Inhibition of IL1-RAP is achieved when the IL1-RAP activity value relative to the control is about 80%, or 70%, optionally 50%, 40%, 30%, 25%, 20%, 15%, 10%, 5%, 1% or lower. Inhibition of IL1-RAP can provide a decrease in cellular proliferation or a decrease in cell survival. In other cases, inhibition can be detected by a decrease in binding or association of IL1-RAP to a ligand or another protein, e.g. IL1R1, TOLLIP, MYD88, IRAK1 or IRAK2. In still other cases, inhibition can be detected by a decrease in interleukin-1-dependent activation of NF-kappa-B. Inhibition can also be detected by a decrease in the clonogenicity of, or decrease in the survival of, AML cells. In one embodiment, IL1-RAP activity can be determined as shown in Example 6.

As used herein, the term "pharmaceutically acceptable" refers to a carrier that is compatible with the other ingredients of the formulation and not deleterious to the recipient thereof." The term is used synonymously with "physiologically acceptable" and "pharmacologically acceptable". A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc. A "cancer patient" or "AML patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles and clinical correlates* ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to leukemias, carcinomas, sarcomas, adenocarcinomas, lymphomas, solid and lymphoid cancers, etc. Examples of different types of cancer include, but are not limited to, acute myelogenous leukemia (AML), chronic myelogenous leukemia (CML), B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, multiple myelomas, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, osteogenic sarcoma, fibrosarcoma, neuroblastoma, glioma, and melanoma.

A "cancer target" or "cancer marker" is a molecule that is differentially expressed or processed in cancer, e.g., on a cancer cell or in the cancer milieu. Exemplary cancer targets are cell surface proteins such as receptor IL1-RAP (also, e.g., cell adhesion molecules and receptors), intracellular receptors, hormones, and molecules such as proteases that are secreted by cells into the cancer milieu. Markers for specific cancers are known in the art, e.g., CD45 for AML, CD34+CD38− for AML CSCs, MUC1 expression on colon and colorectal cancers, bombesin receptors in lung cancer, and prostate specific membrane antigen (PSMA) on prostate cancer.

In some embodiments, the cancer target can be associated with a certain type of cancer cell, e.g., AML, leukemia, myeloma, lymphoma, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least any of 3, 4, 5, 6, 7, 8, 9, 10, 20, 50, 100, or 1000 fold higher than its average expression in a reference population. Thus, the target can be detected or measured to distinguish the cell type or types of interest from other cells. For example, AML cancer targets include CLL-1, IL1-RAP, GPR114, Ly86, LILRA1, and CD180.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1: 10,000. Hematopoietic CSCs can be identified as CD34+, similar to normal hematopoietic stem cells (HSCs). Other CSC associated markers include CD44 (breast), CD133 (glial cancers), and Notch (e.g., myelomas and neuroblastoma).

An "inflammatory condition" refers to any inflammation in an individual, and can be transient (e.g., in response to exposure to a pathogen or allergen) or chronic. Inflammation is characterized by inflammatory cytokines such as IFN-gamma, IL-6, and TNF-alpha that recruit and activate macrophages and other leukocytes. In some cases, inflammation can develop into a chronic, harmful condition or autoimmune condition (e.g., MS, lupus, rheumatoid arthritis, Crohn's disease). Inflammation can be evident locally (e.g., at a localized site of infection or exposure) or systemically (e.g., atherosclerosis, high blood pressure).

The terms "internalize," "internalization," "endocytose," "endocytosis," "engulf," and like terms refer to uptake of a substance by a cell, e.g., by antibody (or receptor)-mediated endocytosis or phagocytosis.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be naturally occurring ribonucleotides or deoxyribonucleotides, or synthetic or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring amino acids, modified or synthetic amino acids, as well as amino acid analogs and amino acid mimetics that function similarly to naturally occurring amino acids. Naturally occurring amino acids are those encoded by the genetic code. Modified amino acids include, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide are implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST® or BLAST® 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous," with reference to a polynucleotide or polypeptide, indicates that the polynucleotide or polypeptide comprises two or more subsequences that are not found in the same relationship to each other in nature. For instance, a heterologous polynucleotide or polypeptide is typically recombinantly produced, having two or more sequences from unrelated genes arranged to make a new functional unit, e.g., a promoter from one source and a coding region from another source. Similarly, a heterologous protein indicates that the protein comprises two or more subsequences that are not found in the same relationship to each other in nature (e.g., a fusion protein).

III. IL1-RAP Associated Disorders

IL1-RAP disorders can be treated, prevented, ameliorated, or mitigated with an antibody as described herein. IL1-RAP associated disorders include cancers associated with elevated IL1-RAP expression and inflammatory disorders associated with reduced IL1-RAP expression, as described herein. The antibodies of the invention can be used for diagnosis and monitoring of these disorders, as well as targeted therapy, e.g., delivering an antibody or an antibody conjugated to a chemotherapeutic (or cytotoxic) agent specifically to an IL1-RAP-expressing cell, such as a cancer cell while avoiding or reducing delivery to other cells. In some cases, the targeted therapy can comprise contacting an IL1-RAP-expressing cell with an antibody, as described herein.

IL1-RAP expression is associated with myelomas and other hematopoietic cell cancers, and carcinomas (e.g., carcinomas of the colon, ovary, liver, prostate, uterus, breast, and kidney). Examples of cancers that can be targeted using a receptor IL1-RAP-specific antibody thus include hematopoietic cell cancers (e.g., B cell lymphoma, Burkitt's lymphoma, Hodgkin's lymphoma, non-Hodgkin's lymphoma, myelodysplastic syndrome (preleukemia), leukemias, and myelomas (e.g., acute myeloid leukemia (AML), chronic myeloid leukemia (CML), chronic myelomoncytic leukemia (CMML), multiple myeloma, plasmacytoma)). Additional IL1-RAP expressing cancers that can be targeted using the presently disclosed antibodies include but are not limited to colon carcinoma, ovarian carcinoma, prostate carcinoma, breast carcinoma, renal carcinoma, liver carcinoma, and uterine carcinoma. Myelodysplastic syndromes (MDS) can also be targeted using a receptor IL1-RAP-specific antibody.

In some cases, IL1-RAP associated disorders that may be treated by the anti-IL1-RAP antibodies provided herein include joint, bone, and muscle diseases such as rheumatoid arthritis, ankylosing spondylitis, erosive osteoarthritis of the hand, recurrent multifocal osteomyelitis, traumatic knee injury, and relapsing polychondritis. In some cases, IL1-RAP associated disorders that may be treated by the anti-IL1-RAP antibodies provided herein include hereditary systemic auto-inflammatory diseases such as familial Mediterranean fever, cryopyrin-associated periodic syndrome, TNF receptor-associated periodic syndrome, hyper-IgD syndrome, periodic fever, aphthous stomatitis, pharyngitis and adenitis, and deficiency of IL-1 receptor antagonist. In some cases, IL1-RAP associated disorders that may be treated by the anti-IL1-RAP antibodies provided herein include systemic inflammatory diseases such as systemic juvenile idiopathic arthritis, adult-onset Still's disease, Schnitzler syndrome, Behcet's disease, synovitis acne pustulosis hyperostosis osteitis syndrome, and macrophage activation syndrome. In some cases, IL1-RAP associated disorders that may be treated by the anti-IL1-RAP antibodies provided herein include common inflammatory diseases such as gout, pseudogout, type-2 diabetes, hidradenitis suppurativa, systolic heart failure, cardiac remodeling, dry eye syndrome, pustular psoriasis, and neutrophilic dermatoses. Further examples of IL1-RAP associated disorders include diseases and conditions described in Dinarello et al. *Nature Reviews Drug Discovery*, Volume 11 August 2012 p. 613 and supplementary materials provided therein.

AML cells can be characterized and distinguished from other cells by detecting cell surface marker expression. Aside from being CLL-1+, AML cells can be CD33+ (though some are CD33−), CD45+, and CDw52+. AML blasts (including LSCs) are typically CD34+CD38−. HSCs and LSCs can be characterized by expression of CD34, but the former do not express CLL-1. MDS cells can be characterized by expression of CD5, CD7, CD13, and CD34. CML cells can be characterized by expression of 7-ADD, CD33, CD34, and CD38.

Myelodysplastic Syndromes (MDS) include a group of closely-related blood formation disorders, in which the bone marrow shows qualitative and quantitative changes suggestive of a preleukemic process, but having a chronic course that does not necessarily terminate as acute leukemia. A variety of terms, including preleukemia, refractory anemia, refractory dysmyelopoietic anemia, smoldering or subacute leukemia, dysmyelopoietic syndrome (DMPS), and myelodysplasia, have all been used to describe MDS. These conditions are all characterized by a cellular marrow with impaired maturation (dysmyelopoiesis) and a reduction in the number of blood cells. DMPS is characterized by presence of megablastoids, megakaryocyte dysplasia, and an increase in number of abnormal blast cells, reflective of enhanced granulocyte maturation process. Patients with DMPS show chromosomal abnormalities similar to those found in acute myeloid leukemia and progress to acute myeloid leukemia in a certain fraction of afflicted patients.

Chronic myeloproliferative disorders are a collection of conditions characterized by increased number of mature and immature granulocytes, erythrocytes, and platelets. Chronic myeloproliferative disorders can transition to other forms within this group, with a tendency to terminate in acute myeloid leukemia. Specific diseases within this group include polycythemia vera, chronic myeloid leukemia, agnogenic myeloid leukemia, essential thrombocythemia, and chronic neutrophilic leukemia.

Myelofibrosis is characterized by scarring of the bone marrow that results in reduced number of red and white blood cells, and platelets. Myelofibrotic scarring can result from leukemia, but can have other causes, such as thrombocytosis or adverse drug effects.

IV. Anti-IL1-RAP Antibodies

Provided herein are anti-IL1-RAP antibodies (including, for example, receptor IL1-RAP-specific antibodies, anti-receptor IL1-RAP that specifically bind to the membrane-bound form of IL1-RAP but do not substantially bind a soluble form of IL1-RAP). In some embodiments, the anti-IL1-RAP antibodies provided herein specifically bind the membrane-bound form of IL1-RAP but do not bind a soluble form of IL1-RAP. Anti- receptor IL1-RAP antibodies described herein can also inhibit growth of IL1-RAP-expressing cells. In part in view of the data described herein, it is believed these anti-IL1-RAP antibodies can be used to inhibit cell growth of IL1-RAP expressing cells (e.g., cancer cells) in the absence of a conjugated cytotoxic agent. It is also believed anti-IL1-RAP antibodies described herein also show complement dependent cytotoxicity (CDC) activity or antibody dependent cell-mediated cytotoxicity (ADCC). It is believed these anti-IL1-RAP antibodies can also be used to target IL1-RAP expressing cells for destruction, e.g. in the absence of a conjugated cytotoxic agent. However, in some cases, cytotoxic agents may nevertheless be conjugated to anti-IL1-RAP antibodies of the invention.

Anti-IL1-RAP antibodies described herein have unique cell binding activities, such as those described in the examples herein. For example, anti-IL1-RAP antibodies can be used to target eosinophilic leukemia cells (exemplified as EOL-1 cells). In some embodiments, anti-IL1-RAP antibodies can also bind AML, CML, or MDS cells, or solid tumor cells such as liver, kidney, lung, and brain tumor cells. In some embodiments, these antibodies can be used for detecting cancer cells that display an epitope that is targeted with high affinity by at least one of the anti-IL1-RAP antibodies disclosed herein. In some embodiments, those cancer cells can then be targeted for destruction with the same anti-IL1-RAP antibody. Such methods can include treating an individual having IL1-RAP expressing cancer cells, e.g., as described herein, comprising administering the anti-IL1-RAP antibody to the individual.

In some cases, the anti-IL1-RAP antibodies have significant and surprising advantages over previously described anti-IL1-RAP antibodies. For example, IL1-RAP is expressed in a soluble and a membrane-bound form. In some cases, the soluble form is present in (e.g., secreted into) normal human serum. The inventors have discovered that antibodies that bind both the soluble and membrane-bound form may therefore be blocked by the soluble form of IL1-RAP and fail to accumulate on the surface of IL1-RAP expressing cells.

In some cases, anti-IL1-RAP antibodies described herein provide significant advantages over previously described anti-IL1-RAP antibodies because the antibodies provided herein activate, or strongly activate antibody dependent cell-mediated cytotoxicity (ADCC) or complement dependent cytotoxicity (CDC), or a combination thereof. In some cases, receptor-specific IL1-RAP antibodies described herein provide significantly greater activation of ADCC and/or CDC in comparison to anti-IL1-RAP antibodies that are not receptor specific. For example, in some cases, the receptor-specific IL1-RAP antibodies are capable of binding in large numbers to cells expressing membrane-bound IL1-RAP, and are not, or not substantially, competed away from binding to these cells by soluble IL1-RAP. In some cases, the antibodies provided herein are particularly advantageous for delivery of a cytotoxic or chemotherapeutic agent to cells expressing the receptor form of IL1-RAP regardless of the presence of soluble IL1-RAP.

In some embodiments, the anti-IL1-RAP antibody binds the same epitope as an antibody having the CDR sequences of antibodies 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2 or 44.5D2. In some embodiments, the anti-IL1-RAP antibody comprises 3 heavy chain CDRs and/or 3 light chain CDRs selected from the CDRs of antibody clones 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2 or 44.5D2. The CDRs can come from the same antibody or different antibodies among the group. In some embodiments, the anti-IL1-RAP antibody has a light chain CDR sequence and heavy chain CDR sequence having up to 1, 2, 3, or 4 amino acid substitutions, additions, or deletions/CDR relative to one or more CDR sequences of antibody 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2 or 44.5D2. In some embodiments, the light chain CDR sequences include up to 1, 2, 3, or 4 amino acid substitutions, additions or deletions/ CDR relative to one or more light chain CDR sequences of the aforementioned anti-IL1-RAP antibodies. In some embodiments, the heavy chain CDR sequences include up to 1, 2, 3, or 4 amino acid substitutions, additions, or deletions/CDR relative to one or more heavy chain CDR sequences of the aforementioned anti-IL1-RAP antibodies. In some embodiments, substitution, addition or deletion occurs in only 1, 2, 3, 4, or 5 CDRs of the 6 total CDRs. In some embodiments, the anti-IL1-RAP antibody has variable region sequences with at least 75%, 80%, 85%, 90%, 95% identity or 96%, 97%, 98%, 99% or 100% identity to those of 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2 or 44.5D2. In some embodiments, the anti-IL1-RAP antibody has CDR sequence identity in the light chain and/or heavy chain CDRs of at least 95% identity or 96%, 97%, 98%, 99% or 100% identity to those of 54.9D7, 56.12G6, 2H8, 50.3G7, 54.15B5, 42.1D3, 54.8H8, 54.9E9, 50.6C12, 57.7A9, 46.8G1, 42.3G6, 46.1D2, 41.10C2, 46.2C2 or 44.5D2.

In some cases, anti-IL1-RAP antibodies can comprise light chain variable region sequence and/or the heavy chain variable region sequence of the clone 54.9D7.

```
54.9D7 light chain variable region sequence:
                                          SEQ ID NO: 5
DIVLTQSPISLAVFLGQRATISCRASQSVSTSGYSSMHWYQQKAGQPPKL

LIKYASDLESGVPVRFSGSGSGTDFILNIHPVEVEDIATYYCHHSWGIPM

YTFGGGTKLEIKR
```

54.9D7 heavy chain variable region sequence
SEQ ID NO: 6
HVQLQQSGPELVRPGASVKLSCKASGYIFITYWMNWVKQRPGQGLEWVGQ

IFPASGTTYYNELFEGKATLTVDTSSNTAYMHLTSLTSEDSAVYYCARTD

FYRYDGGYALDYWGQGTSLTVSS 54.9D7 humanized light chain variable region
sequence variant 1
SEQ ID NO: 115
DIQMTQSPSSLSASVGDRVTITCRASQSVSTSGYSSMHWYQQKPGKAPKL

LIYYASDLESGVPSRFSGSGSGTDFTLTISSLQPEDFATYYCHHSWGIPM

YTFGQGTKLEIKR 54.9D7 humanized light chain variable region
sequence variant 2
SEQ ID NO: 116
DIQLTQSPSSLSASVGDRATITCRASQSVSTSGYSSMHWYQQKPGKAPKL

LIYYASDLESGVPSRFSGSGSGTDFTLTISSVQPEDFATYYCHHSWGIPM

YTFGQGTKLEIKR 54.9D7 humanized light chain variable region
sequence variant 3
SEQ ID NO: 117
DIQLTQSPSSLSASVGDRATITCRASQSVSTSGYSSMHWYQQKPGKAPKL

LIKYASDLESGVPSRFSGSGSGTDFTLTISSVQPEDFATYYCHHSWGIPM

YTFGQGTKLEIKR 54.9D7 humanized heavy chain variable region
sequence variant 1
SEQ ID NO: 118
QVQLVQSGAEVKKPGASVKVSCKASGYIFITYVVMNWVRQAPGQGLEWMG

QIFPASGTTYYAQKFQGRVTMTRDTSTSTVYMELSSLRSEDTAVYYCART

DFYRYDGGYALDYWGQGTLVTVSS 54.9D7 humanized heavy chain variable region
sequence variant 2
SEQ ID NO: 119
QVQLVQSGAEVKKPGASVKVSCKASGYIFITYWMNWVRQAPGQGLEWVGQ

IFPASGTTYYAQKFQGRVTMTVDTSTSTVYMELSSLRSEDTAVYYCARTD

FYRYDGGYALDYWGQGTLVTVSS 54.9D7 humanized heavy chain variable region
sequence variant 3
SEQ ID NO: 120
QVQLVQSGAEVKKPGASVKLSCKASGYIFITYWMNWVRQAPGQGLEWVGQ

IFPASGTTYYAQKFQGRATLTVDTSTSTAYMELSSLRSEDTAVYYCARTD

FYRYDGGYALDYWGQGTLLTVSS 54.9D7 humanized heavy chain variable region
sequence variant 4
SEQ ID NO: 121
EVQLVQSGAEVKKPGASVKVSCKASGYIFITYWMNWVRQAPGQGLEWVGQ

IFPASGTTYYAQKFQGRVTMTVDTSTSTVYMELSSLRSEDTAVYYCARTD

FYRYEGGYALDYWGQGTLVTVSS

In other cases, anti-IL1-RAP antibodies can comprise a 54.9D7 light chain variable region that is at least 85%, 90%, 95%, 97%, 98%, or 99% identical to SEQ ID NO: 5. Additionally, or in the alternative, anti-IL1-RAP antibodies can comprise a 54.9D7 heavy chain variable region that is at least 85%, 90%, 95%, 96% 97%, 98%, or 99% identical to SEQ ID NO: 6.

In other cases, anti-IL1-RAP antibodies can comprise a 54.9D7 humanized light chain variable region that is at least 85%, 90%, 95%, 97%, 98%, or 99% identical to SEQ ID NO: 115. In other cases, anti-IL1-RAP antibodies can comprise a 54.9D7 humanized light chain variable region that is at least 85%, 90%, 95%, 97%, 98%, or 99% identical to SEQ ID NO: 116. In other cases, anti-IL1-RAP antibodies can comprise a 54.9D7 humanized light chain variable region that is at least 85%, 90%, 95%, 97%, 98%, or 99% identical to SEQ ID NO: 117. Additionally, or in the alternative, anti-IL1-RAP antibodies can comprise a 54.9D7 heavy chain variable region that is at least 85%, 90%, 95%, 96% 97%, 98%, or 99% identical to SEQ ID NO: 118. Additionally, or in the alternative, anti-IL1-RAP antibodies can comprise a 54.9D7 heavy chain variable region that is at least 85%, 90%, 95%, 96% 97%, 98%, or 99% identical to SEQ ID NO: 119. Additionally, or in the alternative, anti-IL1-RAP antibodies can comprise a 54.9D7 heavy chain variable region that is at least 85%, 90%, 95%, 96% 97%, 98%, or 99% identical to SEQ ID NO: 120. Additionally, or in the alternative, anti-IL1-RAP antibodies can comprise a 54.9D7 heavy chain variable region that is at least 85%, 90%, 95%, 96% 97%, 98%, or 99% identical to SEQ ID NO: 121.

The sequence alignment of the light chain variable region sequence of chimeric 54.9D7 (SEQ ID NO: 5), humanized light chain variable region sequence variant 1 of 54.9D7 (SEQ ID NO: 115), humanized light chain variable region sequence variant 2 of 54.9D7 (SEQ ID NO: 116), humanized light chain variable region sequence variant 3 of 54.9D7 (SEQ ID NO: 117) is shown below. Amino acids in each of humanized light chain variable region sequences (SEQ ID NOs: 115-117) that differ from the sequence of SEQ ID NO: 5 are indicated by "•" or ":".

```
Sequence Alignment of SEQ ID NOs: 5 and 115-117

SEQ5    DIVLTQSPISLAVFLGQRATISCRASQSVSTSGYSSMHWYQQKAGQPPKLLIKYASDLES
SEQ115  DIQMTQSPSSLSASVGDRVTITCRASQSVSTSGYSSMHWYQQKPGKAPKLLIYYASDLES
SEQ116  DIQLTQSPSSLSASVGDRATITCRASQSVSTSGYSSMHWYQQKPGKAPKLLIYYASDLES
SEQ117  DIQLTQSPSSLSASVGDRATITCRASQSVSTSGYSSMHWYQQKPGKAPKLLIKYASDLES
        ** :**** **:. :*:*.**:********************* *: ***** *******

SEQS    GVPVRFSGSGSGTDFILNIHPVEVEDIATYYCHHSWGIPMYTFGGGTKLEIKR
SEQ115  GVPSRFSGSGSGTDFTLTISSLQPEDFATYYCHHSWGIPMYTFGQGTKLEIKR
SEQ116  GVPSRFSGSGSGTDFTLTISSVQPEDFATYYCHHSWGIPMYTFGQGTKLEIKR
SEQ117  GVPSRFSGSGSGTDFTLTISSVQPEDFATYYCHHSWGIPMYTEGQGTKLEIKR
        *** ********** *.*   :: **:********************* *******
```

The sequence alignment of the heavy chain variable region sequence of chimeric 54.9D7 (SEQ ID NO: 6), humanized heavy chain variable region sequence variant 1 of 54.9D7 (SEQ ID NO: 118), humanized heavy chain variable region sequence variant 2 of 54.9D7 (SEQ ID NO: 119), humanized heavy chain variable region sequence variant 3 of 54.9D7 (SEQ ID NO: 120), and humanized heavy chain variable region sequence variant 4 of 54.9D7 (SEQ ID NO: 121) is shown below. Amino acids in each of humanized heavy chain variable region sequences (SEQ ID NOs: 118-121) that differ from the sequence of SEQ ID NO: 6 are indicated by "•" or ":".

```
Sequence Alignment of SEQ ID NOs: 6 and 118-121

SEQ6     HVQLQQSGPELVRPGASVKLSCKASGYIFITYWMNWVKQRPGQGLEWVGQIFPASGTTYY
SEQ118   QVQLVQSGAEVKKPGASVKVSCKASGYIFITYWMNWVRQAPGQGLEWMGQIFPASGTTYY
SEQ119   QVQLVQSGAEVKKPGASVKVSCKASGYIFITYWMNWVRQAPGQGLEWVGQIFPASGTTYY
SEQ120   QVQLVQSGAEVKKPGASVKLSCKASGYIFTTYWMNWVRQAPGQGLEWVGQIFPASGTTYY
SEQ121   EVQLVQSGAEVKKPGASVKVSCKASGYIFITYWMNWVRQAPGQGLEWVGQIFPASGTTYY
         .*** *** *: :******:****************:* *******:************

SEQ6     NELFEGKATLTVDTSSNTAYMHLTSLTSEDSAVYYCARTDFYRYDGGYALDYWGQGTSLT
SEQ118   AQKFQGRVTMTRDTSTSTVYMELSSLRSEDTAVYYCARTDFYRYDGGYALDYWGQGTLVT
SEQ119   AQKFQGRVTMTVDTSTSTVYMELSSLRSEDTAVYYCARTDFYRYDGGYALDYWGQGTLVT
SEQ120   AQKFQGRATLTVDTSTSTAYMELSSLRSEDTAVYYCARTDFYRYDGGYALDYWGQGTLLT
SEQ121   AQKFQGRVTMTVDTSTSTVYMELSSLRSEDTAVYYCARTDFYRYEGGYALDYWGQGTLVT
         : *:*:.*:* ***:.*.**.*:** ***.************:************ :*

SEQ6     VSS
SEQ118   VSS
SEQ119   VSS
SEQ120   VSS
SEQ121   VSS
         ***
```

In some cases, anti-IL1-RAP antibodies can comprise one or more 54.9D7 CDRs that are 95%, 96%, 97%, 98%, 99%, or 100% identical to the CDRs selected from the group consisting of:

54.9D7; CDRH1: GYIFITY
SEQ ID NO: 7

54.9D7; CDRH2: FPASGT
SEQ ID NO: 8

54.9D7; CDRH3: TDFYRYDGGYALDY
SEQ ID NO: 9

54.9D7; CDRL1: RASQSVSTSGYSSMH
SEQ ID NO: 10

54.9D7; CDRL2: YASDLES,
and
SEQ ID NO: 11

54.9D7; CDRL3: HHSWGIPMYT
SEQ ID NO: 12

In some cases, anti-IL1-RAP antibodies can comprise one or more 54.9D7 CDRs that contain 1, 2, 3, or 4 amino acid substitutions or deletions as compared to a CDR selected from the group consisting of:

54.9D7; CDRH1: GYIFITY
SEQ ID NO: 7

54.9D7; CDRH2: FPASGT
SEQ ID NO: 8

54.9D7; CDRH3: TDFYRYDGGYALDY
SEQ ID NO: 9

54.9D7; CDRL1: RASQSVSTSGYSSMH
SEQ ID NO: 10

54.9D7; CDRL2: YASDLES,
and
SEQ ID NO: 11

54.9D7; CDRL3: HHSWGIPMYT
SEQ ID NO: 12

In some cases, anti-IL1-RAP antibodies can comprise light chain variable region sequence and/or the heavy chain variable region sequence of the clone 56.12G6.

56.12G6 light chain variable region sequence:
SEQ ID NO: 13
QIVLTQSPAIMSAFPGEKVTMTCRASSSVSYMHWYRQKSGTFPKRWIYD
TSKLASGVPARFSGSGSGTSYSLTISSMEAEDAATYYCQQWSTNPITFG
AGTKLELK 56.12G6 heavy chain variable region sequence
SEQ ID NO: 14
RSNYSSLGAELVKPGASVTLSCEASGYTFTSYWIHWVKQRPGQGLEWI
GEINPSHGHTTYNEKFKNKATLTVDKSSSTAYMQVSSLTSEDSAVYYC
TRHYGSYYFDLWGQGTTLTVSS In other cases, anti-IL1-RAP antibodies can comprise a 56.12G6 light chain variable region that is at least 85%, 90%, 95%, 97%, 98%, or 99% identical to SEQ ID NO: 13. Additionally, or in the alternative, anti-IL1-RAP antibodies can comprise a 56.12G6 heavy chain variable region that is at least 85%, 90%, 95%, 96% 97%, 98%, or 99% identical to SEQ ID NO: 14.

In some cases, anti-IL1-RAP antibodies can comprise one or more 56.12G6 CDRs that are 95%, 96%, 97%, 98%, 99%, or 100% identical to the CDRs selected from the group consisting of:

56.12G6; CDRH1: GYTFTSY
SEQ ID NO: 15

```
                                SEQ ID NO: 16
56.12G6; CDRH2: NPSHGH

SEQ ID NO: 17
56.12G6; CDRH3: HYGSYYFDL

SEQ ID NO: 18
56.12G6; CDRL1: RASSSVSYMH

SEQ ID NO: 19
56.12G6; CDRL2: DTSKLAS,
and

SEQ ID NO: 20
56.12G6; CDRL3: QQWSTNPIT
```

In some cases, anti-IL1-RAP antibodies can comprise one or more 56.12G6 CDRs that contain 1, 2, 3, or 4 amino acid substitutions or deletions as compared to a CDR selected from the group consisting of:

```
                                SEQ ID NO: 15
56.12G6; CDRH1: GYTFTSY

SEQ ID NO: 16
56.12G6; CDRH2: NPSHGH

SEQ ID NO: 17
56.12G6; CDRH3: HYGSYYFDL

SEQ ID NO: 18
56.12G6; CDRL1: RASSSVSYMH

SEQ ID NO: 19
56.12G6; CDRL2: DTSKLAS,
and

SEQ ID NO: 20
56.12G6; CDRL3: QQWSTNPIT
```

In some cases, anti-IL1-RAP antibodies can comprise light chain variable region sequence and/or the heavy chain variable region sequence of the clone 2H8.

```
2H8 light chain variable region sequence:
                                SEQ ID NO: 126
DIVLTQSPASLAVSLGQRATISCRASESVDSYGNSFMHWYQQKPGQP

PKLLIYRASNLESGIPARFSGSGSRTDFTLTINPVEADDVATYYCQQSN

EDPWTFGGGTKLEIK

2H8 heavy chain variable region sequence
                                SEQ ID NO: 127
QIQLVQSGPELKKPGETVKISCKASGYTFTDYSMHWVKQAPGKGLKWM

GWINTETGEPTYADDFKGRFAFSLETSASTAYLQINNLKNEDTATYFCAR

YYGYFDYWGQGTTLTVSS
```

In other cases, anti-IL1-RAP antibodies can comprise a 2H8 light chain variable region that is at least 85%, 90%, 95%, 97%, 98%, or 99% identical to SEQ ID NO: 126. Additionally, or in the alternative, anti-IL1-RAP antibodies can comprise a 2H8 heavy chain variable region that is at least 85%, 90%, 95%, 96% 97%, 98%, or 99% identical to SEQ ID NO: 127.

In some cases, anti-IL1-RAP antibodies can comprise one or more a 2H8 CDRs that are 95%, 96%, 97%, 98%, 99%, or 100% identical to the CDRs selected from the group consisting of:

```
                                SEQ ID NO: 21
2H8; CDRH1: GYTFTDYSMH

SEQ ID NO: 22
2H8; CDRH2: NTETGE

SEQ ID NO: 23
2H8; CDRH3: YYGYFDY

SEQ ID NO: 24
2H8; CDRL1: RASESVDSYGNSFMH

SEQ ID NO: 25
2H8; CDRL2: RASNLES,
and

SEQ ID NO: 26
2H8; CDRL3: QQSNEDPWT
```

In some cases, anti-IL1-RAP antibodies can comprise one or more 2H8 CDRs that contain 1, 2, 3, or 4 amino acid substitutions or deletions as compared to a CDR selected from the group consisting of:

```
                                SEQ ID NO: 21
2H8; CDRH1: GYTFTDYSMH

SEQ ID NO: 22
2H8; CDRH2: NTETGE

SEQ ID NO: 23
2H8; CDRH3: YYGYFDY

SEQ ID NO: 24
2H8; CDRL1: RASESVDSYGNSFMH

SEQ ID NO: 25
2H8; CDRL2: RASNLES,
and

SEQ ID NO: 26
2H8; CDRL3: QQSNEDPWT
```

In some cases, anti-IL1-RAP antibodies can comprise light chain variable region sequence and/or the heavy chain variable region sequence of the clone 50.3G7.

```
50.3G7 light chain variable region sequence:
                                SEQ ID NO: 27
DIVLTQSPATLSVTPGDSVSLSCRASQSISNNLHWYQQKSHESPRLLIKY

ASQSISGIPSRFSGSGSGTDFTLSINSVETEDFGVYFCQQSHNWPHTFGG

GTKLEIKR 50.3G7 heavy chain variable region sequence:
                                SEQ ID NO: 134
QIQLVQSGPELKKPGETVKISCKASGYTFTNYGMHWVKQSPGEGLKWMGW

INTYTGEPTYADDFKGRFGFSLETSASSAYLQINDLKNEDMATYFCARYY

GNFDYWGQGTTLTVSS 50.3G7 humanized light chain variable region
sequence variant 1:
                                SEQ ID NO: 122
EIVMTQSPATLSVSPGERATLSCRASQSISNNLHWYQQKPGQAPRLLIYY

ASQSISGIPARFSGSGSGTEFTLTISSLQSEDFAVYYCQQSHNWPHTFGQ

GTKLEIKR
```

50.3G7 humanized heavy chain variable region sequence variant 1:
SEQ ID NO: 123
EVQLVQSGAEVKKPGASVKISCKASGYTFTNYGMHWVRQAPGQGLEWMGW

INTYTGEPTYAQKFQGRFTFTLDTSTSTAYLEIRSLRSDDTAVYYCARYY

GNFDYWGQGTLLTVSS

In other cases, anti-IL1-RAP antibodies can comprise a 50.3G7 light chain variable region that is at least 85%, 90%, 95%, 97%, 98%, or 99% identical to SEQ ID NO: 27. Additionally, or in the alternative, anti-IL1-RAP antibodies can comprise a 50.3G7 heavy chain variable region that is at least 85%, 90%, 95%, 96% 97%, 98%, or 99% identical to SEQ ID NO: 134.

In some cases, anti-IL1-RAP antibodies can comprise one or more 50.3G7 CDRs that are 95%, 96%, 97%, 98%, 99%, or 100% identical to the CDRs selected from the group consisting of:

```
                               SEQ ID NO: 29
50.3G7; CDRH1: GYTFTNY

SEQ ID NO: 30
50.3G7; CDRH2: NTYTGE

SEQ ID NO: 31
50.3G7; CDRH3: YYGNFDY

SEQ ID NO: 32
50.3G7; CDRL1: RASQSISNNLH

SEQ ID NO: 33
50.3G7; CDRL2: YASQSIS,
and

SEQ ID NO: 34
50.3G7; CDRL3: QQSHNWPHT
```

In some cases, anti-IL1-RAP antibodies can comprise one or more 50.3G7 CDRs that contain 1, 2, 3, or 4 amino acid substitutions or deletions as compared to a CDR selected from the group consisting of:

```
                               SEQ ID NO: 29
50.3G7; CDRH1: GYTFTNY

SEQ ID NO: 30
50.3G7; CDRH2: NTYTGE

SEQ ID NO: 31
50.3G7; CDRH3: YYGNFDY

SEQ ID NO: 32
50.3G7; CDRL1: RASQSISNNLH

SEQ ID NO: 33
50.3G7; CDRL2: YASQSIS,
and

SEQ ID NO: 34
50.3G7; CDRL3: QQSHNWPHT
```

In some embodiments, the anti-IL1RAP antibody is a humanized 50.3G7 antibody having a light chain sequence that is 95%, 96%, 97%, 98%, 99%, or 100% identical to the sequence of SEQ ID NO: 124:

EIVMTQSPATLSVSPGERATLSCRASQSISNNLHWYQQKPGQAPRLLIYY

ASQSISGIPARFSGSGSGTEFTLTISSLQSEDFAVYYCQQSHNWPHTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC (SEQ ID NO: 124; CDRsand a cysteine substitution for conjugation are in bold and underline; CDR SEQ ID NOS: 32,33 and 34, respectively).

In some embodiments, the anti-IL1RAP antibody is a humanized 50.3G7 antibody having a heavy chain sequence that is 95%, 96%, 97%, 98%, 99%, or 100% identical to the sequence of SEQ ID NO: 125:

EVQLVQSGAEVKKPGASVKISCKASGYTFTNYGMHWVRQAPGQGLEWMGW

INTYTGEPTYAQKFQGRFTFTLDTSTSTAYLEIRSLRSDDTAVYYCARYY

GNFDYWGQGTLLTVSSASTKGPSVFPLAPSSKSTSGGTAALGCLVKDYFP

EPVTVCWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG (SEQ

ID NO: 125; CDRs and a cysteine substitution for conjugation are in bold and underline; CDR SEQ ID NOS: 132, 133 and 31, respectively).

In some cases, anti-IL1-RAP antibodies can comprise light chain variable region sequence and/or the heavy chain variable region sequence of the clone 54.15B5.

54.15B5 light chain variable region sequence:
SEQ ID NO: 128
QIVLTQSPAIMSASPGEKVTMTCSASSSISYIHWYRQKPGTSPKRWIYDT

SNLASGVPARFSGSGSGTSYSLTIINMEAEDAATYYCHQRTYYPLTFGGG

TRLELK 54.15B5 heavy chain variable region sequence:
SEQ ID NO: 129
KWSWWSLGGGLAKPGGSLKLSCTASGFTFTSYVMSWVRQSPEKRLEWVAE

ISRGGSHTYYSDTVTGRFTISRDNANNALYLEMSSVRSADTAMYFCTRAY

GNSEMDFWGQGTSVTSS

In other cases, anti-IL1-RAP antibodies can comprise a 54.15B5 light chain variable region that is at least 85%, 90%, 95%, 97%, 98%, or 99% identical to SEQ ID NO: 128. Additionally, or in the alternative, anti-IL1-RAP antibodies can comprise a 54.15B5 heavy chain variable region that is at least 85%, 90%, 95%, 96% 97%, 98%, or 99% identical to SEQ ID NO: 129.

In some cases, anti-IL1-RAP antibodies can comprise one or more 54.15B5 CDRs that are 95%, 96%, 97%, 98%, 99%, or 100% identical to the CDRs selected from the group consisting of:

```
                                     SEQ ID NO: 35
    54.15B5; CDRH1: GFTFTSY

SEQ ID NO: 36
    54.15B5; CDRH2: SRGGSH

SEQ ID NO: 37
    54.15B5; CDRH3: AYGNSEMDF

SEQ ID NO: 38
    54.15B5; CDRL1: SASSSISYIH

SEQ ID NO: 39
    54.15B5; CDRL2: DTSNLAS,
    and

SEQ ID NO: 40
    54.15B5; CDRL3: HQRTYYPLT
```

In some cases, anti-IL1-RAP antibodies can comprise one or more 54.15B5 CDRs that contain 1, 2, 3, or 4 amino acid substitutions or deletions as compared to a CDR selected from the group consisting of:

```
                                     SEQ ID NO: 35
    54.15B5; CDRH1: GFTFTSY

SEQ ID NO: 36
    54.15B5; CDRH2: SRGGSH

SEQ ID NO: 37
    54.15B5; CDRH3: AYGNSEMDF

SEQ ID NO: 38
    54.15B5; CDRL1: SASSSISYIH

SEQ ID NO: 39
    54.15B5; CDRL2: DTSNLAS,
    and

SEQ ID NO: 40
    54.15B5; CDRL3: HQRTYYPLT
```

In some cases, anti-IL1-RAP antibodies can comprise light chain variable region sequence and/or the heavy chain variable region sequence of the clone 42.1D3.

```
42.1D3 light chain variable region sequence:
                                     SEQ ID NO: 41
DIVLTQSPATLSVTPGDSVSLSCRASQSINNDLHWYQQKSHESPRLLIKY

ASQSISGIPSRFSGSGSGTDFTLRINSVETEDFRMYFCQQSNNWPLTFGA

GTKLEVK 42.1D3 heavy chain variable region sequence:
                                     SEQ ID NO: 42
QIQLVQSGPELKKPGETVNISCKASGYTFTDFSMHWVKQAPGKGLQWMGW

INTETGEPTYADDFEARFAFSLATSANTAYLKINNLKNEDTATYFCARFF

LHFDYWGQGTTLTVSS
```

In other cases, anti-IL1-RAP antibodies can comprise a 42.1D3 light chain variable region that is at least 85%, 90%, 95%, 97%, 98%, or 99% identical to SEQ ID NO: 41. Additionally, or in the alternative, anti-IL1-RAP antibodies can comprise a 42.1D3 heavy chain variable region that is at least 85%, 90%, 95%, 96% 97%, 98%, or 99% identical to SEQ ID NO: 42.

In some cases, anti-IL1-RAP antibodies can comprise one or more 42.1D3 CDRs that are 95%, 96%, 97%, 98%, 99%, or 100% identical to the CDRs selected from the group consisting of:

```
                                     SEQ ID NO: 43
    42.1D3; CDRH1: GYTFTDF

SEQ ID NO: 22
    42.1D3; CDRH2: NTETGE

SEQ ID NO: 44
    42.1D3; CDRH3: FFLHFDY

SEQ ID NO: 45
    42.1D3; CDRL1: RASQSINNDLH

SEQ ID NO: 33
    42.1D3; CDRL2: YASQSIS,
    and

SEQ ID NO: 46
    42.1D3; CDRL3: QQSNNWPLT
```

In some cases, anti-IL1-RAP antibodies can comprise one or more 42.1D3 CDRs that contain 1, 2, 3, or 4 amino acid substitutions or deletions as compared to a CDR selected from the group consisting of:

```
                                     SEQ ID NO: 43
    42.1D3; CDRH1: GYTFTDF

SEQ ID NO: 22
    42.1D3; CDRH2: NTETGE

SEQ ID NO: 44
    42.1D3; CDRH3: FFLHFDY

SEQ ID NO: 45
    42.1D3; CDRL1: RASQSINNDLH

SEQ ID NO: 33
    42.1D3; CDRL2: YASQSIS,
    and

SEQ ID NO: 46
    42.1D3; CDRL3: QQSNNWPLT
```

In some cases, anti-IL1-RAP antibodies can comprise light chain variable region sequence and/or the heavy chain variable region sequence of the clone 54.8H8.

```
54.8H8 light chain variable region sequence:
                                     SEQ ID NO: 130
QIVLTQSPAIMSASPGEKVTMTCSASSSVIYIYWFQQKPGSSPRLLIYDT

SNLASGVPLRFSGSGSGTSYSLTISRMETEDVSTYYCQQWNSYPPTFGGG

TKLEIK 54.8H8 heavy chain variable region sequence:
                                     SEQ ID NO: 131
EVQLVESGGGLVKPGGSLKLSCAASGFSFSSYGMSWVRQSPEKRLEWVAE

ITSGGSHTYYPDTVTGRFTISRDNAKNTLYLEMSSLRSEDTAMYYCSRSY

GNYVMDYWGQGTSVTVSS
```

In other cases, anti-IL1-RAP antibodies can comprise a 54.8H8 light chain variable region that is at least 85%, 90%, 95%, 97%, 98%, or 99% identical to SEQ ID NO: 130 Additionally, or in the alternative, anti-IL1-RAP antibodies can comprise a 54.8H8 heavy chain variable region that is at least 85%, 90%, 95%, 96% 97%, 98%, or 99% identical to SEQ ID NO: 131.

In some cases, anti-IL1-RAP antibodies can comprise one or more 54.8H8 CDRs that are 95%, 96%, 97%, 98%, 99%, or 100% identical to the CDRs selected from the group consisting of:

```
                                      SEQ ID NO: 47
    54.8H8; CDRH1: GFSFSSYG

SEQ ID NO: 48
    54.8H8; CDRH2: TSGGSH

SEQ ID NO: 49
    54.8H8; CDRH3: SYGNYVMDY

SEQ ID NO: 50
    54.8H8; CDRL1: SASSSVIYIY

SEQ ID NO: 39
    54.8H8; CDRL2: DTSNLAS,
    and

SEQ ID NO: 51
    54.8H8; CDRL3: QQWNSYPPT
```

In some cases, anti-IL1-RAP antibodies can comprise one or more 54.8H8 CDRs that contain 1, 2, 3, or 4 amino acid substitutions or deletions as compared to a CDR selected from the group consisting of:

```
                                      SEQ ID NO: 47
    54.8H8; CDRH1: GFSFSSYG

SEQ ID NO: 48
    54.8H8; CDRH2: TSGGSH

SEQ ID NO: 49
    54.8H8; CDRH3: SYGNYVMDY

SEQ ID NO: 50
    54.8H8; CDRL1: SASSSVIYIY

SEQ ID NO: 39
    54.8H8; CDRL2: DTSNLAS,
    and

SEQ ID NO: 51
    54.8H8; CDRL3: QQWNSYPPT
```

In some cases, anti-IL1-RAP antibodies can comprise light chain variable region sequence and/or the heavy chain variable region sequence of the clone 54.9E9.

```
54.9E9 light chain variable region sequence:
                                      SEQ ID NO: 52
QIVLTQSPAIMSASPGEKVTMTCSASSSVSYMHWYQQKTGTSPKRLIYDT

SKLASGVPARFSGSGSGTSYSLTISSMEAEDAATYYCHQRSYYPLTFGAG

AKLELK 54.9E9 heavy chain variable region sequence:
                                      SEQ ID NO: 53
QIQLVQSGPELKKPGETVKISCKASSYTFTDYSMHWVKQAPGKGLKWMGW

INTETGEPRYADDFKGRFAFSLETSASTAYLQINNLKNEDTATYFCARFL

LHFDYWGQGTILTVSS
```

In other cases, anti-IL1-RAP antibodies can comprise a 54.9E9 light chain variable region that is at least 85%, 90%, 95%, 97%, 98%, or 99% identical to SEQ ID NO: 52. Additionally, or in the alternative, anti-IL1-RAP antibodies can comprise a 54.9E9 heavy chain variable region that is at least 85%, 90%, 95%, 96% 97%, 98%, or 99% identical to SEQ ID NO: 53.

In some cases, anti-IL1-RAP antibodies can comprise one or more 54.9E9 CDRs that are 95%, 96%, 97%, 98%, 99%, or 100% identical to the CDRs selected from the group consisting of:

```
                                      SEQ ID NO: 54
    54.9E9; CDRH1: SYTFTDY

SEQ ID NO: 22
    54.9E9; CDRH2: NTETGE

SEQ ID NO: 55
    54.9E9; CDRH3: FLLHFDY

SEQ ID NO: 56
    54.9E9; CDRL1: SASSSVSYMH

SEQ ID NO: 19
    54.9E9; CDRL2: DTSKLAS,
    and

SEQ ID NO: 57
    54.9E9; CDRL3: HQRSYYPLT
```

In some cases, anti-IL1-RAP antibodies can comprise one or more 54.9E9 CDRs that contain 1, 2, 3, or 4 amino acid substitutions or deletions as compared to a CDR selected from the group consisting of:

```
                                      SEQ ID NO: 54
    54.9E9; CDRH1: SYTFTDY

SEQ ID NO: 22
    54.9E9; CDRH2: NTETGE

SEQ ID NO: 55
    54.9E9; CDRH3: FLLHFDY

SEQ ID NO: 56
    54.9E9; CDRL1: SASSSVSYMH

SEQ ID NO: 19
    54.9E9; CDRL2: DTSKLAS,
    and

SEQ ID NO: 57
    54.9E9; CDRL3: HQRSYYPLT
```

In some cases, anti-IL1-RAP antibodies can comprise light chain variable region sequence and/or the heavy chain variable region sequence of the clone 50.6C12.

```
50.6C12 light chain variable region sequence:
                                      SEQ ID NO: 58
DIQMTQSPASLSASVGETVTITCRASGNIHNYLAWYQQKQGKSPHLLVYN

AETLADGVPSRFSGSGSGTQYSLKINSLQPEDFGTYYCQHFWSTPWTFGG

GTKLEIK 50.6C12 heavy chain variable region sequence:
                                      SEQ ID NO: 59
EVQLQQSGPELVKPGDSVKMSCKASGYTFTDYYMDWVKQSHGKSLEWIGY

IYPHNGGTTYNQKFKGKATLTVDKSSSTAYMELHSLTSEDSAVYYCARSP

FNYKDPMDWWGQGTSVTSS
```

In other cases, anti-IL1-RAP antibodies can comprise a 50.6C12 light chain variable region that is at least 85%, 90%, 95%, 97%, 98%, or 99% identical to SEQ ID NO: 58. Additionally, or in the alternative, anti-IL1-RAP antibodies can comprise a 50.6C12 heavy chain variable region that is at least 85%, 90%, 95%, 96% 97%, 98%, or 99% identical to SEQ ID NO: 59.

In some cases, anti-IL1-RAP antibodies can comprise one or more 50.6C12 CDRs that are 95%, 96%, 97%, 98%, 99%, or 100% identical to the CDRs selected from the group consisting of:

```
                                    SEQ ID NO: 60
50.6C12; CDRH1: GYTFTDY

SEQ ID NO: 61
50.6C12; CDRH2: YPHNGG

SEQ ID NO: 62
50.6C12; CDRH3: SPFNYKDPMDW

SEQ ID NO: 63
50.6C12; CDRL1: RASGNIHNYLA

SEQ ID NO: 64
50.6C12; CDRL2: NAETLAD,
and

SEQ ID NO: 65
50.6C12; CDRL3: QHFWSTPWT
```

In some cases, anti-IL1-RAP antibodies can comprise one or more 50.6C12 CDRs that contain 1, 2, 3, or 4 amino acid substitutions or deletions as compared to a CDR selected from the group consisting of:

```
                                    SEQ ID NO: 60
50.6C12; CDRH1: GYTFTDY

SEQ ID NO: 61
50.6C12; CDRH2: YPHNGG

SEQ ID NO: 62
50.6C12; CDRH3: SPFNYKDPMDW

SEQ ID NO: 63
50.6C12; CDRL1: RASGNIHNYLA

SEQ ID NO: 64
50.6C12; CDRL2: NAETLAD,
and

SEQ ID NO: 65
50.6C12; CDRL3: QHFWSTPWT
```

In some cases, anti-IL1-RAP antibodies can comprise light chain variable region sequence and/or the heavy chain variable region sequence of the clone 57.7A9.

```
57.7A9 light chain variable region sequence:
                                    SEQ ID NO: 66
QVQLQQPGAELVKPGASVTLSCEASGYTFTSYWIHWVKQRPGQGLEWIGE

INPSHGHTTYNEKFKNKATLTVDKSSSTAYMQVSSLTSEDSAVYYCTRHY

GSYYFDLWGQGTTLTVSS 57.7A9 heavy chain variable region sequence:
                                    SEQ ID NO: 59
EVQLQQSGPELVKPGDSVKMSCKASGYTFTDYYMDWVKQSHGKSLEWIGY

IYPHNGGTTYNQKFKGKATLTVDKSSSTAYMELHSLTSEDSAVYYCARSP

FNYKDPMDWWGQGTSVTVSS
```

In other cases, anti-IL1-RAP antibodies can comprise a 57.7A9 light chain variable region that is at least 85%, 90%, 95%, 97%, 98%, or 99% identical to SEQ ID NO: 13. Additionally, or in the alternative, anti-IL1-RAP antibodies can comprise a 57.7A9 heavy chain variable region that is at least 85%, 90%, 95%, 96% 97%, 98%, or 99% identical to SEQ ID NO: 66.

In some cases, anti-IL1-RAP antibodies can comprise one or more 57.7A9 CDRs that are 95%, 96%, 97%, 98%, 99%, or 100% identical to the CDRs selected from the group consisting of:

```
                                    SEQ ID NO: 15
57.7A9; CDRH1: GYTFTSY

SEQ ID NO: 16
57.7A9; CDRH2: NPSHGH

SEQ ID NO: 17
57.7A9; CDRH3: HYGSYYFDL

SEQ ID NO: 18
57.7A9; CDRL1: RASSSVSYMH

SEQ ID NO: 19
57.7A9; CDRL2: DTSKLAS,
and

SEQ ID NO: 20
57.7A9; CDRL3: QQWSTNPIT
```

In some cases, anti-IL1-RAP antibodies can comprise one or more 57.7A9 CDRs that contain 1, 2, 3, or 4 amino acid substitutions or deletions as compared to a CDR selected from the group consisting of:

```
                                    SEQ ID NO: 15
57.7A9; CDRH1: GYTFTSY

SEQ ID NO: 16
57.7A9; CDRH2: NPSHGH

SEQ ID NO: 17
57.7A9; CDRH3: HYGSYYFDL

SEQ ID NO: 18
57.7A9; CDRL1: RASSSVSYMH

SEQ ID NO: 19
57.7A9; CDRL2: DTSKLAS,
and

SEQ ID NO: 20
57.7A9; CDRL3: QQWSTNPIT
```

In some cases, anti-IL1-RAP antibodies can comprise light chain variable region sequence and/or the heavy chain variable region sequence of the clone 46.8G1.

```
46.8G1 light chain variable region sequence:
                                    SEQ ID NO: 67
DIQMTQSPASLSVSVGETVTITCRASENIYSNLVWYQQKQGKSPQLLVYA

ATNLADGVPSRFSGSGSDTQYSLKINSLQSEDFGSYYCLHFWGPPYMYTF

GGGTNLEMKR 46.8G1 heavy chain variable region sequence:
                                    SEQ ID NO: 68
QVQLQQSGPELVKPGASVKISCTASGYAFSTSWMNWVKQRPGKGLEWIGR

IYPGDGDSNYNGKFKGKATLTADKSSSTAYMQLSSLTSEDSAVYFCARRD

YYGFFDVWGAGTTVTVSS
```

In other cases, anti-IL1-RAP antibodies can comprise a 46.8G1 light chain variable region that is at least 85%, 90%, 95%, 97%, 98%, or 99% identical to SEQ ID NO: 67. Additionally, or in the alternative, anti-IL1-RAP antibodies can comprise a 46.8G1 heavy chain variable region that is at least 85%, 90%, 95%, 96% 97%, 98%, or 99% identical to SEQ ID NO: 68.

In some cases, anti-IL1-RAP antibodies can comprise one or more 46.8G1 CDRs that are 95%, 96%, 97%, 98%, 99%, or 100% identical to the CDRs selected from the group consisting of:

```
                                 SEQ ID NO: 69
    46.8G1; CDRH1: GYAFSTS

SEQ ID NO: 70
    46.8G1; CDRH2: YPGDGD

SEQ ID NO: 71
    46.8G1; CDRH3: RDYYGFFDV

SEQ ID NO: 72
    46.8G1; CDRL1: RASENIYSNLV

SEQ ID NO: 73
    46.8G1; CDRL2: AATNLAD,
    and

SEQ ID NO: 74
    46.8G1; CDRL3: LHFWGPPYMYT
```

In some cases, anti-IL1-RAP antibodies can comprise one or more 46.8G1CDRs that contain 1, 2, 3, or 4 amino acid substitutions or deletions as compared to a CDR selected from the group consisting of:

```
                                 SEQ ID NO: 69
    46.8G1; CDRH1: GYAFSTS

SEQ ID NO: 70
    46.8G1; CDRH2: YPGDGD

SEQ ID NO: 71
    46.8G1; CDRH3: RDYYGFFDV

SEQ ID NO: 72
    46.8G1; CDRL1: RASENIYSNLV

SEQ ID NO: 73
    46.8G1; CDRL2: AATNLAD,
    and

SEQ ID NO: 74
    46.8G1; CDRL3: LHFWGPPYMYT
```

In some cases, anti-IL1-RAP antibodies can comprise light chain variable region sequence and/or the heavy chain variable region sequence of the clone 42.3G6.

```
42.3G6 light chain variable region sequence:
                                 SEQ ID NO: 75
DIVMTQAAFSNPVTLGTSASISCRSSKSLLHSNGITYLYWYLQKPGQSPQ

LLIYQMSNLASGVPDRFSSSGSGTDFTLRISRVEAEDVGVYYCAQNLELP

FTFGSGTKLEIK 42.3G6 heavy chain variable region sequence:
                                 SEQ ID NO: 76
QIQLVQSGPELKKPGETVKISCKASGYTFTDYSMHWVKQAPEKGLKWMGW

INTETGEPTYADDFKGRFAFSLETSASTAYLQINNLKNEDTATYFCARGS

FPWFTYWGQGTLVTVSA
```

In other cases, anti-IL1-RAP antibodies can comprise a 42.3G6 light chain variable region that is at least 85%, 90%, 95%, 97%, 98%, or 99% identical to SEQ ID NO: 75. Additionally, or in the alternative, anti-IL1-RAP antibodies can comprise a 42.3G6 heavy chain variable region that is at least 85%, 90%, 95%, 96% 97%, 98%, or 99% identical to SEQ ID NO: 76.

In some cases, anti-IL1-RAP antibodies can comprise one or more 42.3G6 CDRs that are 95%, 96%, 97%, 98%, 99%, or 100% identical to the CDRs selected from the group consisting of:

```
                                 SEQ ID NO: 60
    42.3G6; CDRH1: GYTFTDY

SEQ ID NO: 22
    42.3G6; CDRH2: NTETGE

SEQ ID NO: 77
    42.3G6; CDRH3: GSFPWFTY

SEQ ID NO: 78
    42.3G6; CDRL1: RSSKSLLHSNGITYLY

SEQ ID NO: 79
    42.3G6; CDRL2: QMSNLAS,
    and

SEQ ID NO: 80
    42.3G6; CDRL3: AQNLELPFT
```

In some cases, anti-IL1-RAP antibodies can comprise one or more 42.3G6 CDRs that contain 1, 2, 3, or 4 amino acid substitutions or deletions as compared to a CDR selected from the group consisting of:

```
                                 SEQ ID NO: 60
    42.3G6; CDRH1: GYTFTDY

SEQ ID NO: 22
    42.3G6; CDRH2: NTETGE

SEQ ID NO: 77
    42.3G6; CDRH3: GSFPWFTY

SEQ ID NO: 78
    42.3G6; CDRL1: RSSKSLLHSNGITYLY

SEQ ID NO: 79
    42.3G6; CDRL2: QMSNLAS,
    and

SEQ ID NO: 80
    42.3G6; CDRL3: AQNLELPFT
```

In some cases, anti-IL1-RAP antibodies can comprise light chain variable region sequence and/or the heavy chain variable region sequence of the clone 46.1D2.

```
46.1D2 light chain variable region sequence:
                                 SEQ ID NO: 81
DIQMTQTTSSLSASLGDRVTISCSASQGISNYLNWYQQKPDGSVKLLIYY

TSTLHSGVPSRFSGSGSGTDYSLTISNLEPEDIATYYCQQYSYLPWTFGG

GTKLEIK 46.1D2 heavy chain variable region sequence:
                                 SEQ ID NO: 82
QVQLQQSGPELVKPGASVKISCKASGYGFSSSWMNWVKQRPGKGLEWIGR

IYPGDGNTNYYGEFKGKATLTADKSSSTAYMQLNSLTSEDSAVYFCARND

GYPAWFTYWGQGTLVTVSA
```

In other cases, anti-IL1-RAP antibodies can comprise a 46.1D2 light chain variable region that is at least 85%, 90%, 95%, 97%, 98%, or 99% identical to SEQ ID NO: 81. Additionally, or in the alternative, anti-IL1-RAP antibodies can comprise a 46.1D2 heavy chain variable region that is at least 85%, 90%, 95%, 96% 97%, 98%, or 99% identical to SEQ ID NO: 82.

In some cases, anti-IL1-RAP antibodies can comprise one or more 46.1D2 CDRs that are 95%, 96%, 97%, 98%, 99%, or 100% identical to the CDRs selected from the group consisting of:

```
                                      SEQ ID NO: 83
46.1D2; CDRH1: GYGFSSS

SEQ ID NO: 84
46.1D2; CDRH2: YPGDGN

SEQ ID NO: 85
46.1D2; CDRH3: NDGYPAWFTY

SEQ ID NO: 86
46.1D2; CDRL1: SASQGISNYLN

SEQ ID NO: 87
46.1D2; CDRL2: YTSTLHS, and

SEQ ID NO: 88
46.1D2; CDRL3: QQYSYLPWT
```

In some cases, anti-IL1-RAP antibodies can comprise one or more 46.1D2 CDRs that contain 1, 2, 3, or 4 amino acid substitutions or deletions as compared to a CDR selected from the group consisting of:

```
                                      SEQ ID NO: 83
46.1D2; CDRH1: GYGFSSS

SEQ ID NO: 84
46.1D2; CDRH2: YPGDGN

SEQ ID NO: 85
46.1D2; CDRH3: NDGYPAWFTY

SEQ ID NO: 86
46.1D2; CDRL1: SASQGISNYLN

SEQ ID NO: 87
46.1D2; CDRL2: YTSTLHS, and

SEQ ID NO: 88
46.1D2; CDRL3: QQYSYLPWT
```

In some cases, anti-IL1-RAP antibodies can comprise light chain variable region sequence and/or the heavy chain variable region sequence of the clone 41.10C2.

```
41.10C2 light chain variable region sequence:
                                      SEQ ID NO: 89
DSVLTQSLTSLVVSLGQRATISCRASESVDNHGNSFMHWYQQKPGQPPKL LIFLASNLESGIPARFSGSGSRTDFTLTINPVEGDEGATYYCHQINaHPY

TFGGGTKLEIKR 41.10C2 heavy chain variable region sequence:
                                      SEQ ID NO: 90
QVTLKESGPGILQPSQTLSLTCSFSGFSLSTFGVGVGWIRQPSGKGLEWL

AHIWWDDDKYYKSALKSRLTISKDTSKNQVFLKIANVDTADTATYFCARL

KLGPYYFDYWGQGTTLTVSS
```

In other cases, anti-IL1-RAP antibodies can comprise a 41.10C2 light chain variable region that is at least 85%, 90%, 95%, 97%, 98%, or 99% identical to SEQ ID NO: 89. Additionally, or in the alternative, anti-IL1-RAP antibodies can comprise a 41.10C2 heavy chain variable region that is at least 85%, 90%, 95%, 96% 97%, 98%, or 99% identical to SEQ ID NO: 90.

In some cases, anti-IL1-RAP antibodies can comprise one or more 41.10C2 CDRs that are 95%, 96%, 97%, 98%, 99%, or 100% identical to the CDRs selected from the group consisting of:

```
                                      SEQ ID NO: 91
46.1D2; CDRH1: GFSLSTFGV

SEQ ID NO: 92
46.1D2; CDRH2: WWDDD

SEQ ID NO: 93
46.1D2; CDRH3: LKLGPYYFDY

SEQ ID NO: 94
46.1D2; CDRL1: RASESVDNHGNSFMH

SEQ ID NO: 95
46.1D2; CDRL2: LASNLES, and

SEQ ID NO: 96
46.1D2; CDRL3: HQINAHPYT
```

In some cases, anti-IL1-RAP antibodies can comprise one or more 41.10C2 CDRs that contain 1, 2, 3, or 4 amino acid substitutions or deletions as compared to a CDR selected from the group consisting of:

```
                                      SEQ ID NO: 91
46.1D2; CDRH1: GFSLSTFGV

SEQ ID NO: 92
46.1D2; CDRH2: WWDDD

SEQ ID NO: 93
46.1D2; CDRH3: LKLGPYYFDY

SEQ ID NO: 94
46.1D2; CDRL1: RASESVDNHGNSFMH

SEQ ID NO: 95
46.1D2; CDRL2: LASNLES, and

SEQ ID NO: 96
46.1D2; CDRL3: HQINAHPYT
```

In some cases, anti-IL1-RAP antibodies can comprise light chain variable region sequence and/or the heavy chain variable region sequence of the clone 46.2C2.

```
46.2C2 light chain variable region sequence:
                                      SEQ ID NO: 97
QIVLTQSPAIMSASPGEKVTMTCSARSSVDYMYWYQQKPGSSPRLLIYAT

SNLASGVPVRFSGSGSGTSYSLTIVRVEAEDAATYYCQQWNTYPLTFGAG

TKLELK 46.2C2 heavy chain variable region sequence:
                                      SEQ ID NO: 98
DVKLVESGGGLVKLGGSLKLSCAASGFTFSSYYMSWVRQTPEKRLEWVAT

ISNSGGSTYYADSVKDRFTISRDSAKNTLYLQMNSLISEDTAVYYCALYY

GNFGFDYWGQGTSLTVSS
```

In other cases, anti-IL1-RAP antibodies can comprise a 46.2C2 light chain variable region that is at least 85%, 90%, 95%, 97%, 98%, or 99% identical to SEQ ID NO: 97. Additionally, or in the alternative, anti-IL1-RAP antibodies can comprise a 46.2C2 heavy chain variable region that is at least 85%, 90%, 95%, 96% 97%, 98%, or 99% identical to SEQ ID NO: 98.

In some cases, anti-IL1-RAP antibodies can comprise one or more 46.2C2 CDRs that are 95%, 96%, 97%, 98%, 99%, or 100% identical to the CDRs selected from the group consisting of:

```
                                    SEQ ID NO: 99
46.2C2; CDRH1: GFTFSSY

SEQ ID NO: 100
46.2C2; CDRH2: SNSGGS

SEQ ID NO: 101
46.2C2; CDRH3: YYGNFGFDY

SEQ ID NO: 102
46.2C2; CDRL1: SARSSVDYMY

SEQ ID NO: 103
46.2C2; CDRL2: ATSNLAS, and

SEQ ID NO: 104
46.2C2; CDRL3: QQWNTYPLT
```

In some cases, anti-IL1-RAP antibodies can comprise one or more 46.2C2 CDRs that contain 1, 2, 3, or 4 amino acid substitutions or deletions as compared to a CDR selected from the group consisting of:

```
                                    SEQ ID NO: 99
46.2C2; CDRH1: GFTFSSY

SEQ ID NO: 100
46.2C2; CDRH2: SNSGGS

SEQ ID NO: 101
46.2C2; CDRH3: YYGNFGFDY

SEQ ID NO: 102
46.2C2; CDRL1: SARSSVDYMY

SEQ ID NO: 103
46.2C2; CDRL2: ATSNLAS, and

SEQ ID NO: 104
46.2C2; CDRL3: QQWNTYPLT
```

In some cases, anti-IL1-RAP antibodies can comprise light chain variable region sequence and/or the heavy chain variable region sequence of the clone 44.5D2.

```
44.5D2 light chain variable region sequence:
                                    SEQ ID NO: 105
DIVMTQSHKFMSTSVGDRVSITCKASQDVGTAVAWYQQKSGQSPKLLIYW

ASTRHTEVPDRFTGSGSGTDFTLTISNVQSEDLTDYFCQQYSSYPLYTFG

GGTKLEIKR 44.5D2 heavy chain variable region sequence:
                                    SEQ ID NO: 106
TVVDSGKCRSKGFGYTLGGCGVLWSKQRPGQGLEWIGEINPSNGFTNYNE

KFNYKATLTVDKSSSTAYMQLSSLTSADSAVYYCTTGGHYFDYWGQGTTL

TVSS
```

In other cases, anti-IL1-RAP antibodies can comprise a 44.5D2 light chain variable region that is at least 85%, 90%, 95%, 97%, 98%, or 99% identical to SEQ ID NO: 105. Additionally, or in the alternative, anti-IL1-RAP antibodies can comprise a 44.5D2 heavy chain variable region that is at least 85%, 90%, 95%, 96% 97%, 98%, or 99% identical to SEQ ID NO: 106.

In some cases, anti-IL1-RAP antibodies can comprise one or more 44.5D2 CDRs that are 95%, 96%, 97%, 98%, 99%, or 100% identical to the CDRs selected from the group consisting of:

```
                                    SEQ ID NO: 107
44.5D2; CDRH1: GYTLGGC

SEQ ID NO: 108
44.5D2; CDRH2: NPSNGF

SEQ ID NO: 109
44.5D2; CDRH3: GGHYFDY

SEQ ID NO: 110
44.5D2; CDRL1: KASQDVGTAVA

SEQ ID NO: 111
44.5D2; CDRL2: WASTRHT, and

SEQ ID NO: 112
44.5D2; CDRL3: QQYSSYPLYT
```

In some cases, anti-IL1-RAP antibodies can comprise one or more 44.5D2 CDRs that contain 1, 2, 3, or 4 amino acid substitutions or deletions as compared to a CDR selected from the group consisting of:

```
                                    SEQ ID NO: 107
44.5D2; CDRH1: GYTLGGC

SEQ ID NO: 108
44.5D2; CDRH2: NPSNGF

SEQ ID NO: 109
44.5D2; CDRH3: GGHYFDY

SEQ ID NO: 110
44.5D2; CDRL1: KASQDVGTAVA

SEQ ID NO: 111
44.5D2; CDRL2: WASTRHT, and

SEQ ID NO: 112
44.5D2; CDRL3: QQYSSYPLYT
```

Any of the antibodies described herein can be a chimeric antibody or a humanized antibody. In some embodiments, the antibody is an anti-IL1-RAP-binding antibody fragment, e.g., an Fab. In some embodiments, the anti-IL1-RAP antibody is labeled with a detectable agent, e.g., as described below. In some embodiments, the anti-IL1-RAP antibody is attached to a therapeutic agent, e.g., a chemotherapeutic or cytotoxic agent as described below.

In other embodiments, the anti-IL1-RAP antibody is a bi-specific antibody having a first arm having an antigen binding region that binds receptor IL1RAP, and a second arm having an antigen binding region that binds a second target antigen. The second target antigen can be any antigen of interest. For example, the second target antigen can be a cancer marker, i.e., a protein that is expressed at higher levels (e.g., more than 2×) on cancer cells (e.g., a cell surface protein) than on non-cancer cells. For example, the second target antigen can be selected from CLL-1, GPR114, IL1RAP, TIM-3, CD19, CD20, CD22, ROR1, mesothelin, CD33, CD123/IL3Ra, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmel-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Crypto, CD30, MUC16, GPNMB, BCMA, Trop-2, Tissue Factor (TF), CanAg, EGFR, αv-integrin, CD37, Folate Receptor, CD138, CEACAMS, CD56, CD70, CD74, GCC, 5T4, CD79b, Steap1, Napi2b, Lewis Y Antigen, LIV, c-RET, DLL3, EFNA4, Ly6e (RIG-e), CD79a, CD274 (PD-L1), CD38, DLL4, CD319 (SLAMF7) or Endosialin/CD248

In some embodiments, the antibody also has at least one activity selected from

Binding to the receptor form of IL1-RAP with a $K_D$ of 100 µM or lower (e.g., 1-10 µM, 0.1-10 µM, 10-50 µM, about 20 µM, etc.);

Binding to the receptor form of IL1-RAP with a $K_D$ of 100 nM or lower (e.g., 1-10 nM, 0.1-10 nM, 10-50 nM, about 20 nM, etc.);

Reducing cell growth of IL1-RAP-expressing cells, compared to cell growth in the absence of the antibody; and Reducing cell growth of IL1-RAP-expressing cells when cross-linked or immobilized (e.g., on a solid or semisolid matrix), compared to cell growth in the absence of the antibody.

Reducing colony formation in IL-1RAP expression cancer cell lines.

Inhibiting IL-1b induced NF-kappB signaling in receptor IL1-RAP expression cells.

Reducing tumor burden in AML tumor xenograft animal models.

Binding to soluble IL1-RAP with a $K_D$ of 1 M or greater (e.g., greater than 10 M, greater than 100 M, etc.)

Binding to receptor IL-1Rap with a $K_D$ less than $10^{-7}$ M.

In some embodiments, the anti-IL1-RAP antibody binds to receptor IL1-RAP from a human. In some embodiments, the anti-IL1-RAP antibody binds to receptor IL1-RAP from a cynomolgus monkey. In some embodiments, the anti-IL1-RAP antibody binds to IL1-RAP from a rodent (mouse or rat).

A. Methods of Making Antibodies

For preparation of the presently described antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625, 126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention can also be produced in various formats, including as a Fab, a Fab', a $F(ab')_2$, a scFv, or a dAB. The antibody fragments can be obtained by a variety of methods, including, digestion of an intact antibody with an enzyme, such as pepsin (to generate $(Fab')_2$ fragments) or papain (to generate Fab fragments); or de novo synthesis. Antibody fragments can also be synthesized using recombinant DNA methodology. In some embodiments, the CLL-1 antibody comprises $F(ab')_2$ fragments that specifically bind CLL-1. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing non-human antibodies (i.e., using CDRs from non-human antibodies) are also known in the art. Generally, a humanized antibody has one or more amino acid residues from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.*

17:780, 1999; and Humphreys, et al., *Protein Eng. Des.* 20: 227, 2007). The antibody or antibody fragment can also be labeled, or conjugated to a therapeutic agent as described below.

B. Binding Affinity

The specificity of the binding can be defined in terms of the comparative dissociation constants (Kd) of the antibody (or other targeting moiety) for target, as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target. As used herein, a higher $K_d$ is a $K_d$ that describes a lower affinity interaction. Conversely a better or lower $K_d$ is a $K_d$ that describes a higher affinity interaction or tighter binding. By way of example only, the $K_d$ for an antibody specifically binding to a target may be femtomolar, picomolar, nanomolar, or micromolar and the $K_d$ for the antibody binding to unrelated material may be millimolar or higher. Accordingly, an antibody can bind the target molecule with an affinity that is 2-fold; 3-fold; 4-fold; 5-fold; 10-fold; 20-fold; 25-fold; 50-fold; 100-fold; 200-fold; 250-fold; 500-fold; 750-fold; 1,000-fold; 10,000-fold; 100,000-fold; 1,000,000-fold or more greater than the affinity for unrelated material. In some cases, the $K_d$ for the antibody binding to unrelated materials may be undetectable.

In some embodiments, the anti-IL1-RAP antibodies have an affinity for receptor IL1-RAP with a Kd of 1000 pM or lower, e.g., any of 800 pM, 700 pM, 600 pM, 500 pM, 400 pM, 300 pM, 200 pM, 100 pM, or lower. In some embodiments, the anti-IL1-RAP antibodies have an affinity for receptor IL1-RAP with a Kd of 10 nM ($10^{-2}$ mM, $10^{-5}$ M) or lower, e.g., 1 nM or lower, 1-10 nM, 100-1000 pM, 10-1000 pM, about 1 nM or lower, 1-500 pM. In some embodiments, the IL1-RAP antibodies also bind to primate receptor IL1-RAP, e.g., cynomolgus monkey, with Kd that is 10 nM, 1 nM, 500 pM or less. In some embodiments, the receptor IL1-RAP antibodies bind cynomolgus monkey receptor IL1-RAP with a Kd that is within an order of magnitude of the Kd for human receptor IL1-RAP. One of skill will understand that lower Kd values indicate higher affinity.

In some cases, the specificity of binding can be defined in terms of the comparative dissociation constants ($K_d$) of the antibody (or other targeting moiety) for target (i.e., the receptor form of IL1-RAP), as compared to the dissociation constant with respect to the antibody (or other targeting moiety) and the soluble form of IL1-RAP. For example, the $K_d$ for the antibody with respect to the soluble IL1-RAP can be at least 2-fold, 3-fold, 4-fold, 5-fold, 10-fold, 20-fold, 50-fold, 100-fold, 200-fold or more higher (i.e., lower affinity or worse binding) than the $K_d$ with respect to the receptor form of IL1-RAP. Accordingly, the antibody can bind the receptor form of IL1-RAP with an affinity that is 2-fold; 3-fold; 4-fold; 5-fold; 10-fold; 20-fold; 25-fold; 50-fold; 100-fold; 200-fold; 250-fold; 500-fold; 750-fold; 1,000-fold; 10,000-fold; 100,000-fold; 1,000,000-fold or more greater than the affinity for the soluble form of IL1-RAP.

In some cases, anti-IL1-RAP antibodies of the invention bind the receptor form of IL1-RAP but do not bind the soluble form of IL1-RAP. For example, the antibodies exhibit no detectable or discernible affinity to soluble IL1-RAP. In other cases, the antibodies do not substantially bind to soluble IL1-RAP. For example, the antibodies do not exhibit detectable binding to soluble IL1-RAP greater than background.

As another example, antibodies of the invention that bind the receptor form of IL1-RAP but do not substantially bind to the soluble form can exhibit a $K_d$ for binding to the soluble form that is any of 2-fold, 20-fold, 50-fold, 100-fold; 1,000-fold, 10,000-fold, 1,000,000-fold or greater than the $K_d$ for binding to the receptor form of IL1-RAP. Antibodies of the invention that bind the receptor form of IL1-RAP but do not substantially bind to the soluble form can also exhibit an affinity for the receptor form that is 20-fold, 50-fold, 100-fold; 1,000-fold, 10,000-fold, 1,000,000-fold or greater than the affinity for binding to the soluble form of IL1-RAP. In some cases, the anti-IL1-RAP antibodies of the invention can bind the receptor form of IL1-RAP with a femtomolar, picomolar, or micromolar IQ and exhibit millimolar or no detectable binding, e.g. by ELISA, FACS, surface plasmon resonance, etc., to the soluble form of IL1-RAP.

The desired affinity for an antibody, e.g., high (pM to low nM), medium (low nM to 100 nM), or low (about 100 nM or higher), may differ depending upon whether it is being used as a diagnostic or therapeutic. Without being limited to theory, in one example, an antibody with medium affinity may be more successful in localizing to a tumor as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Streptavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding.

Binding affinity can also be determined by anchoring a biotinylated interactant to a streptavidin (SA) sensor chip. The other interactant is then contacted with the chip and detected, e.g., as described in Abdessamad et al. (2002) Nuc. Acids Res. 30:e45.

V. Diagnostic Applications

The antibodies described herein specifically bind the receptor form of IL1-RAP and IL1-RAP-expressing cells. The receptor IL1-RAP-specific antibodies can thus be used for in vitro and in vivo diagnostic assays to detect IL1-RAP-expressing cells (e.g., CSCs; certain solid tumor cells; hematopoietic cancer cells; cells of the joint, bone or muscle; or cells involved in inflammatory diseases as indicated herein). For example, a sample (e.g., blood sample or tissue biopsy) can be obtained from a patient and contacted with a receptor IL1-RAP antibody, and the presence of a IL1-RAP expressing cell in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker. In some cases, antibodies of the invention specific for the receptor form of IL1-RAP but not the soluble form are useful for the detection or capture of IL1-RAP expressing cells from blood or other bodily fluids that contain soluble IL1-RAP.

In some embodiments, the anti-IL1-RAP antibody is contacted with a biological sample from an individual having or suspected of having an IL1-RAP associated disorder, and antibody binding to a cell in the sample is determined, wherein higher or lower than normal antibody binding indicates that the individual has an IL1-RAP associated disorder. In some embodiments, the biological sample is a blood sample or blood fraction (e.g., serum, plasma, platelets, red blood cells, white blood cells). In some embodiments, the biological sample is a tissue sample (biopsy), e.g., from a suspected tumor site, or from a tissue that is known to be affected, e.g., to determine the boundaries of a known tumor. In some embodiments, the biological sample is obtained from a site of inflammation.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine,* Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells, CD34+ cells, CD45+ cells, etc.) can be separated from the rest of the sample from the individual (e.g., other blood components) or cells in a tissue can be suspended for easier detection.

In some embodiments, the percentage of IL1-RAP-expressing cells in the sample is determined and compared to a control, e.g., a sample from an individual or group of individuals that are known to have an IL1-RAP associated disorder (positive control) or from an individual or group of individuals that are known not to have an IL1-RAP associated disorder (normal, non-disease, or negative control). In some embodiments, the control is a standard range of IL1-RAP expression established for a given tissue. A higher or lower than normal percentage of IL1-RAP expressing cells, or higher or lower expression level, indicates that the individual has an IL1-RAP associated disorder.

In some embodiments, a labeled anti-IL1-RAP antibody can be provided (administered) to an individual to determine the applicability of an intended therapy. For example, a labeled antibody may be used to detect IL1-RAP density within a diseased area, where the density is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.).

In some embodiments, labeled antibodies specific for receptor IL1-RAP as described herein can be further associated with a therapeutic compound, e.g., to form a "theranostic" composition. For example, an anti-IL1-RAP antibody described herein can be linked (directly or indirectly) to both a detectable label and a therapeutic agent, e.g., a cytotoxic agent to kill IL1-RAP-expressing cancer cells. In some embodiments, a labeled antibody specific for the receptor form of IL1-RAP is used for diagnosis and/or localization of an IL1-RAP expressing cancer cell, and the IL1-RAP expressing cancer cell is then targeted with a separate therapeutic antibody specific for the receptor form of IL1-RAP. In some embodiments, the diagnostic antibody that is specific for the receptor form of IL1-RAP is one that is not internalized into IL1-RAP expressing cells at a high rate or percentage. In some embodiments, the therapeutic antibody specific for the receptor form of IL1-RAP is an antibody that inhibits proliferation of IL1-RAP expressing cells upon crosslinking or multimerization.

A. Labels

A diagnostic agent comprising a receptor IL1-RAP antibody can include any diagnostic agent known in the art, as provided, for example, in the following references: Armstrong et al., *Diagnostic Imaging,* 5th Ed., Blackwell Publishing (2004); Torchilin, V. P., Ed., *Targeted Delivery of Imaging Agents,* CRC Press (1995); Vallabhajosula, S., *Molecular Imaging: Radiopharmaceuticals for PET and SPECT,* Springer (2009). A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

In some embodiments, the label can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives. Fluorescent dyes are discussed, for example, in U.S. Pat. Nos. 4,452,720, 5,227,487, and 5,543,295.

The label can also be a radioisotope, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In some embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the labeled antibody can be further associated to a composition that improves stability in vivo, e.g. PEG or a nanoparticle such as a liposome, as described in more detail below.

B. Methods of Labeling

Techniques for conjugating detectable and therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

Typically, the antibody is attached to detectable moiety in an area that does not interfere with binding to the epitope. Thus in some cases, the detectable moiety is attached to the constant region, or outside the CDRs in the variable region. One of skill in the art will recognize that the detectable moiety can be located elsewhere on the antibody, and the position of the detectable moiety can be adjusted accordingly. In some embodiments, the ability of the antibody to associate with the epitope is compared before and after attachment to the detectable moiety to ensure that the attachment does not unduly disrupt binding.

In some embodiments, the antibody can be associated with an additional targeting moiety. For example, an antibody fragment, peptide, or aptamer that binds a different site on the target molecule or target cell can be conjugated to the antibody to optimize target binding, e.g., to a cancer cell.

VI. Therapeutic Applications

IL1-RAP is aberrantly expressed in a number of disease states, and the IL1-RAP-expressing cells in such conditions can be targeted using the antibodies described herein that are specific for the receptor form of IL1-RAP. For example, IL1-RAP expression is elevated on cancer cells (e.g., B cell lymphoma, AML cells, and solid tumor cells described herein); CSCs (e.g., myeloid CSCs); and cells associated with the IL1-RAP associated disorders provided herein. IL1-RAP is not significantly expressed on normal hematopoietic stem cells (HSCs). As noted above, a therapeutic composition comprising an anti-IL1-RAP antibody can further include a detectable label to form a theranostic composition, e.g., for detection and localization of IL1-RAP expressing cells, and monitoring of therapeutic effect.

A. Chemotherapeutic and Cytotoxic Agents

As demonstrated herein, anti-IL1-RAP antibodies can inhibit cancer cell growth (proliferation), and thus can be considered chemotherapeutic agents. The following disclosure provides examples of additional chemotherapeutic and cytotoxic agents that can be linked to an anti-IL1-RAP antibody for delivery to IL1-RAP-expressing cells.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, vinca alkaloids, anthracycline, and platinum-based agents. Classes of chemotherapeutic agents include but are not limited to alkylating agents, antimetabolites, e.g., methotrexate, plant alkaloids, e.g., vincristine, and antitumor antibiotics such as anthracyclines, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy. Chemotherapeutics also include agents that inhibit tubulin assembly or polymerization such as maytansine, mertansine, and auristatin. Chemotherapeutic agents also include DNA damage agents such as calicheamicin.

Chemotherpeutic agents can include maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof Chemotherapeutics currently used for treating myeloma include bortezomib, lenalidomide, and thalidomide. Additional therapeutic agents that can be administered to myeloma patients include bisphosphonates (to prevent bone fractures) and erythropoietin (to reduce anemia).

More than one therapeutic agent can be combined, either in the same composition, or in separate compositions. The therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients.

B. Methods of Forming Therapeutic Compositions

Antibodies can be attached to a therapeutic agent, detectable agent, or nanocarrier using a variety of known cross-linking agents. Methods for covalent or non-covalent attachment of polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. Nos. 5,603,872 and 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexyl-carbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide. Agents can be conjugated through cysteine residues in the antibody, which can be naturally occurring or artificially introduced.

For antibodies conjugated to nanocarriers (e.g., liposomes), a certain number of antibodies will be present on the surface, i.e., at a given surface density. In some embodiments, the nanocarrier will have at least 5 antibodies per nanocarrier, e.g., at least 10, 30, 40, 50, 75, 100 or higher antibodies per nanocarrier. One of skill in the art will understand that surface density represents an average range, as the number of antibodies per nanocarrier will not be absolutely uniform for all members of the population.

Nanocarriers include vesicles such as liposomes and micelles, as well as polymeric nanoparticles, etc. Nanocarriers are useful for delivery of therapeutic and diagnostic agents, but can be particularly useful for shielding cytotoxic agents used to treat cancer. The nanocarrier can comprise lipids (e.g., phospholipids), hydrophilic polymers, hydrophobic polymers, amphipathic compounds, cross-linked polymers, and a polymeric matrix (see, e.g., WO2009/110939). Depending on the application, the nanocarrier can be designed to have a particular size, half-life, shelf life, and leakage rate.

Preparation of nanocarriers, such as an antibody targeted liposome, polymeric nanoparticle, or extended shelf-life liposome, is described, e.g., in U.S. Pat. Nos. 6,465,188, 7,122,202, 7,462,603 and 7,550,441.

In some embodiments, the antibody is linked to a stabilizing moiety such as PEG, or a liposome or other nanocarrier. U.S. Pat. Nos. 4,732,863 and 7892554 and Chattopadhyay et al. (2010) *Mol Pharm* 7:2194 describe methods for attaching the selected antibody to PEG, PEG derivatives, and nanoparticles (e.g., liposomes). Liposomes containing phosphatidyl-ethanolamine (PE) can be prepared by established procedures as described herein. The inclusion of PE provides an active functional site on the liposomal surface for attachment.

The antibody conjugate can also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunocongugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

C. Methods of Administration

The anti-IL1-RAP antibodies of the invention can efficiently deliver a therapeutic composition to IL1-RAP-expressing cells in vivo. In some embodiments, the method of treatment comprises administering to an individual an effective amount of a therapeutic anti-IL1-RAP conjugate, e.g., an anti-IL1-RAP antibody attached to a therapeutic agent. In some embodiments, the individual has been diagnosed with cancer. In some embodiments, the individual is receiving or has received cancer therapy, e.g., surgery, radiotherapy, or chemotherapy. In some embodiments, the individual has been diagnosed, but the cancer is in remission.

In some embodiments, the anti-IL1-RAP conjugate includes a liposome. In some embodiments, the method further comprises monitoring the individual for progression of the cancer. In some embodiments, the dose of the anti-IL1-RAP conjugate for each administration is determined based on the therapeutic progress of the individual, e.g., where a higher dose of chemotherapeutic is administered if the individual is not responding sufficiently to therapy.

In some embodiments, the invention can include an antibody or antibody-targeted composition and a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the antibody-targeted composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted compositions can be presented in unit-dose or multi-dose sealed containers, such as ampoules and vials.

The targeted delivery composition of choice, alone or in combination with other suitable components, can be made into aerosol formulations ("nebulized") to be administered via inhalation. Aerosol formulations can be placed into pressurized acceptable propellants, such as dichlorodifluoromethane, propane, and nitrogen.

The pharmaceutical preparation can be packaged or prepared in unit dosage form. In such form, the preparation is subdivided into unit doses containing appropriate quantities of the active component, e.g., according to the dose of the therapeutic agent or concentration of antibody. The unit dosage form can be a packaged preparation, the package containing discrete quantities of preparation. The composition can, if desired, also contain other compatible therapeutic agents.

The antibody (or antibody-targeted composition) can be administered by injection or infusion through any suitable route including but not limited to intravenous, subcutaneous, intramuscular or intraperitoneal routes. An example of administration of a pharmaceutical composition includes storing the antibody at 10 mg/ml in sterile isotonic aqueous saline solution for injection at 4° C., and diluting it in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

In therapeutic use for the treatment of cancer, an antibody-targeted composition (e.g., including a therapeutic and/or diagnostic agent) can be administered at the initial dosage of about 0.001 mg/kg to about 1000 mg/kg daily and adjusted over time. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosage is varied depending upon the requirements of the patient, the severity of the condition being treated, and the targeted composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted composition in a particular patient, as will be recognized by the skilled practitioner.

All patents, patent applications, and other publications, including GenBank Accession Numbers, cited in this application are incorporated by reference in the entirety for all purposes.

EXAMPLES

Example 1

Generation of Antibody Against IL1-RAP

A cDNA fragment of human IL1-RAP encoding the extracellular domain (residues 21-367 of Q9NPH3 ("Q9NPH3-4")) was cloned from a full length human IL1-RAP cDNA (Open Biosystems). A 6xHis tagged was added to C-terminal to generate a IL1-RAP-His fusion protein, which was used to immunize mice to produce monoclonal mouse anti-human IL1-RAP antibodies. Hybridomas were generated using standard protocols. In brief, 4-6 week old Balb/c mice were immunized with purified recombinant IL1-RAP fusion protein twice a week for a total of 4 weeks. Titers were assessed thereafter and the spleen cells were fused with SP2/0 cells. Hybridomas were selected and supernatants from the resulting clones were screened by enzyme linked immunosorbent assay (ELISA) and fluorescent activated cell sorting (FACS).

The specificity of selected hybridoma clones was examined by FACS binding to either parental or human IL1-RAP-transfected 293/293IL1-RAP cells and multiple AML cell lines, such as OCI-AML2, OCI-AML3 and HNT-34. The binding results of antibody clone 50.3G7 are shown in FIG. 1.

Example 2

Generation of Antibody Against Membrane-Bound Form of IL1-RAP

Figure 2:
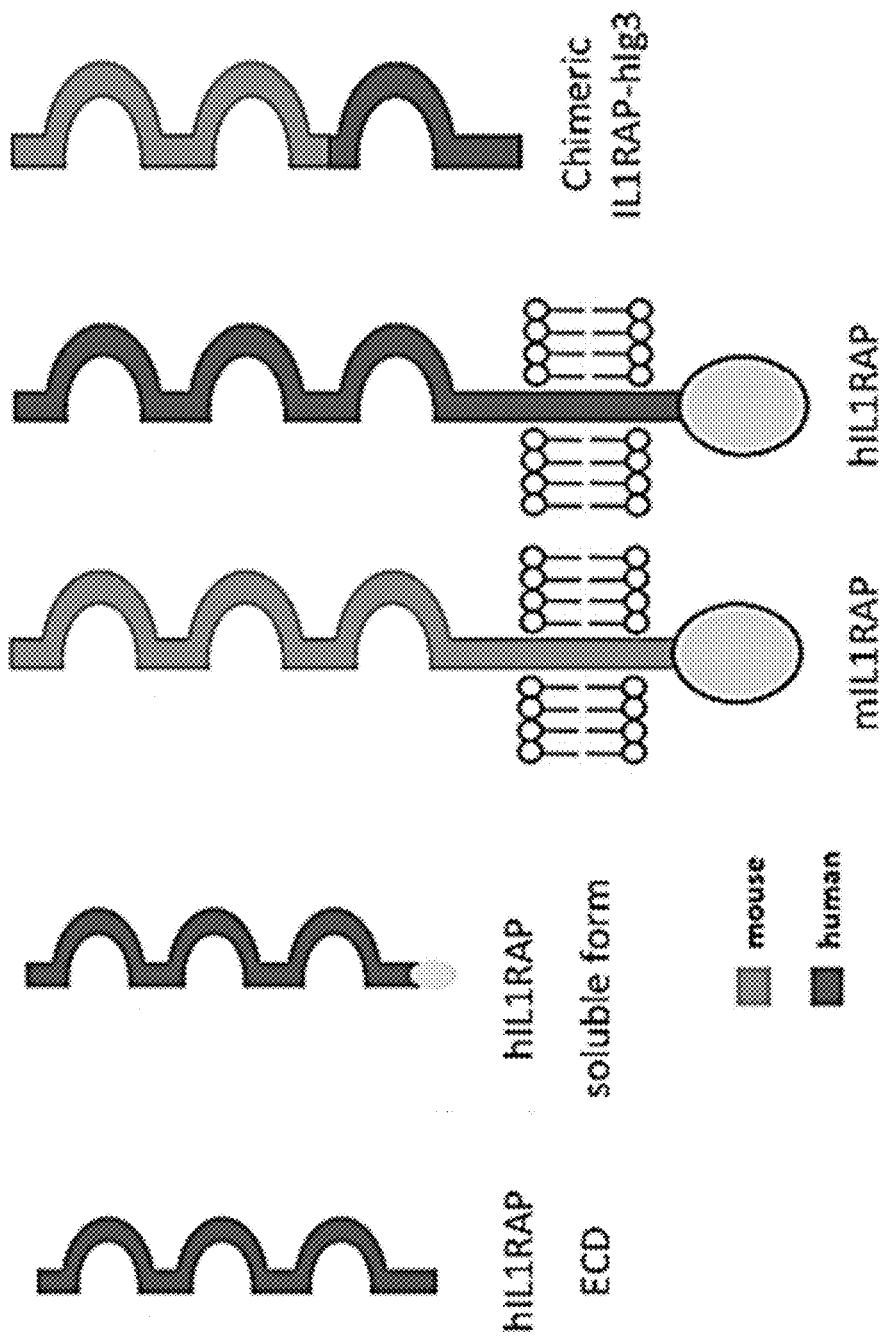
FIG. 2 is a schematic of the chimeric human/mouse proteins that were generated to immunize mice to create the anti-IL1-RAP antibodies of the disclosure.

In order to generate an antibody that is specific to recognizing membrane-bound IL1-RAP, various chimeric mouse/human IL1-RAP proteins were generated. Mice were immunized with each chimera, and ELISA based screening was used to screen mAbs specific to membrane-bound ILRAP. A schematic is shown in FIG. 2.

2a. Identification of Antibodies That Bind Specifically Membrane-Bound IL1-RAP

Antibody clones preferentially recognizing membrane-bound IL1-RAP were identified by indirect ELISA using his-tagged extracellular domain (ECD) of IL1-RAP (Q9NPH3-4) and soluble IL1-RAP form (Q9NPH3-2). Clones were detected using a peroxidase-conjugated goat anti-mouse IgG (subclasses IgG1, 2 and 3 specific) antibody.

2b. 2H8 Preferentially Recognizes Membrane Bound IL1l-RAP by ELISA

Figure 3A:
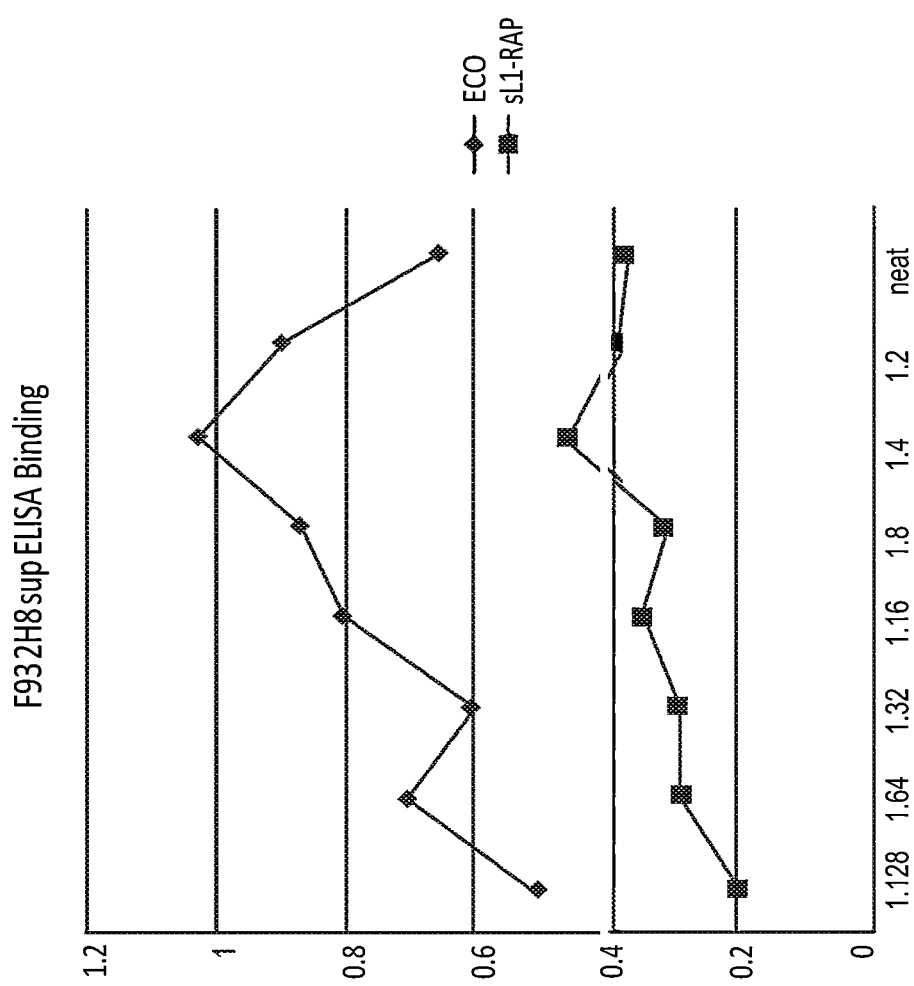
FIGS. 3A and 3B show results of ELISA assays. 3A: Direct ELISA, plate coated with extracellular domain IL1-RAP or with the soluble form IL1RAP; 3B: Sandwich ELISA, plate coated with goat anti-IL1RAP antibody, then add extracellular domain of IL1-RAP or soluble IL1-RAP, finally add 2H8 antibody. Antibody 2H8 preferentially binds to extracellular domain IL1RAP.
Figure 3B:
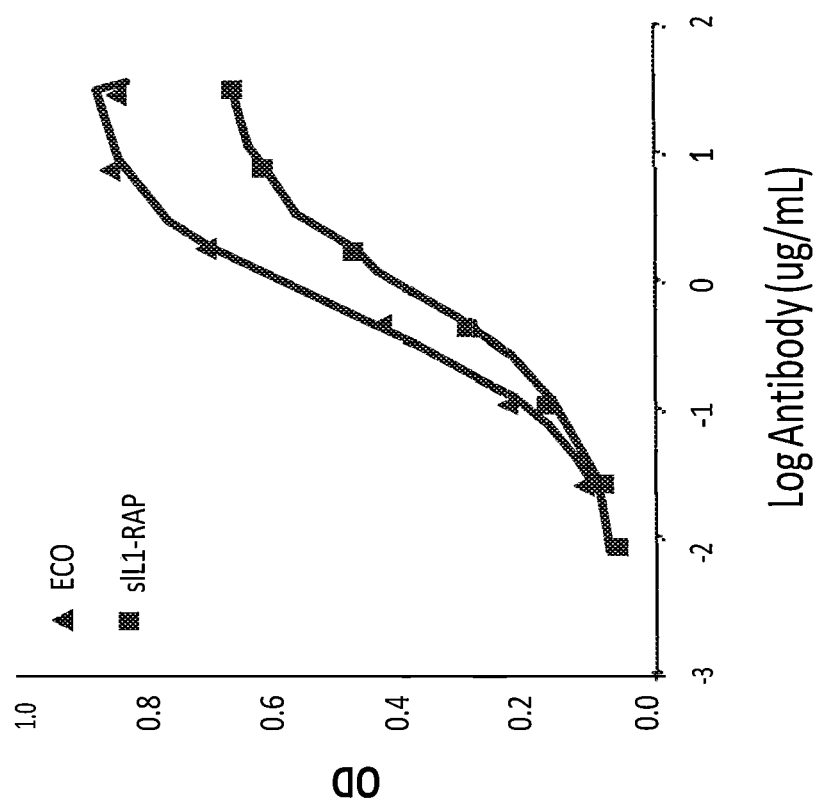
Figure 6A:
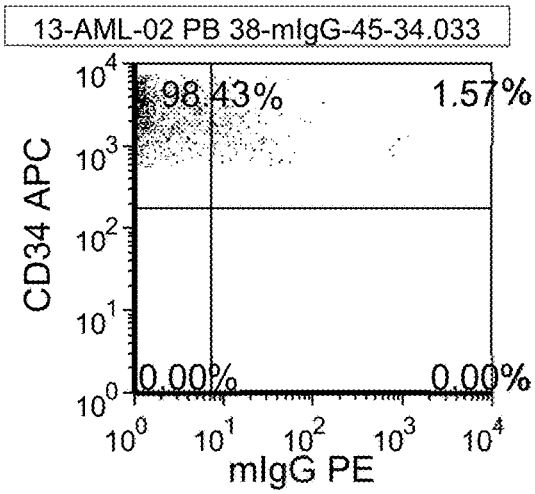
FIGS. 6A-6D are scatter plots of FACS analysis showing testing binding of clones 2H8, 50.3G7 and 56.12G6 to AML cells of a single primary patient. Of twelve AML patients tested, six are positive with 2H8.
Figure 6B:
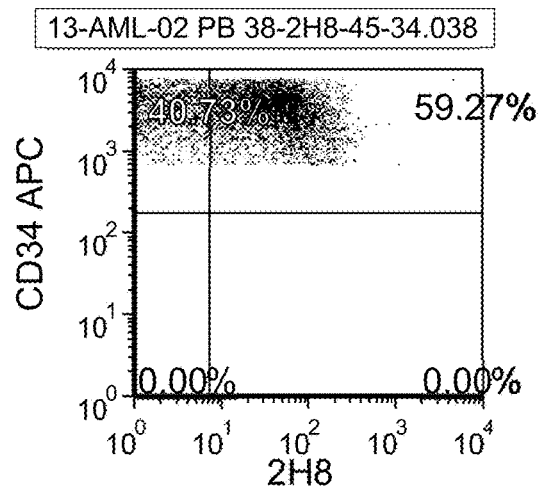
Figure 6C:
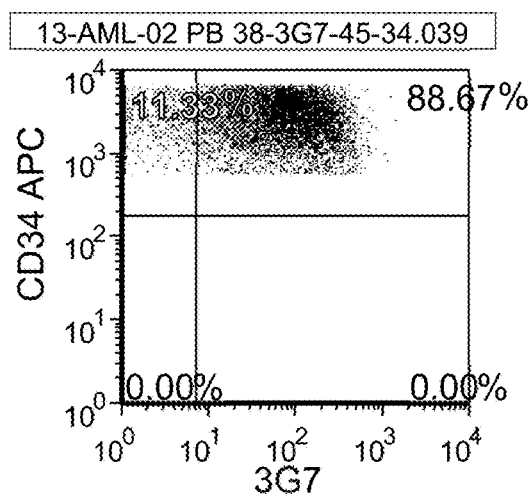
Figure 6D:
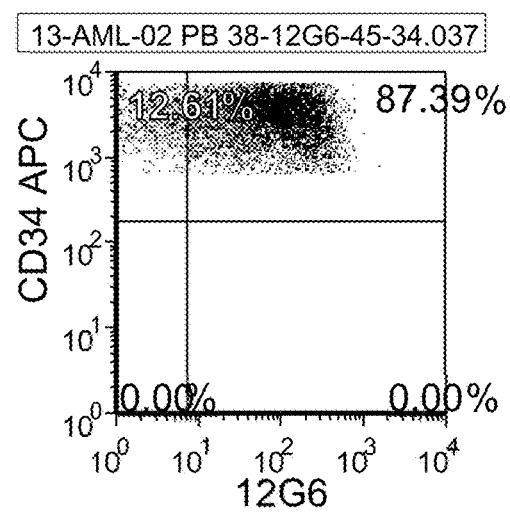

The extracellular domain of IL1-RAP (Q9NPH3-4) and soluble IL1-RAP form (Q9NPH3-2) were expressed and purified from 293 cells. Sandwich ELISA was performed. The binding data shown in FIGS. 3A and 3B supports the conclusion that clone 2H8 binds to membrane-bound IL1-RAP better compared to soluble IL1-RAP form.

2c. 2H8 Binding to AML Cell Lines

The binding specificity of Clones 2H8, 5H9.1.4 and 56.12G6 were tested against various cell lines (i.e., 293T, IL1-RAP transfected 293, EOL-1, HNT-34) by FACS. Results are presented in FIGS. 4A-4D. The data suggests that 2H8 binds selectively IL1-RAP expressing 293 cells or AML cell lines.

2d. Binding of 2H8 to IL1-RAP is Minimally Affected by Normal Human Serum

The binding of various anti-IL1-RAP antibodies to HNT-34 cells was tested in the presence of various levels of normal human serum (NHS) isolated from healthy patients and soluble IL1-RAP (Q9NPH3-2 or extracellular domain (ECD) of IL1-RAP (Q9NPH3-4) are shown in FIGS. 5A-5D. Left: Antibody binding titration on HNT-34 cells. Right: EC50 values for treatment conditions. Human serum or IL1-RAP proteins did inhibit 56.12G6 binding to HNT-34 cells more effectively than 2H8 indicating that 2H8 antibody may display minimal interference from the soluble IL1-RAP present in the human serum.

Example 3

IL-RAP Binding to Primary AML Samples

IL1-RAP clones were tested to determine binding to AML primary patient samples. A total of 12 AML patient samples were examined with clones 2H8, 50.3G7 and 56.12G6, all antibodies directed against IL1-RAP surface-expressed protein. 2H8 recognized 6/12 (50%) of CD34+ populations of patient AML patient samples. These AML patient samples were from various 2008 WHO and FAB classifications. FIGS. 6A-6D show exemplary FACs data for individual positive patients.

Expression Analysis by Flow Cytometry. BMMC or PBMC were isolated from bone marrow aspirate or whole blood by Ficoll® separation (GE Healthcare). Cells were resuspended in staining solution (HBSS, 1% BSA, 1 mM EDTA) to $2 \times 10^6$ cells/mL and blocked with either mouse, rat or human IgG prior to staining. 5 µL of CD34-APC were added to each tube with 50 µL of staining solution. various antibodies, mIgG, 2H8, 56.12G6, 50.3G7 antibodies were added to each tube to a final concentration of 2 ug/mL, then APC conjugated goat anti-mouse secondary antibody were added to each tube and incubated on ice for 30 min. Cells were washed with staining solution and resuspended in 200 µL of staining solution with propidium iodide. Cells were immediately applied to flow cytometry for analysis. A sample was considered positive for target if the ratio of the geometric mean fluorescence intensity (MFI) of the stained sample and that of isoform IgG control was greater than 1.5 and more than 5% of the cells expressed the antigen compared with the control sample or in some instances, a distinct positive population rather than a general shift of >1% of the cells.

In addition, 83 AML samples were stained against IL1-RAP clones generated. 78 (94%) of the samples stained positive for at least one IL1-RAP clone. 4/4 (100%) bone marrow samples and 75/79 (95%) peripheral blood (PBMC, peripheral blood mononuclear cells) samples stained positive for IL1-RAP (see Table 2). AML samples were broken down into French-American-British (FAB) classification groups for analysis.

TABLE 2

FAB subtypes (NCCN (National Comprehensive Cancer Network) cytogenetic classification)

| Tote  | M1    | M2    | M4    | M5  | other | NA  | BM  | PBMC  |
|-------|-------|-------|-------|-----|-------|-----|-----|-------|
| 78/83 | 20/22 | 17/19 | 17/17 | 9/9 | 9/10  | 6/6 | 4/4 | 75/79 |
|       | Good  |       | Inter |     | Poor  |     |     | NA    |
|       | 9/9   |       | 36/38 |     | 21/24 |     |     | 12/12 |

Example 4

Epitope Mappine of IL1-RAP Clones

Figure 13:
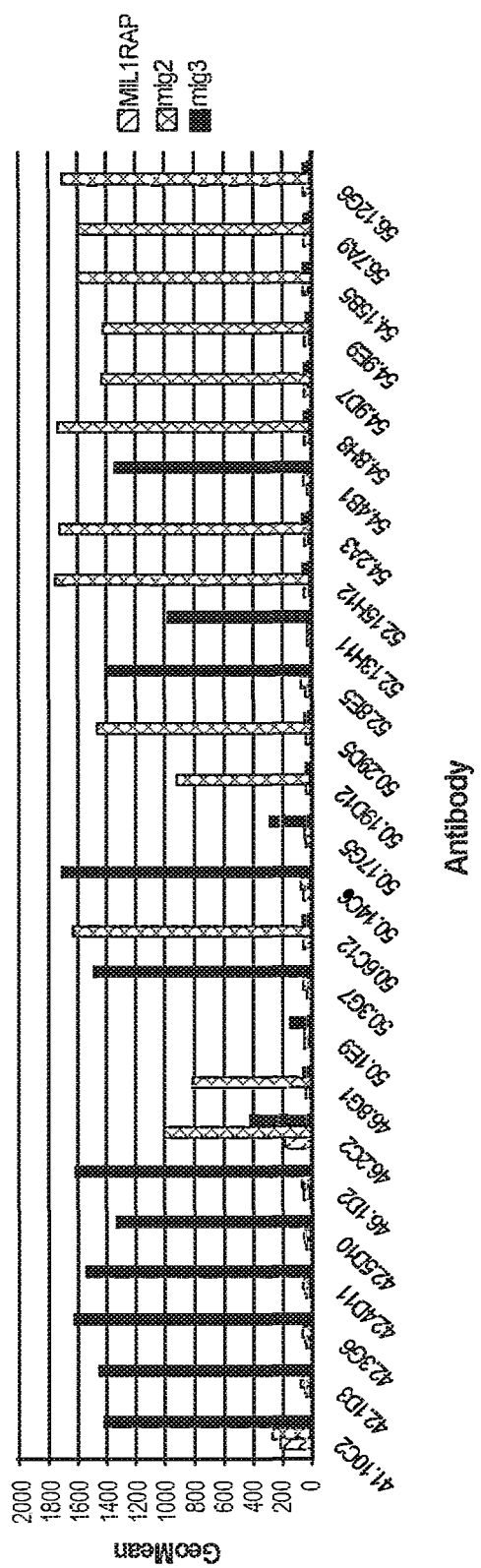
FIG. 13 is a histogram showing the binding of various antibody clones to mIg2 and mIg3 as examined by FACS.
Figure 14:
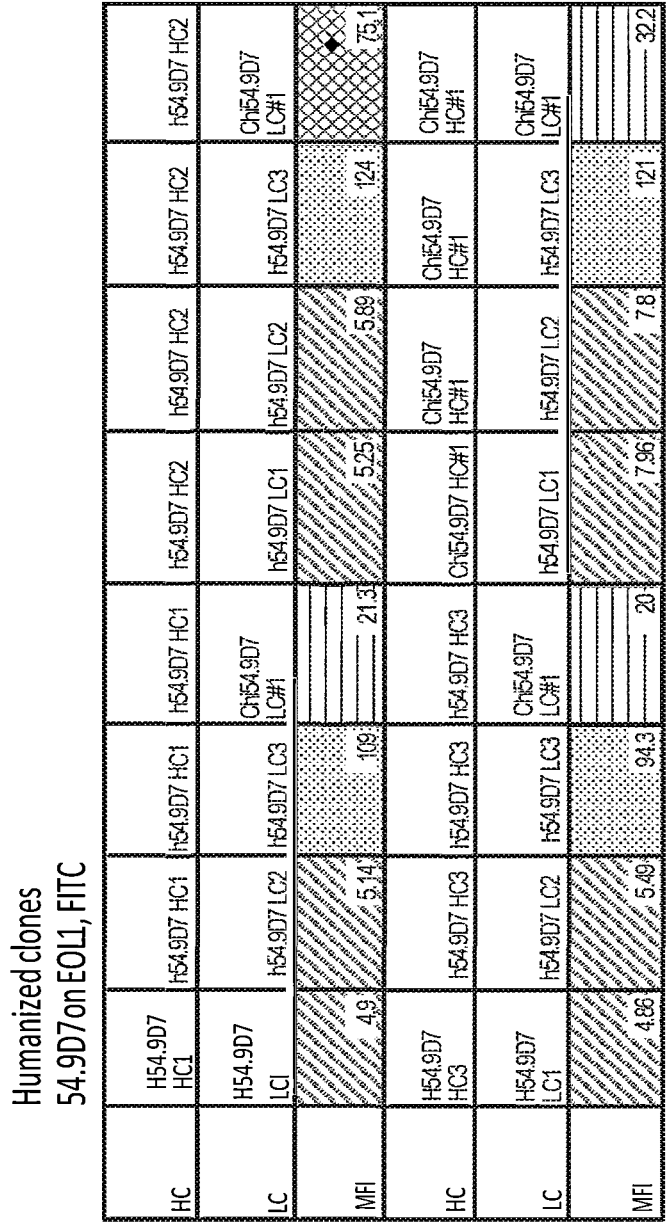
FIG. 14 shows the mean fluorescent intensity (MFI) values of humanized clones of 54.9D7 having different combinations of HC and LC in binding to EOL-1 cells.
Figure 15:
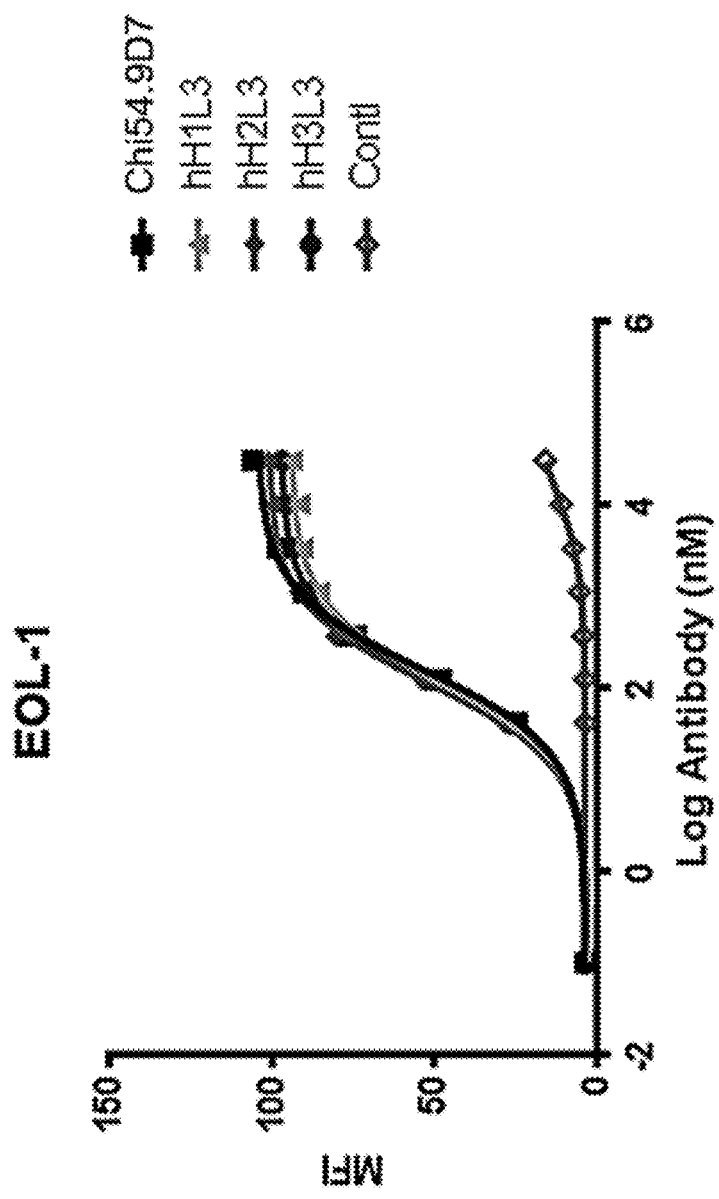
FIG. 15 is a plot of the MFI values of three humanized clones of 54.9D7 in binding to EOL-1 cells.
Figure 16A:
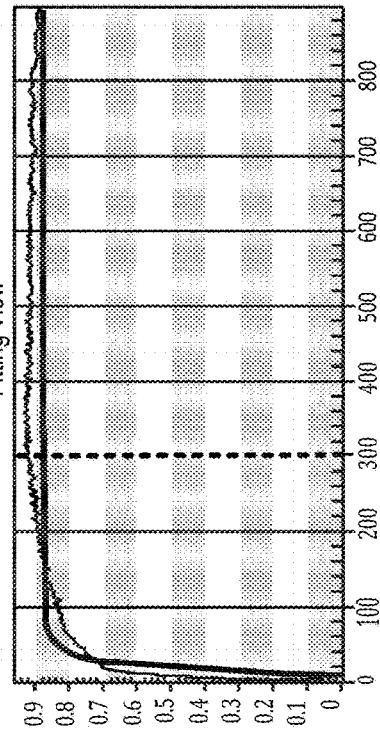
FIGS. 16A-16D are plots showing the binding affinities of chimeric 54.9D7 and three humanized clones of 54.9D7.
Figure 16B:
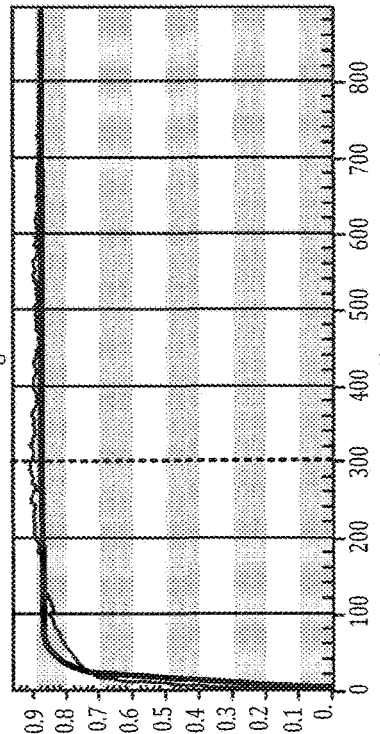
Figure 16C:
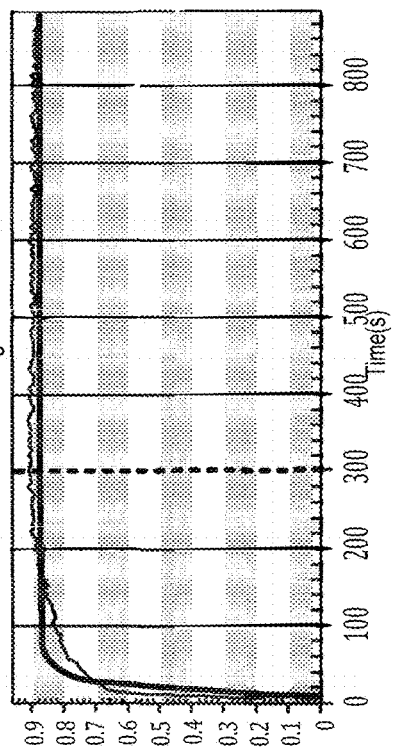
Figure 16D:
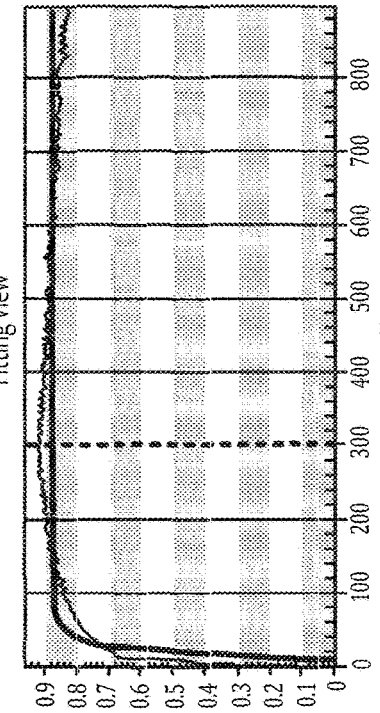

Various anti-IL1-RAP antibodies generated pursuant to this disclosure were tested for binding to recombinant mouse IL1-RAP. As none of the clones bound to mouse IL1-RAP, mouse/human IL1l-RAP chimeric receptors were generated, including either mouse domain mIg2 or mIg3. (See FIG. 2.) The chimeric mouse/human receptors were transiently transfected into 293 cells. The binding of IL1-RAP clones to mIg2 and mIg3 were examined by FACS and plotted in the histogram shown in FIG. 13. In summary, there are clones which need mouse domain mIg2 for binding, such as 50.3G7, there are clones which need mouse domain mIg3 for bidning, such as 56.12G6.

Example 5

Functional Characterization of IL1-RAP Clones

Figure 7:
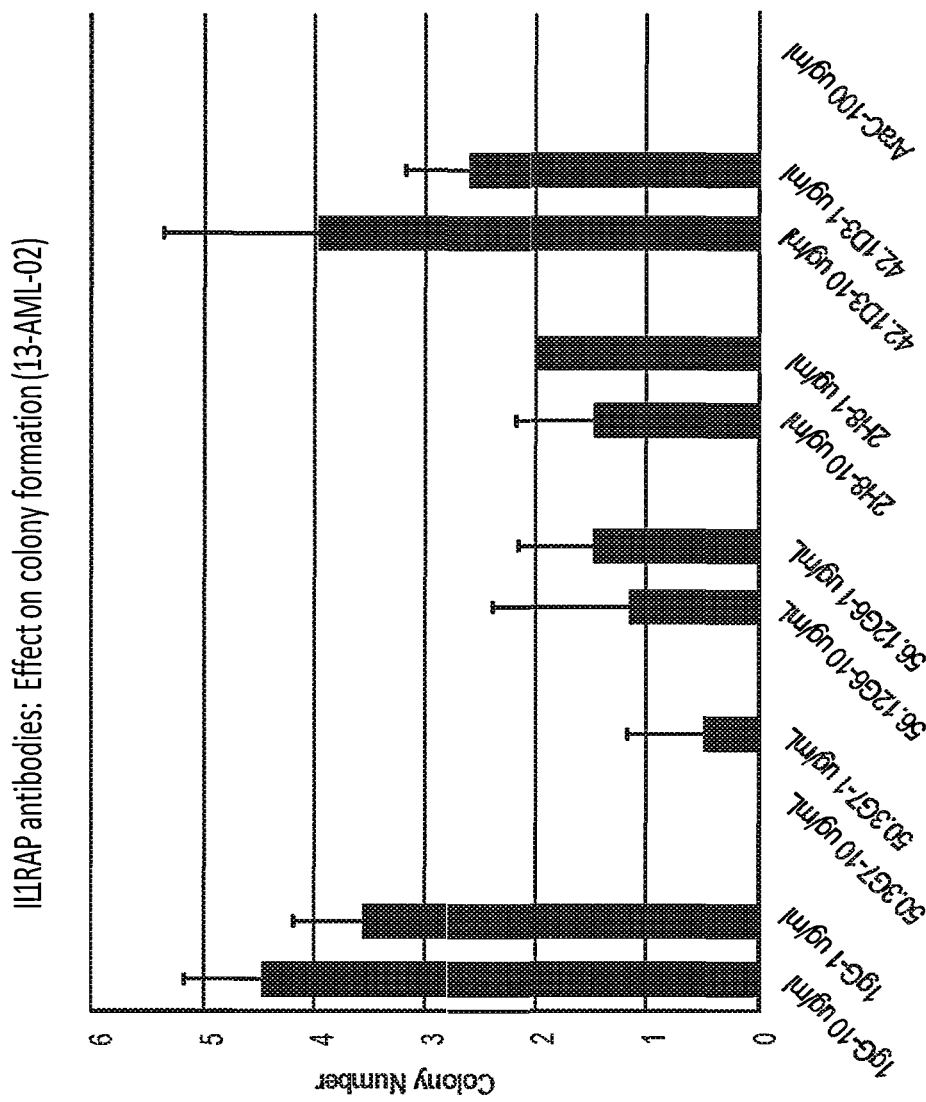
FIG. 7 is a histogram showing the results of the Colony Forming cell (CFC) assay descried in Example 15.

IL1-RAP clones were evaluated in a colony forming cell (CFC) assay. Briefly, Cells were isolated using either Ficoll® (GE Healthcare) or CD34+enrichment kit (Stem Cell). Dead cells were removed using the Live-Dead Kites® (Miltenyi) and viable cells were adjusted to a final concentration of $2\times10^3$ cells per mL for CD34+ cells, $1\times10^4$ cells per mL for BMMC, $2\times10^5$ cells per mL for PBMC. 2H8 or IgG control antibodies were added to cell solution to a final concentration of either 10 µg/mL or 1 µg/mL incubated for 1 h at 37° C. Cells were washed with PBS and then re-suspended in media to same volume. The cell solution (0.3 mL) was mixed with 2.7 mL of Methocult™ w/o EPO (Stem Cell) for approximately 450 CD34+ cells/tube, 3,000 BMMC/tube or 30,000 PBMC/tube and the mixture was plated to 35 $mm^2$ dishes and allowed to incubate at 37° C. for two weeks. Resultant colonies were counted and the results are shown in FIG. 7.

Figure 8:
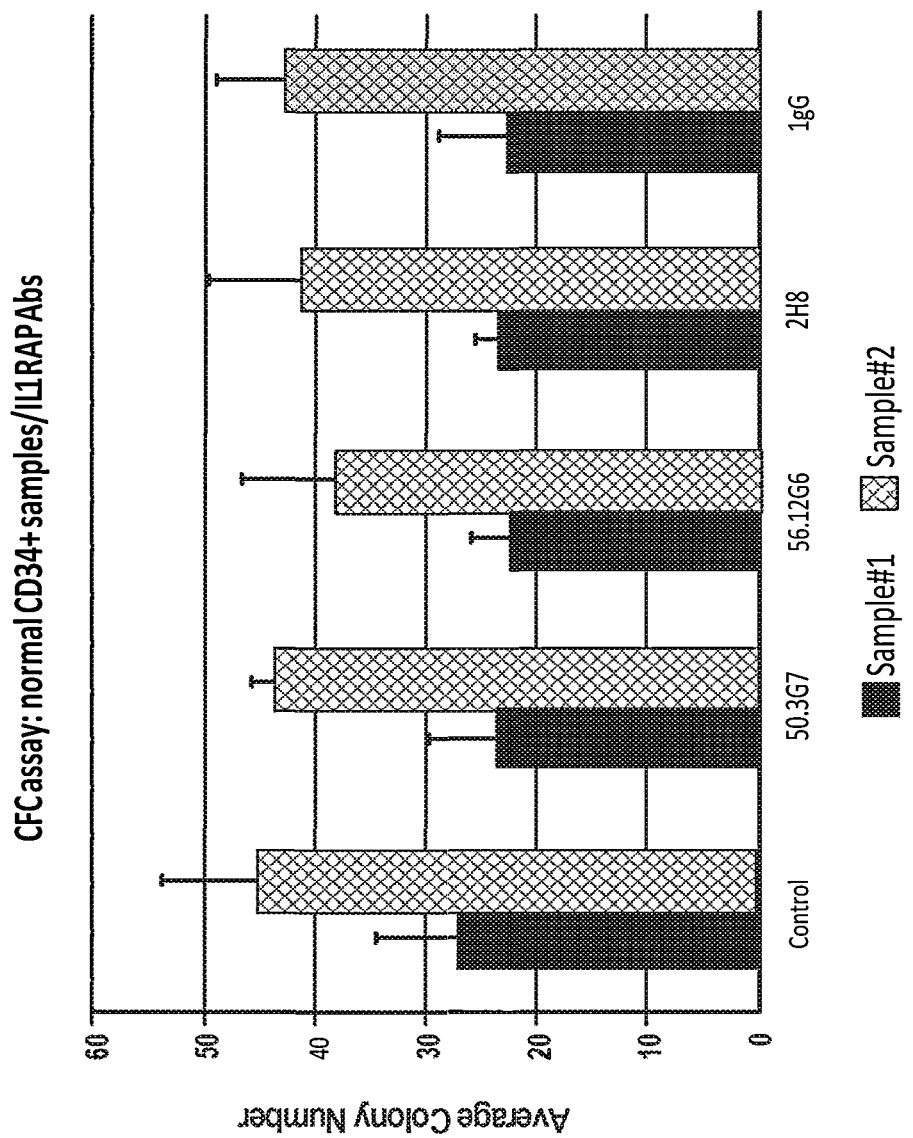
FIG. 8 is a histogram showing demonstrating the effect of the anti-IL1-RAP clones on healthy CD34+ cells.

CFC assay was performed to understand antibody effect on leukemia stem cell-like cells. As patients with AML have both blast cells and leukemia stem cell-like cells within the blood and marrow, we asked whether the antibody preferentially homes onto one subset or affects the malignant cells equally. To explore this possibility, a CFC assay was performed. A reduction in the colony formation was seen in 2H8 treatment, along with 50.3G7 and 56.12G6. However, there is no effect on normal CD34 cells comparing to control IgG. Both AML blast cells and leukemic stem cell-like cells are targeted by IL1-RAP antibodies. In contrast, normal HSCs are unaffected by these antibodies. The results are shown in FIG. 8.

The addition of IL1-RAP antibodies to AML patient blast cells resulted in the inhibition of colony formation compared to isotype antibody controls. Although assessing colony formation using semi-solid media is the classical approach to determine the self-renewing potential of the leukemic stem cells, it does not directly assess the population of leukemic stem cells that are present within a diseased patient.

Example 6

Inhibition of IL-1β-induced NF-κB Signaling

Figure 9:
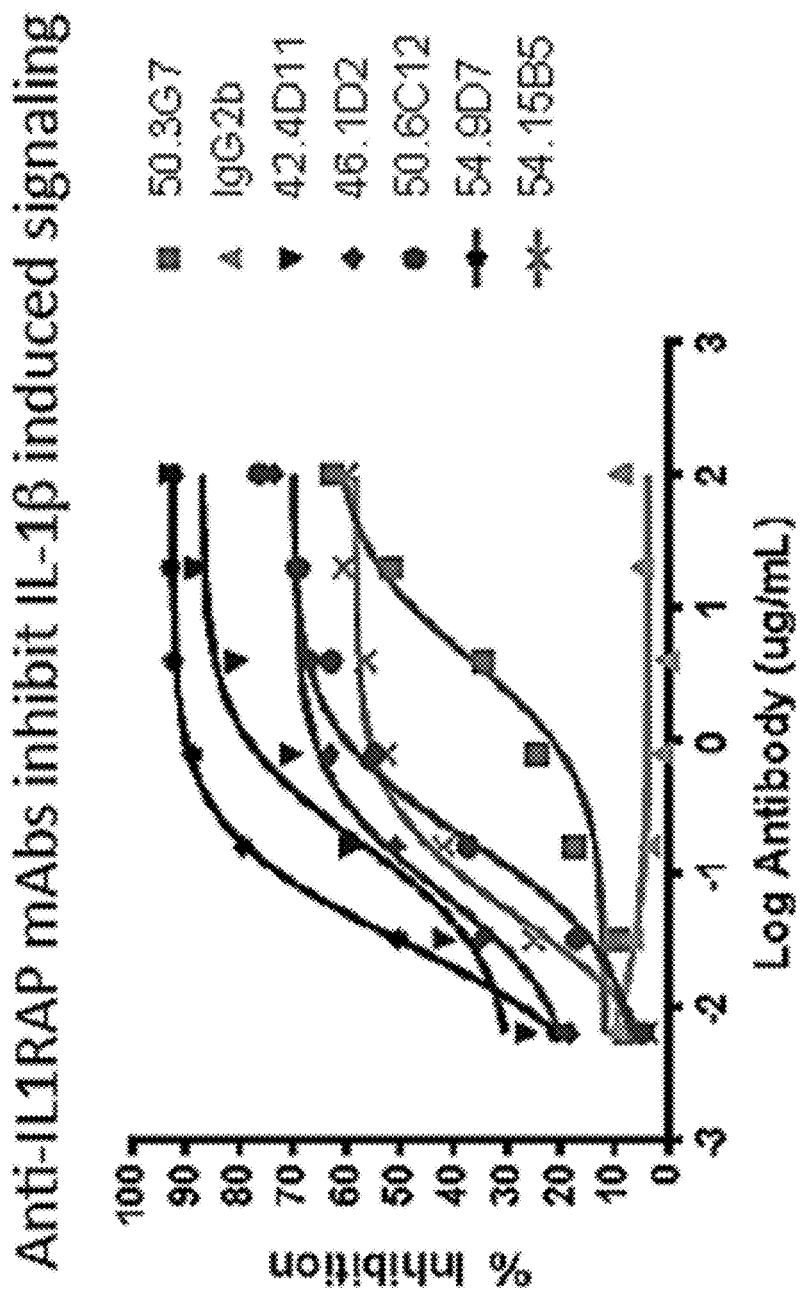
FIG. 9 is a plot of percent inhibition as a function of anti-IL1-RAP clone concentration.

HEK-Blue IL-1β cells were treated with 50 pg/mL recombinant human IL-1β. 25 IL1-RAP mAb clones were screened for inhibition of IL-1β-induced NF-κB signaling. IL-1Ra was used as a positive control. Anti-IL1-RAP mAb clones were titrated from 6.4 ng/mL up to 100 µg/mL. The 10 antibodies in Table 3 have an $IC_{50}$<12 µg/mL and 6 have an $IC_{50}$<0.5 µg/mL. Maximum inhibition observed at 10 µg/mL antibody was 92.3% for clone 54.9D7. The lowest $IC_{50}$ observed was 32.3 ng/mL, also for clone 54.9D7. The percent inhibition is graphed as a function of antibody concentration in FIG. 9, and shown in tabular in Table 3.

TABLE 3

| Antibody | $IC_{50}$ (ug/mL) | % Inhibition at 10 ug/mL | Antibody | $IC_{50}$ (ug/mL) | % Inhibition at 10 ug/mL |
|----------|-------------------|--------------------------|----------|-------------------|--------------------------|
| 54.2A3   | 10.35             | 50.1                     | 50.3G7   | 12.57             | 48.0                     |
| 54.8H8   | 2.05              | 50.8                     | 42.1D3   | 7.99              | 59.0                     |
| 54.9D7   | 0.03              | 92.3                     | 42.4D11  | 0.10              | 86.0                     |
| 54.9E9   | 1.30              | 69.1                     | 46.1D2   | 0.13              | 69.2                     |
| 54.15B5  | 0.29              | 58.1                     | 50.6C12  | 0.41              | 69.0                     |

Example 7

In Vivo Assessment of IL1-RAP Antibodies

Figures 10A, 10B, 10C:
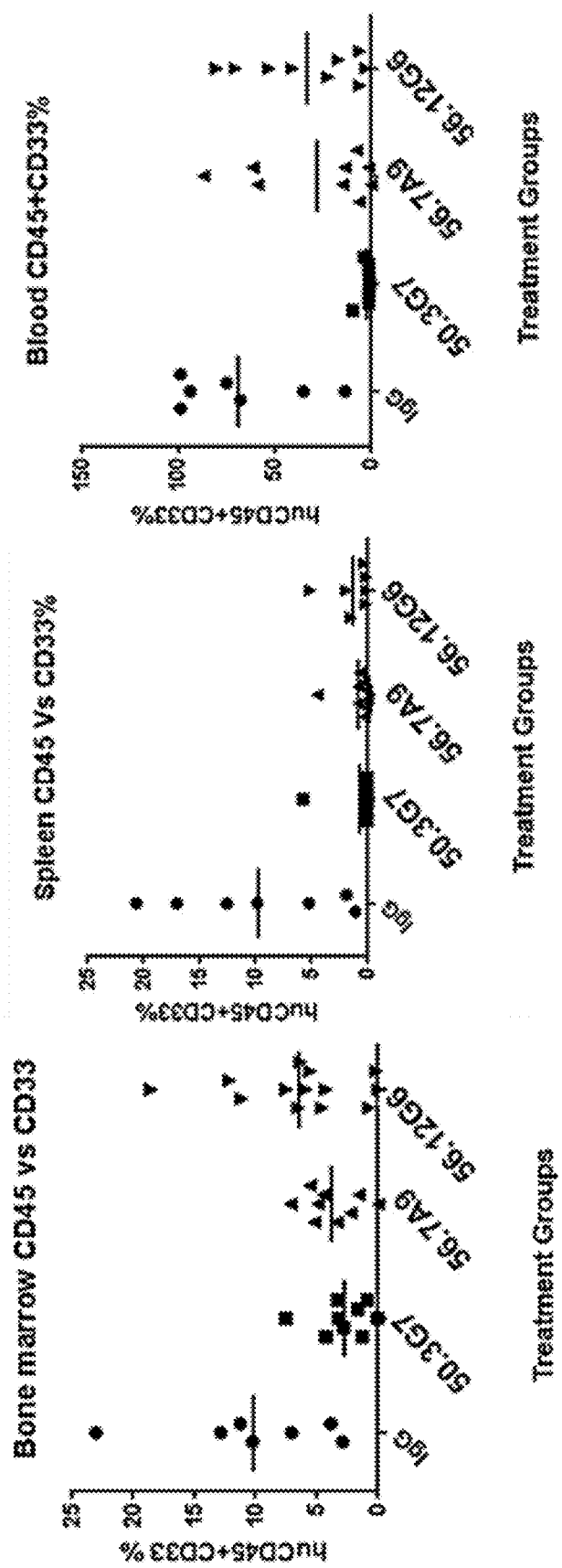
FIGS. 10A-10C are graphs of tumor burden in bone marrow, spleen and blood cells in mice treated with various anti-IL1-RAP clones.

An AML tumor-bearing model engrafted with EOL-1 tumor cells was established to evaluate the initial efficacy of the anti-IL1-RAP antibody clones. Clone 50.3G7 antibody to be efficacious in reducing significant tumor burden in bone marrow, spleen, and peripheral blood. NOD/SCID IL2R gamma-/- (NSG) mice were sub-lethally irradiated and engrafted with $5\times10^6$ EOL-1 tumor cells. Following 6 days post cell engraftment, (~0.1-1% engrafted EOL-1 cells in the bone marrow), and mice were dosed with 10 mg/kg of antibodies once per week for three weeks. Bone marrow, spleen, and blood were collected at week 4 following EOL-1 cell engraftment, and analyzed by FACS for percentage of engrafted human cells via human CD45 and CD33 antibody staining. Results from 7 to 13 mice treated with IgG control antibody or with IL1-RAP specific antibody clone 50.3G7, 56.7A9, and 56.12G6. Clone 50.3G7 gave the best efficacy relative to the other antibodies in reducing AML tumor burden in bone marrow, spleen and blood. The results are shown in FIGS. 10A-10C.

Figure 11:
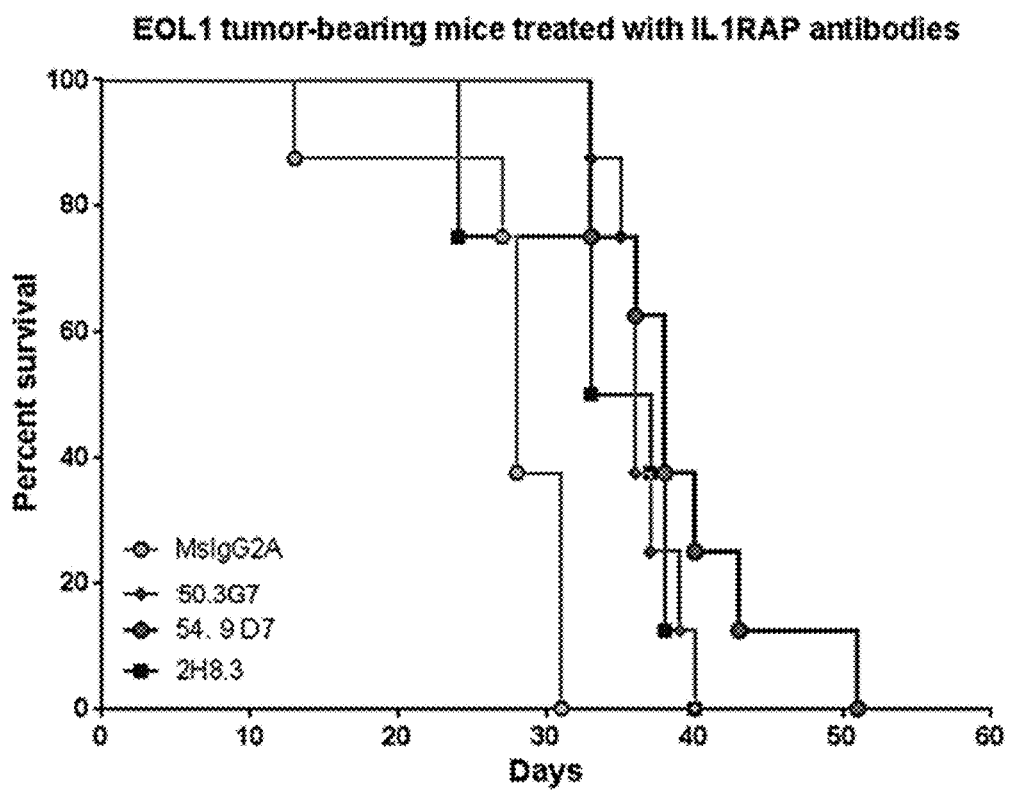
FIG. 11 is a Kaplan-Myer plot of the effect of treatment of various anti-IL1-RAP clones on survival in xenografted mice with EOL-1 tumors.

With the identification of our functional blocking IL1-RAP functional blocking antibodies, 54.9D7, 42.4D11, 42.1D2, 54.9E9, and membrane-preferential antibody, 2H8.3, we evaluated the tumor inhibition efficacy of these antibodies in vivo. Again, NSG mice were sub-lethally irradiated and engrafted with 5×10⁶ EOL-1 tumor cells. Following 6 days post cell engraftment, mice were dosed with 10 mg/kg of antibodies once per week for three weeks. Tumor-bearing mice treated with 54.9D7 antibody survived the longest relative to the other IL1-RAP antibodies with a median survival of 38 days relative to control IgG antibody treated mice only had median survival of 28 days (P value <0.00001). 54.9D7 antibody also has the best IL1-RAP signaling blocking activity, and the strong in vivo efficacy may be attributed to blocking IL1-RAP signaling to the AML cells. Clone 2H8.3, which binds preferentially to membrane-bound IL1-RAP, also produced significant survival improvement relative to control IgG antibody (median survival of 35 days for 2H8.3 vs. 28 days for IgG; P value=0.014). The 50.3G7 antibody which previously identified as an effective tumor inhibition antibody consistently gave significant survival enhancement, median of 36 days for 50.3G7 vs. 28 days for IgG; P value <0.0001). The survival curves and statistics for select anti-IL1-RAP clones are shown in FIG. 11. Clones 54.9D7, 50.3G7, and 2H8.3 are highlighted.

Example 8

Humanized Clones of Antibody 54.9D7

Three humanized versions of antibody 54.9D7 were produced and tested. Sequences and activity are depicted in FIGS. 14-19. The mean fluorescent intensity (MFI) values of the humanized clones for binding to EOL-1 cells are shown in Table 4. The $K_D$, $k_{on}$ and $k_{dis}$ values of the humanized colones are showin in Tables 5A and 5B. Clone "hH1L3" refers to a humanized clone of 54.9D7 having a heavy chain variable region sequence of SEQ ID NO: 118 and a light chain variable region sequence of SEQ ID NO: 117. Clone "hH2L3" refers to a humanized clone of 54.9D7 having a heavy chain variable region sequence of SEQ ID NO: 119 and a light chain variable region sequence of SEQ ID NO: 117. Clone "hH3L3" refers to a humanized clone of 54.9D7 having a heavy chain variable region sequence of SEQ ID NO: 120 and a light chain variable region sequence of SEQ ID NO: 117.

TABLE 4

|  | Chi54.9D7 | hH1L3 | hH2L3 | hH3L3 |
|---|---|---|---|---|
| EC50 | 160 | 114.2 | 112.6 | 108.2 |

TABLE 5A

| Clone | $K_D$ (M) | $k_{on}$ (1/Ms) | $k_{dis}$ (1/s) |
|---|---|---|---|
| Chi54.9D7 | <1.0E-12 | 1.43E+05 | <1.0E-07 |
| 54.9D7 H1L3 | 5.56E-10 | 1.36E+05 | 7.57E-05 |
| 54.9D7 H2L3 | <1.0E-12 | 1.41E+05 | <1.0E-07 |
| 54.9D7 H3L3 | <1.0E-12 | 1.77E+05 | <1.0E-07 |

TABLE 5B

| Clone | $K_D$ (M) | $k_{on}$ (1/Ms) | $k_{dis}$ (1/s) |
|---|---|---|---|
| Chi54.9D7 | <1.0E-12 | 1.58E+05 | <1.0E-07 |
| 54.9D7 H1L3 | 2.29E-10 | 1.64E+05 | 3.75E-05 |
| 54.9D7 H2L3 | <1.0E-12 | 1.69E+05 | <1.0E-07 |
| 54.9D7 H3L3 | <1.0E-12 | 1.93E+05 | <1.0E-07 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

What is claimed is:

1. An isolated anti-interleukin-1 receptor accessory protein (IL1-RAP) antibody comprising a variable light chain and a variable heavy chain, wherein:
   (a) the variable light chain comprises (i) a CDR L1 comprising SEQ ID NO: 10, (ii) a CDR L2 comprising SEQ ID NO: 11, and (iii) a CDR L3 comprising SEQ ID NO: 12; and the variable heavy chain comprises (i) a CDR H1 comprising SEQ ID NO: 7, (ii) a CDR H2 comprising SEQ ID NO: 8, and (iii) a CDR H3 comprising SEQ ID NO: 9 or the sequence comprising amino acids 99-112 of SEQ ID NO: 121; or
   (b) the variable light chain comprises (i) a CDR L1 comprising SEQ ID NO: 18, (ii) a CDR L2 comprising SEQ ID NO: 19, and (iii) a CDR L3 comprising SEQ ID NO: 20; and the variable heavy chain comprises (i) a CDRH1 comprising SEQ ID NO: 15, (ii) a CDR H2 comprising SEQ ID NO: 16, and (iii) a CDR H3 comprising SEQ ID NO: 17; or
   (c) the variable light chain comprises (i) a CDRL1 comprising SEQ ID NO: 24, (ii) a CDRL2 comprising SEQ ID NO: 25, (iii) a CDRL3 comprising SEQ ID NO: 26; and the variable heavy chain comprises (i) a CDRH1 comprising SEQ ID NO: 21, (ii) a CDRH2 comprising SEQ ID NO: 22, and (iii) a CDRH3 comprising SEQ ID NO: 23; or
   (d) the variable light chain comprises (i) a CDR L1 comprising SEQ ID NO: 32, (ii) a CDR L2 comprising SEQ ID NO: 33, (iii) a CDR L3 comprising SEQ ID NO: 34; and the variable heavy chain comprises (i) a CDR H1 comprising SEQ ID NO: 29, (ii) a CDR H2 comprising SEQ ID NO: 30, and a CDR H3 comprising SEQ ID NO: 31; or
   (e) the variable light chain comprises (i) a CDR L1 comprising SEQ ID NO: 38, (ii) a CDR L2 comprising SEQ ID NO: 39, (iii) a CDR L3 comprising SEQ ID NO: 40; and the variable heavy chain comprises (i) a CDR H1 comprising SEQ ID NO: 35, (ii) a CDR H2 comprising SEQ ID NO: 36, and a CDR H3 comprising SEQ ID NO: 37; or
   (f) the variable light chain comprises (i) a CDR L1 comprising SEQ ID NO: 45, (ii) a CDR L2 comprising SEQ ID NO: 33, (iii) a CDR L3 comprising SEQ ID NO: 46; and the variable heavy chain comprises (i) a CDR H1 comprising SEQ ID NO: 43, (ii) a CDR H2 comprising SEQ ID NO: 22, and a CDR H3 comprising SEQ ID NO: 44; or
   (g) the variable light chain comprises (i) a CDR L1 comprising SEQ ID NO: 50, (ii) a CDR L2 comprising SEQ ID NO: 39, (iii) a CDR L3 comprising SEQ ID NO: 51; and the variable heavy chain comprises (i) a CDR H1 comprising SEQ ID NO: 47, (ii) a CDR H2 comprising SEQ ID NO: 48, and a CDR H3 comprising SEQ ID NO: 49; or
   (h) the variable light chain comprises (i) a CDR L1 comprising SEQ ID NO: 56, (ii) a CDR L2 comprising SEQ ID NO: 19, (iii) a CDR L3 comprising SEQ ID NO: 57; and the variable heavy chain comprises (i) a CDR H1 comprising SEQ ID NO: 54, (ii) a CDR H2 comprising SEQ ID NO: 22, and a CDR H3 comprising SEQ ID NO: 55; or
   (i) the variable light chain comprises (i) a CDR L1 comprising SEQ ID NO: 63, (ii) a CDR L2 comprising SEQ ID NO: 64, (iii) a CDR L3 comprising SEQ ID NO: 65; and the variable heavy chain comprises (i) a CDR H1 comprising SEQ ID NO: 60, (ii) a CDR H2 comprising SEQ ID NO: 61, and a CDR H3 comprising SEQ ID NO: 62; or
   (j) the variable light chain comprises (i) a CDR L1 comprising SEQ ID NO: 72, (ii) a CDR L2 comprising SEQ ID NO: 73, (iii) a CDR L3 comprising SEQ ID NO: 74; and the variable heavy chain comprises (i) a CDR H1 comprising SEQ ID NO: 69, (ii) a CDR H2 comprising SEQ ID NO: 70, and a CDR H3 comprising SEQ ID NO: 71; or
   (k) the variable light chain comprises (i) a CDR L1 comprising SEQ ID NO: 78, (ii) a CDR L2 comprising SEQ ID NO: 79, (iii) a CDR L3 comprising SEQ ID NO: 80; and the variable heavy chain comprises (i) a CDR H1 comprising SEQ ID NO: 60, (ii) a CDR H2 comprising SEQ ID NO: 22, and a CDR H3 comprising SEQ ID NO: 77; or (l) the variable light chain comprises (i) a CDR L1 comprising SEQ ID NO: 86, (ii) a CDR L2 comprising SEQ ID NO: 87, (iii) a CDR L3 comprising SEQ ID NO: 88; and the variable heavy chain comprises (i) a CDR H1 comprising SEQ ID NO: 83, (ii) a CDR H2 comprising SEQ ID NO: 84, and a CDR H3 comprising SEQ ID NO: 85; or (m) the variable light chain comprises (i) a CDR L1 comprising SEQ ID NO: 94, (ii) a CDR L2 comprising SEQ ID NO: 95, (iii) a CDR L3 comprising SEQ ID NO: 96; and the variable heavy chain comprises (i) a CDR H1 comprising SEQ ID NO: 91, (ii) a CDR H2 comprising SEQ ID NO: 92, and a CDR H3 comprising SEQ ID NO: 93; or (n) the variable light chain comprises (i) a CDR L1 comprising SEQ ID NO: 102, (ii) a CDR L2 comprising SEQ ID NO: 103, (iii) a CDR L3 comprising SEQ ID NO: 104; and the variable heavy chain comprises (i) a CDR H1 comprising SEQ ID NO: 99, (ii) a CDR H2 comprising SEQ ID NO: 100, and a CDR H3 comprising SEQ ID NO: 101; or (o) the variable light chain comprises (i) a CDR L1 comprising SEQ ID NO: 110, (ii) a CDR L2 comprising SEQ ID NO: 111, (iii) a CDR L3 comprising SEQ ID NO: 112; and the variable heavy chain comprises (i) a CDR H1 comprising SEQ ID NO: 107, (ii) a CDR H2 comprising SEQ ID NO: 108, and a CDR H3 comprising SEQ ID NO: 109.

2. The isolated anti-IL1-RAP antibody of claim 1, comprising :

(a) the CDR L1, the CDR L2, the CDR L3, the CDR H1, the CDR H2, and a CDR H3 of claim 1(a), wherein the variable light chain comprises a sequence having at least 90% sequence identity to the sequence of SEQ ID NO: 5, SEQ ID NO: 115, SEQ ID NO: 116, or SEQ ID NO: 117; and the variable heavy chain comprises a sequence having at least 90% sequence identity to the sequence of SEQ ID NO: 6, SEQ ID NO: 118, SEQ ID NO: 119, SEQ ID NO: 120, or SEQ ID NO: 121; or (b) the CDR L1, the CDR L2, the CDR L3, the CDR H1, the CDR H2, and the CDR H3 of claim 1(b), wherein the variable light chain comprises a sequence having at least 90% sequence identity to the sequence of SEQ ID NO: 13; and the variable heavy chain comprises a sequence having at least 90% sequence identity to the sequence of SEQ ID NO: 14 or SEQ ID NO: 66; or c) the CDR L1, the CDR L2, the CDR L3, the CDR H1, the CDR H2, and the CDR H3 of claim 1(c), wherein the variable light chain comprises a sequence having at least 90% sequence identity to the sequence of SEQ ID NO: 126; and the variable heavy chain comprises a sequence having at least 90% sequence identity to the sequence of SEQ ID NO: 127; or (d) the CDR L1, the CDR L2, the CDR L3, the CDR H1, the CDR H2, and the CDR H3 of claim 1(d), wherein the variable light chain comprises a sequence having at least 90% sequence identity to the sequence of SEQ ID NO: 27 or SEQ ID NO: 122; and the variable heavy chain comprises a sequence having at least 90% sequence identity to the sequence of SEQ ID NO: 134 or SEQ ID NO: 123; or e) the CDR L1, the CDR L2, the CDR L3, the CDR H1, the CDR H2, and the CDR H3 of claim 1(e), wherein the variable light chain comprises a sequence having at least 90% sequence identity to the sequence of SEQ ID NO: 128; and the variable heavy chain comprises a sequence having at least 90% sequence identity to the sequence of SEQ ID NO: 129; or (f) the CDR L1, the CDR L2, the CDR L3, the CDR H1, the CDR H2, and the CDR H3 of claim 1(f), wherein the variable light chain comprises a sequence having at least 90% sequence identity to the sequence of SEQ ID NO: 41; and the variable heavy chain comprises a sequence having at least 90% sequence identity to the sequence of SEQ ID NO: 42; or (g) the CDR L1, the CDR L2, the CDR L3, the CDR H1, the CDR H2, and the CDR H3 of claim 1(g), wherein the variable light chain comprises a sequence having at least 90% sequence identity to the sequence of SEQ ID NO: 130; and the variable heavy chain comprises a sequence having at least 90% sequence identity to the sequence of SEQ ID NO: 131; or (h) the CDR L1, the CDR L2, the CDR L3, the CDR H1, the CDR H2, and the CDR H3 of claim 1(h), wherein the variable light chain comprises a sequence having at least 90% sequence identity to the sequence of SEQ ID NO: 52; and the variable heavy chain comprises a sequence having at least 90% sequence identity to the sequence of SEQ ID NO: 53; or (i) the CDR L1, the CDR L2, the CDR L3, the CDR H1, the CDR H2, and the CDR H3 of claim 1(i), wherein the variable light chain comprises a sequence having at least 90% sequence identity to the sequence of SEQ ID NO: 58; and the variable heavy chain comprises a sequence having at least 90% sequence identity to the sequence of SEQ ID NO: 59; or (j) the CDR L1, the CDR L2, the CDR L3, the CDR H1, the CDR H2, and the CDR H3 of claim 1(j), wherein the variable light chain comprises a sequence having at least 90% sequence identity to the sequence of SEQ ID NO: 67; and the variable heavy chain comprises a sequence having at least 90% sequence identity to the sequence of SEQ ID NO: 68; or (k) the CDR L1, the CDR L2, the CDR L3, the CDR H1, the CDR H2, and the CDR H3 of claim 1(k), wherein the variable light chain comprises a sequence having at least 90% sequence identity to the sequence of SEQ ID NO: 75; and the variable heavy chain comprises a sequence having at least 90% sequence identity to the sequence of SEQ ID NO: 76; or (l) the CDR L1, the CDR L2, the CDR L3, the CDR H1, the CDR H2, and the CDR H3 of claim 1(l), wherein the variable light chain comprises a sequence having at least 90% sequence identity to the sequence of SEQ ID NO: 81; and the variable heavy chain comprises a sequence having at least 90% sequence identity to the sequence of SEQ ID NO: 82; or (m) the CDR L1, the CDR L2, the CDR L3, the CDR H1, the CDR H2, and the CDR H3 of claim 1(m), wherein the variable light chain comprises a sequence having at least 90% sequence identity to the sequence of SEQ ID NO: 89; and the variable heavy chain comprises a sequence having at least 90% sequence identity to the sequence of SEQ ID NO: 90; or (n) the CDR L1, the CDR L2, the CDR L3, the CDR H1, the CDR H2, and the CDR H3 of claim 1(n), wherein the variable light chain comprises a sequence having at least 90% sequence identity to the sequence of SEQ ID NO: 97; and the variable heavy chain comprises a sequence having at least 90% sequence identity to the sequence of SEQ ID NO: 98; or (o) the CDR L1, the CDR L2, the CDR L3, the CDR H1, the CDR H2, and the CDR H3 of claim 1(o), wherein the variable light chain comprises a sequence having at least 90% sequence identity to the sequence of SEQ ID NO: 105; and the variable heavy chain comprises a sequence having at least 90% sequence identity to the sequence of SEQ ID NO: 106.

3. The isolated anti-IL1-RAP antibody of claim 1, wherein the light chain variable region comprises a CDR L1, a CDR L2, and a CDR L3 and the heavy chain variable region comprises a CDR H1, a CDR H2, and a CDR H3, wherein
  the CDR L1 comprises SEQ ID NO: 10,
  the CDR L2 comprises SEQ ID NO: 11,
  the CDR L3 comprises SEQ ID NO: 12,
  the CDR H1 comprises SEQ ID NO: 7,
  the CDR H2 comprises SEQ ID NO: 8, and
  the CDR H3 comprises SEQ ID NO: 9 or the sequence comprising amino acids 99-112 of SEQ ID NO: 121.

4. The isolated anti-IL1-RAP antibody of claim 3, wherein the light chain variable region comprises a sequence having at least 90% sequence identity to the sequence of SEQ ID NO: 5, SEQ ID NO: 115, SEQ ID NO: 116, or SEQ ID NO: 117.

5. The isolated anti-IL1-RAP antibody of claim 3, wherein the heavy chain variable region comprises a sequence having at least 90% sequence identity to the sequence of SEQ ID NO: 6, SEQ ID NO: 118, SEQ ID NO: 119, SEQ ID NO: 120, or SEQ ID NO: 121.

6. The isolated anti-IL1-RAP antibody of claim 1, wherein the light chain variable region comprises a CDR L1, a CDR L2, and a CDR L3 and the heavy chain variable region comprises a CDR H1, a CDR H2, and a CDR H3, wherein
  the CDR L1 comprises SEQ ID NO: 32,
  the CDR L2 comprises SEQ ID NO: 33,
  the CDR L3 comprises SEQ ID NO: 34,
  the CDR H1 comprises SEQ ID NO: 29,
  the CDR H2 comprises SEQ ID NO: 30, and
  the CDR H3 comprises SEQ ID NO: 31.

7. The isolated anti-IL1-RAP antibody of claim 6, wherein the light chain variable region comprises a sequence having at least 90% sequence identity to the sequence of SEQ ID NO: 27 or SEQ ID NO: 122.

8. The isolated anti-IL1-RAP antibody of claim 6, wherein the heavy chain variable region comprises a sequence having at least 90% sequence identity to the sequence of SEQ ID NO: 134 or SEQ ID NO: 123.

9. The isolated anti-IL1-RAP antibody of claim 1, wherein the antibody is multispecific or bispecific, and wherein the isolated anti-IL1-RAP antibody binds to an antigen selected from the group consisting of: CD45, CD38, and CD34.

10. The isolated anti-IL1-RAP antibody of claim 1, wherein the isolated anti-IL1-RAP antibody is conjugated to a chemical moiety.

11. The isolated anti-IL1-RAP antibody of claim 1, wherein the light chain variable region comprises a CDR L1, a CDR L2, and a CDR L3 and the heavy chain variable region comprises a CDR H1, a CDR H2, and a CDR H3, wherein
  the CDR L1 comprises SEQ ID NO: 24,
  the CDR L2 comprises SEQ ID NO: 25,
  the CDR L3 comprises SEQ ID NO: 26,
  the CDR H1 comprises SEQ ID NO: 21,
  the CDR H2 comprises SEQ ID NO: 22, and
  the CDR H3 comprises SEQ ID NO: 23.

12. The isolated anti-IL1-RAP antibody of claim 1, wherein the light chain variable region comprises a sequence having at least 90% sequence identity to the sequence of SEQ ID NO: 126.

13. The isolated anti-IL1-RAP antibody of claim 11, wherein the heavy chain variable region comprises a sequence having at least 90% sequence identity to the sequence of SEQ ID NO: 127.

14. The isolated anti-IL1-RAP antibody of claim 1, wherein the light chain variable region comprises a CDR L1, a CDR L2, and a CDR L3 and the heavy chain variable region comprises a CDR H1, a CDR H2, and a CDR H3, and wherein
  the CDR L1 comprises SEQ ID NO: 18,
  the CDR L2 comprises SEQ ID NO: 19,
  the CDR L3 comprises SEQ ID NO: 20,
  the CDR H1 comprises SEQ ID NO: 15,
  the CDR H2 comprises SEQ ID NO: 16, and
  the CDR H3 comprises SEQ ID NO: 17.

15. The isolated anti-IL1-RAP antibody of claim 14, wherein the light chain variable region comprises a sequence having at least 90% sequence identity to the sequence of SEQ ID NO: 13.

16. The isolated anti-IL1-RAP antibody of claim 14, wherein the heavy chain variable region comprises a sequence having at least 90% sequence identity to the sequence of SEQ ID NO: 14.

17. A pharmaceutical composition comprising the antibody of claim 1 and an adjuvant.

* * * * *

UNITED STATES PATENT AND TRADEMARK OFFICE
CERTIFICATE OF CORRECTION

PATENT NO. : 11,359,025 B2
APPLICATION NO. : 16/342176
DATED : June 14, 2022
INVENTOR(S) : Ying Ping Jiang, Jagath R. Junutula and Leonard G. Presta It is certified that error appears in the above-identified patent and that said Letters Patent is hereby corrected as shown below:

In the Specification

Column 45, Lines 48-60:
"57.7A9 light chain variable region sequence: SEQ ID NO: 66
QVQLQQPGAELVKPGASVTLSCEASGYTFTSYWIHWVKQRPGQGLEWIGEINPSHGHTTYNE
KFKNKATLTVDKSSSTAYMQVSSLTSEDSAVYYCTRHYGSYYFDLWGQGTTLTVSS 57.7A9 heavy chain variable region sequence: SEQ ID NO: 59
EVQLQQSGPELVKPGDSVKMSCKASGYTFTDYYMDWVKQSHGKSLEWIGYIYPHNGGTTYN
QKFKGKATLTVDKSSSTAYMELHSLTSEDSAVYYCARSPFNYKDPMDWWGQGTSVTVSS"

Should read:
--57.7A9 light chain variable region sequence: SEQ ID NO: 13
QIVLTQSPAIMSAFPGEKVTMTCRASSSVSYMHWYRQKSGTFPKRWIYDTSKLASGVPARFS
GSGSGTSYSLTISSMEAEDAATYYCQQWSTNPITFGAGTKLELK 57.7A9 heavy chain variable region sequence: SEQ ID NO: 66
QVQLQQPGAELVKPGASVTLSCEASGYTFTSYWIHWVKQRPGQGLEWIGEINPSHGHTTYNE
KFKNKATLTVDKSSSTAYMQVSSLTSEDSAVYYCTRHYGSYYFDLWGQGTTLTVSS--

Column 67, Line 20, in Table 2, "Tote" should read --Total--

Column 67, Line 28, "Epitope Mappine of IL1-RAP Clones" should read --Epitope Mapping of IL1-RAP Clones--

Signed and Sealed this
Twenty-fifth Day of October, 2022

Katherine Kelly Vidal
*Director of the United States Patent and Trademark Office*

SEQUENCE LISTING

```
<160> NUMBER OF SEQ ID NOS: 139

<210> SEQ ID NO 1
<211> LENGTH: 570
<212> TYPE: PRT
<213> ORGANISM: Artificial Sequence
<220> FEATURE:
<223> OTHER INFORMATION: synthetic antibody peptide construct

<400> SEQUENCE: 1

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80
```

```
                -continued

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Ile Val Val Tyr His Val Tyr Trp Leu Glu
    370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
        435                 440                 445

Ile Val Thr Asp Glu Thr Leu Ser Phe Ile Gln Lys Ser Arg Arg Leu
    450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
```

```
                    500                 505                 510
Glu Leu Lys Arg Ala Thr Val Leu Thr Val Ile Lys Trp Lys Gly
                515                 520                 525

Glu Lys Ser Lys Tyr Pro Gln Gly Arg Phe Trp Lys Gln Leu Gln Val
            530                 535                 540

Ala Met Pro Val Lys Lys Ser Pro Arg Arg Ser Ser Asp Glu Gln
545                 550                 555                 560

Gly Leu Ser Tyr Ser Ser Leu Lys Asn Val
                565                 570

<210> SEQ ID NO 2
<211> LENGTH: 12
<212> TYPE: PRT
<213> ORGANISM: Artificial Sequence
<220> FEATURE:
<223> OTHER INFORMATION: synthetic antibody peptide construct

<400> SEQUENCE: 2

Val Pro Ala Pro Arg Tyr Thr Val Glu Leu Ala Cys
1               5                   10

<210> SEQ ID NO 3
<211> LENGTH: 36
<212> TYPE: PRT
<213> ORGANISM: Artificial Sequence
<220> FEATURE:
<223> OTHER INFORMATION: synthetic antibody peptide construct

<400> SEQUENCE: 3

His Ala Arg Ser Ala Lys Gly Glu Val Ala Lys Ala Ala Lys Val Lys
1               5                   10                  15

Gln Lys Val Pro Ala Pro Arg Tyr Thr Val Glu Leu Ala Cys Gly Phe
            20                  25                  30

Gly Ala Thr Cys
        35

<210> SEQ ID NO 4
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 4

Gly Asn Arg Cys Gly Gln
1               5

<210> SEQ ID NO 5
<211> LENGTH: 113
<212> TYPE: PRT
<213> ORGANISM: Artificial Sequence
<220> FEATURE:
<223> OTHER INFORMATION: synthetic antibody peptide construct

<400> SEQUENCE: 5

Asp Ile Val Leu Thr Gln Ser Pro Ile Ser Leu Ala Val Phe Leu Gly
1               5                   10                  15

Gln Arg Ala Thr Ile Ser Cys Arg Ala Ser Gln Ser Val Ser Thr Ser
            20                  25                  30

Gly Tyr Ser Ser Met His Trp Tyr Gln Gln Lys Ala Gly Gln Pro Pro
        35                  40                  45

Lys Leu Leu Ile Lys Tyr Ala Ser Asp Leu Glu Ser Gly Val Pro Val
```

```
                 50                  55                  60
Arg Phe Ser Gly Ser Gly Ser Gly Thr Asp Phe Ile Leu Asn Ile His
 65                  70                  75                  80

Pro Val Glu Val Glu Asp Ile Ala Thr Tyr Tyr Cys His His Ser Trp
                 85                  90                  95

Gly Ile Pro Met Tyr Thr Phe Gly Gly Gly Thr Lys Leu Glu Ile Lys
            100                 105                 110

Arg

<210> SEQ ID NO 6
<211> LENGTH: 123
<212> TYPE: PRT
<213> ORGANISM: Artificial Sequence
<220> FEATURE:
<223> OTHER INFORMATION: synthetic antibody peptide construct

<400> SEQUENCE: 6

His Val Gln Leu Gln Gln Ser Gly Pro Glu Leu Val Arg Pro Gly Ala
  1               5                  10                  15

Ser Val Lys Leu Ser Cys Lys Ala Ser Gly Tyr Ile Phe Ile Thr Tyr
                 20                  25                  30

Trp Met Asn Trp Val Lys Gln Arg Pro Gly Gln Gly Leu Glu Trp Val
             35                  40                  45

Gly Gln Ile Phe Pro Ala Ser Gly Thr Thr Tyr Tyr Asn Glu Leu Phe
         50                  55                  60

Glu Gly Lys Ala Thr Leu Thr Val Asp Thr Ser Ser Asn Thr Ala Tyr
 65                  70                  75                  80

Met His Leu Thr Ser Leu Thr Ser Glu Asp Ser Ala Val Tyr Tyr Cys
                 85                  90                  95

Ala Arg Thr Asp Phe Tyr Arg Tyr Asp Gly Gly Tyr Ala Leu Asp Tyr
            100                 105                 110

Trp Gly Gln Gly Thr Ser Leu Thr Val Ser Ser
        115                 120

<210> SEQ ID NO 7
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 7

Gly Tyr Ile Phe Ile Thr Tyr
  1               5

<210> SEQ ID NO 8
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 8

Phe Pro Ala Ser Gly Thr
  1               5

<210> SEQ ID NO 9
<211> LENGTH: 14
<212> TYPE: PRT
<213> ORGANISM: Artificial Sequence
<220> FEATURE:
```

```
<223> OTHER INFORMATION: synthetic antibody peptide construct

<400> SEQUENCE: 9

Thr Asp Phe Tyr Arg Tyr Asp Gly Gly Tyr Ala Leu Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: synthetic antibody peptide construct

<400> SEQUENCE: 10

Arg Ala Ser Gln Ser Val Ser Thr Ser Gly Tyr Ser Met His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 11

Tyr Ala Ser Asp Leu Glu Ser
1               5

<210> SEQ ID NO 12
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 12

His His Ser Trp Gly Ile Pro Met Tyr Thr
1               5                   10

<210> SEQ ID NO 13
<211> LENGTH: 106
<212> TYPE: PRT
<213> ORGANISM: Artificial Sequence
<220> FEATURE:
<223> OTHER INFORMATION: synthetic antibody peptide construct

<400> SEQUENCE: 13

Gln Ile Val Leu Thr Gln Ser Pro Ala Ile Met Ser Ala Phe Pro Gly
1               5                   10                  15

Glu Lys Val Thr Met Thr Cys Arg Ala Ser Ser Ser Val Ser Tyr Met
                20                  25                  30

His Trp Tyr Arg Gln Lys Ser Gly Thr Phe Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Thr Asn Pro Ile Thr
                85                  90                  95

Phe Gly Ala Gly Thr Lys Leu Glu Leu Lys
            100                 105

<210> SEQ ID NO 14
```

```
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 14

Arg Ser Asn Tyr Ser Ser Leu Gly Ala Glu Leu Val Lys Pro Gly Ala
1               5                  10                  15

Ser Val Thr Leu Ser Cys Glu Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asn Pro Ser His Gly His Thr Thr Tyr Asn Glu Lys Phe
    50                  55                  60

Lys Asn Lys Ala Thr Leu Thr Val Asp Lys Ser Ser Thr Ala Tyr
65                  70                  75                  80

Met Gln Val Ser Ser Leu Thr Ser Glu Asp Ser Ala Val Tyr Tyr Cys
                85                  90                  95

Thr Arg His Tyr Gly Ser Tyr Tyr Phe Asp Leu Trp Gly Gln Gly Thr
            100                 105                 110

Thr Leu Thr Val Ser Ser
        115

<210> SEQ ID NO 15
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 15

Gly Tyr Thr Phe Thr Ser Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 16

Asn Pro Ser His Gly His
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 17

His Tyr Gly Ser Tyr Tyr Phe Asp Leu
1               5

<210> SEQ ID NO 18
<211> LENGTH: 10
<212> TYPE: PRT
<213> ORGANISM: Artificial Sequence
<220> FEATURE:
<223> OTHER INFORMATION: synthetic antibody peptide construct
```

```
<400> SEQUENCE: 18

Arg Ala Ser Ser Ser Val Ser Tyr Met His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 19

Asp Thr Ser Lys Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 20

Gln Gln Trp Ser Thr Asn Pro Ile Thr
1               5

<210> SEQ ID NO 21
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 21

Gly Tyr Thr Phe Thr Asp Tyr Ser Met His
1               5                   10

<210> SEQ ID NO 22
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 22

Asn Thr Glu Thr Gly Glu
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 23

Tyr Tyr Gly Tyr Phe Asp Tyr
1               5

<210> SEQ ID NO 24
<211> LENGTH: 15
<212> TYPE: PRT
<213> ORGANISM: Artificial Sequence
<220> FEATURE:
<223> OTHER INFORMATION: synthetic antibody peptide construct

<400> SEQUENCE: 24
```

```
Arg Ala Ser Glu Ser Val Asp Ser Tyr Gly Asn Ser Phe Met His
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 25

Arg Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 26

Gln Gln Ser Asn Glu Asp Pro Trp Thr
1               5

<210> SEQ ID NO 27
<211> LENGTH: 108
<212> TYPE: PRT
<213> ORGANISM: Artificial Sequence
<220> FEATURE:
<223> OTHER INFORMATION: synthetic antibody peptide construct

<400> SEQUENCE: 27

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser His Asn Trp Pro His
                85                  90                  95

Thr Phe Gly Gly Gly Thr Lys Leu Glu Ile Lys Arg
            100                 105

<210> SEQ ID NO 28
<211> LENGTH: 123
<212> TYPE: PRT
<213> ORGANISM: Artificial Sequence
<220> FEATURE:
<223> OTHER INFORMATION: synthetic antibody peptide construct

<400> SEQUENCE: 28

His Val Gln Leu Gln Gln Ser Gly Pro Glu Leu Val Arg Pro Gly Ala
1               5                   10                  15

Ser Val Lys Leu Ser Cys Lys Ala Ser Gly Tyr Ile Phe Ile Thr Tyr
            20                  25                  30

Trp Met Asn Trp Val Lys Gln Arg Pro Gly Gln Gly Leu Glu Trp Val
        35                  40                  45
```

```
Gly Gln Ile Phe Pro Ala Ser Gly Thr Thr Tyr Tyr Asn Glu Leu Phe
        50                  55                  60

Glu Gly Lys Ala Thr Leu Thr Val Asp Thr Ser Asn Thr Ala Tyr
 65                  70                  75                  80

Met His Leu Thr Ser Leu Thr Ser Glu Asp Ser Ala Val Tyr Tyr Cys
                     85                  90                  95

Ala Arg Thr Asp Phe Tyr Arg Tyr Asp Gly Gly Tyr Ala Leu Asp Tyr
                100                 105                 110

Trp Gly Gln Gly Thr Ser Leu Thr Val Ser Ser
            115                 120

<210> SEQ ID NO 29
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 29

Gly Tyr Thr Phe Thr Asn Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 30

Asn Thr Tyr Thr Gly Glu
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 31

Tyr Tyr Gly Asn Phe Asp Tyr
1               5

<210> SEQ ID NO 32
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 32

Arg Ala Ser Gln Ser Ile Ser Asn Asn Leu His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 33

Tyr Ala Ser Gln Ser Ile Ser
```

<210> SEQ ID NO 34
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 34

Gln Gln Ser His Asn Trp Pro His Thr
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 35

Gly Phe Thr Phe Thr Ser Tyr
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 36

Ser Arg Gly Gly Ser His
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 37

Ala Tyr Gly Asn Ser Glu Met Asp Phe
1               5

<210> SEQ ID NO 38
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 38

Ser Ala Ser Ser Ser Ile Ser Tyr Ile His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 39

Asp Thr Ser Asn Leu Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 40

His Gln Arg Thr Tyr Tyr Pro Leu Thr
1               5

<210> SEQ ID NO 41
<211> LENGTH: 107
<212> TYPE: PRT
<213> ORGANISM: Artificial Sequence
<220> FEATURE:
<223> OTHER INFORMATION: synthetic antibody peptide construct

<400> SEQUENCE: 41

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Asp
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Arg Ile Asn Ser Val Glu Thr
65                  70                  75                  80

Glu Asp Phe Arg Met Tyr Phe Cys Gln Gln Ser Asn Asn Trp Pro Leu
                85                  90                  95

Thr Phe Gly Ala Gly Thr Lys Leu Glu Val Lys
            100                 105

<210> SEQ ID NO 42
<211> LENGTH: 116
<212> TYPE: PRT
<213> ORGANISM: Artificial Sequence
<220> FEATURE:
<223> OTHER INFORMATION: synthetic antibody peptide construct

<400> SEQUENCE: 42

Gln Ile Gln Leu Val Gln Ser Gly Pro Glu Leu Lys Lys Pro Gly Glu
1               5                   10                  15

Thr Val Asn Ile Ser Cys Lys Ala Ser Gly Tyr Thr Phe Thr Asp Phe
            20                  25                  30

Ser Met His Trp Val Lys Gln Ala Pro Gly Lys Gly Leu Gln Trp Met
        35                  40                  45

Gly Trp Ile Asn Thr Glu Thr Gly Glu Pro Thr Tyr Ala Asp Asp Phe
    50                  55                  60

Glu Ala Arg Phe Ala Phe Ser Leu Ala Thr Ser Ala Asn Thr Ala Tyr
65                  70                  75                  80

Leu Lys Ile Asn Asn Leu Lys Asn Glu Asp Thr Ala Thr Tyr Phe Cys
                85                  90                  95

Ala Arg Phe Phe Leu His Phe Asp Tyr Trp Gly Gln Gly Thr Thr Leu
            100                 105                 110

Thr Val Ser Ser
            115

```
<210> SEQ ID NO 43
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 43

Gly Tyr Thr Phe Thr Asp Phe
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 44

Phe Phe Leu His Phe Asp Tyr
1               5

<210> SEQ ID NO 45
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 45

Arg Ala Ser Gln Ser Ile Asn Asn Asp Leu His
1               5                   10

<210> SEQ ID NO 46
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 46

Gln Gln Ser Asn Asn Trp Pro Leu Thr
1               5

<210> SEQ ID NO 47
<211> LENGTH: 8
<212> TYPE: PRT
<213> ORGANISM: Artificial Sequence
<220> FEATURE:
<223> OTHER INFORMATION: synthetic antibody peptide construct

<400> SEQUENCE: 47

Gly Phe Ser Phe Ser Ser Tyr Gly
1               5

<210> SEQ ID NO 48
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 48

Thr Ser Gly Gly Ser His
1               5
```

```
<210> SEQ ID NO 49
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 49

Ser Tyr Gly Asn Tyr Val Met Asp Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 50

Ser Ala Ser Ser Ser Val Ile Tyr Ile Tyr
1               5                   10

<210> SEQ ID NO 51
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 51

Gln Gln Trp Asn Ser Tyr Pro Pro Thr
1               5

<210> SEQ ID NO 52
<211> LENGTH: 106
<212> TYPE: PRT
<213> ORGANISM: Artificial Sequence
<220> FEATURE:
<223> OTHER INFORMATION: synthetic antibody peptide construct

<400> SEQUENCE: 52

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Thr Gly Thr Ser Pro Lys Arg Leu Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Tyr Tyr Pro Leu Thr
                85                  90                  95

Phe Gly Ala Gly Ala Lys Leu Glu Leu Lys
            100                 105

<210> SEQ ID NO 53
<211> LENGTH: 116
<212> TYPE: PRT
<213> ORGANISM: Artificial Sequence
<220> FEATURE:
<223> OTHER INFORMATION: synthetic antibody peptide construct

<400> SEQUENCE: 53
```

```
Gln Ile Gln Leu Val Gln Ser Gly Pro Glu Leu Lys Lys Pro Gly Glu
 1               5                  10                  15
Thr Val Lys Ile Ser Cys Lys Ala Ser Ser Tyr Thr Phe Thr Asp Tyr
             20                  25                  30
Ser Met His Trp Val Lys Gln Ala Pro Gly Lys Gly Leu Lys Trp Met
         35                  40                  45
Gly Trp Ile Asn Thr Glu Thr Gly Glu Pro Arg Tyr Ala Asp Asp Phe
     50                  55                  60
Lys Gly Arg Phe Ala Phe Ser Leu Glu Thr Ser Ala Ser Thr Ala Tyr
 65                  70                  75                  80
Leu Gln Ile Asn Asn Leu Lys Asn Glu Asp Thr Ala Thr Tyr Phe Cys
                 85                  90                  95
Ala Arg Phe Leu Leu His Phe Asp Tyr Trp Gly Gln Gly Thr Ile Leu
             100                 105                 110
Thr Val Ser Ser
            115
```

<210> SEQ ID NO 54
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 54

```
Ser Tyr Thr Phe Thr Asp Tyr
 1               5
```

<210> SEQ ID NO 55
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 55

```
Phe Leu Leu His Phe Asp Tyr
 1               5
```

<210> SEQ ID NO 56
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 56

```
Ser Ala Ser Ser Ser Val Ser Tyr Met His
 1               5                  10
```

<210> SEQ ID NO 57
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 57

```
His Gln Arg Ser Tyr Tyr Pro Leu Thr
 1               5
```

<210> SEQ ID NO 58
<211> LENGTH: 107

```
<212> TYPE: PRT
<213> ORGANISM: Artificial Sequence
<220> FEATURE:
<223> OTHER INFORMATION: synthetic antibody peptide construct

<400> SEQUENCE: 58

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro His Leu Leu Val
        35                  40                  45

Tyr Asn Ala Glu Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 59
<211> LENGTH: 120
<212> TYPE: PRT
<213> ORGANISM: Artificial Sequence
<220> FEATURE:
<223> OTHER INFORMATION: synthetic antibody peptide construct

<400> SEQUENCE: 59

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Tyr
            20                  25                  30

Tyr Met Asp Trp Val Lys Gln Ser His Gly Lys Ser Leu Glu Trp Ile
        35                  40                  45

Gly Tyr Ile Tyr Pro His Asn Gly Gly Thr Thr Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Ser Pro Phe Asn Tyr Lys Asp Pro Met Asp Trp Trp Gly Gln
            100                 105                 110

Gly Thr Ser Val Thr Val Ser Ser
        115                 120

<210> SEQ ID NO 60
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 60

Gly Tyr Thr Phe Thr Asp Tyr
1               5

<210> SEQ ID NO 61
<211> LENGTH: 6
<212> TYPE: PRT
```

```
<213> ORGANISM: Artificial Sequence
<220> FEATURE:
<223> OTHER INFORMATION: synthetic antibody peptide construct

<400> SEQUENCE: 61

Tyr Pro His Asn Gly Gly
1               5

<210> SEQ ID NO 62
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 62

Ser Pro Phe Asn Tyr Lys Asp Pro Met Asp Trp
1               5                   10

<210> SEQ ID NO 63
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 63

Arg Ala Ser Gly Asn Ile His Asn Tyr Leu Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 64

Asn Ala Glu Thr Leu Ala Asp
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 65

Gln His Phe Trp Ser Thr Pro Trp Thr
1               5

<210> SEQ ID NO 66
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 66

Gln Val Gln Leu Gln Gln Pro Gly Ala Glu Leu Val Lys Pro Gly Ala
1               5                   10                  15

Ser Val Thr Leu Ser Cys Glu Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45
```

Gly Glu Ile Asn Pro Ser His Gly His Thr Thr Tyr Asn Glu Lys Phe
            50                  55                  60

Lys Asn Lys Ala Thr Leu Thr Val Asp Lys Ser Ser Thr Ala Tyr
 65                  70                  75                  80

Met Gln Val Ser Ser Leu Thr Ser Glu Asp Ser Ala Val Tyr Tyr Cys
                 85                  90                  95

Thr Arg His Tyr Gly Ser Tyr Tyr Phe Asp Leu Trp Gly Gln Gly Thr
                100                 105                 110

Thr Leu Thr Val Ser Ser
        115

<210> SEQ ID NO 67
<211> LENGTH: 110
<212> TYPE: PRT
<213> ORGANISM: Artificial Sequence
<220> FEATURE:
<223> OTHER INFORMATION: synthetic antibody peptide construct

<400> SEQUENCE: 67

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
                 20                  25                  30

Leu Val Trp Tyr Gln Leu Lys Gln Gly Lys Ser Pro Gln Leu Leu Val
             35                  40                  45

Tyr Ala Ala Thr Asn Leu Ala Asp Gly Val Pro Ser Arg Phe Ser Gly
         50                  55                  60

Ser Gly Ser Asp Thr Gln Tyr Ser Leu Lys Ile Asn Ser Leu Gln Ser
 65                  70                  75                  80

Glu Asp Phe Gly Ser Tyr Tyr Cys Leu His Phe Trp Gly Pro Pro Tyr
                 85                  90                  95

Met Tyr Thr Phe Gly Gly Gly Thr Asn Leu Glu Met Lys Arg
                100                 105                 110

<210> SEQ ID NO 68
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 68

Gln Val Gln Leu Gln Gln Ser Gly Pro Glu Leu Val Lys Pro Gly Ala
 1               5                  10                  15

Ser Val Lys Ile Ser Cys Thr Ala Ser Gly Tyr Ala Phe Ser Thr Ser
                 20                  25                  30

Trp Met Asn Trp Val Lys Gln Arg Pro Gly Lys Gly Leu Glu Trp Ile
             35                  40                  45

Gly Arg Ile Tyr Pro Gly Asp Gly Asp Ser Asn Tyr Asn Gly Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Arg Asp Tyr Tyr Gly Phe Phe Asp Val Trp Gly Ala Gly Thr
                100                 105                 110

Thr Val Thr Val Ser Ser

```
<210> SEQ ID NO 69
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 69

Gly Tyr Ala Phe Ser Thr Ser
1               5

<210> SEQ ID NO 70
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 70

Tyr Pro Gly Asp Gly Asp
1               5

<210> SEQ ID NO 71
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 71

Arg Asp Tyr Tyr Gly Phe Phe Asp Val
1               5

<210> SEQ ID NO 72
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 72

Arg Ala Ser Glu Asn Ile Tyr Ser Asn Leu Val
1               5                   10

<210> SEQ ID NO 73
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 73

Ala Ala Thr Asn Leu Ala Asp
1               5

<210> SEQ ID NO 74
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 74

Leu His Phe Trp Gly Pro Pro Tyr Met Tyr Thr
1               5                   10
```

```
<210> SEQ ID NO 75
<211> LENGTH: 112
<212> TYPE: PRT
<213> ORGANISM: Artificial Sequence
<220> FEATURE:
<223> OTHER INFORMATION: synthetic antibody peptide construct

<400> SEQUENCE: 75

Asp Ile Val Met Thr Gln Ala Ala Phe Ser Asn Pro Val Thr Leu Gly
1               5                   10                  15

Thr Ser Ala Ser Ile Ser Cys Arg Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Phe Thr Phe Gly Ser Gly Thr Lys Leu Glu Ile Lys
            100                 105                 110

<210> SEQ ID NO 76
<211> LENGTH: 117
<212> TYPE: PRT
<213> ORGANISM: Artificial Sequence
<220> FEATURE:
<223> OTHER INFORMATION: synthetic antibody peptide construct

<400> SEQUENCE: 76

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Glu Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ser Phe Pro Trp Phe Thr Tyr Trp Gly Gln Gly Thr Leu
            100                 105                 110

Val Thr Val Ser Ala
        115

<210> SEQ ID NO 77
<211> LENGTH: 8
<212> TYPE: PRT
<213> ORGANISM: Artificial Sequence
<220> FEATURE:
<223> OTHER INFORMATION: synthetic antibody peptide construct

<400> SEQUENCE: 77

Gly Ser Phe Pro Trp Phe Thr Tyr
1               5
```

```
<210> SEQ ID NO 78
<211> LENGTH: 16
<212> TYPE: PRT
<213> ORGANISM: Artificial Sequence
<220> FEATURE:
<223> OTHER INFORMATION: synthetic antibody peptide construct

<400> SEQUENCE: 78

Arg Ser Ser Lys Ser Leu Leu His Ser Asn Gly Ile Thr Tyr Leu Tyr
1               5                   10                  15

<210> SEQ ID NO 79
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 79

Gln Met Ser Asn Leu Ala Ser
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 80

Ala Gln Asn Leu Glu Leu Pro Phe Thr
1               5

<210> SEQ ID NO 81
<211> LENGTH: 107
<212> TYPE: PRT
<213> ORGANISM: Artificial Sequence
<220> FEATURE:
<223> OTHER INFORMATION: synthetic antibody peptide construct

<400> SEQUENCE: 81

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Ser Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Tyr Leu Pro Trp
                85                  90                  95

Thr Phe Gly Gly Gly Thr Lys Leu Glu Ile Lys
            100                 105

<210> SEQ ID NO 82
<211> LENGTH: 119
<212> TYPE: PRT
<213> ORGANISM: Artificial Sequence
<220> FEATURE:
<223> OTHER INFORMATION: synthetic antibody peptide construct

<400> SEQUENCE: 82
```

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Gly Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asn Thr Asn Tyr Tyr Gly Glu Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Asn Asp Gly Tyr Pro Ala Trp Phe Thr Tyr Trp Gly Gln Gly
                100                 105                 110

Thr Leu Val Thr Val Ser Ala
        115
```

```
<210> SEQ ID NO 83
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 83

Gly Tyr Gly Phe Ser Ser Ser
1               5
```

```
<210> SEQ ID NO 84
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 84

Tyr Pro Gly Asp Gly Asn
1               5
```

```
<210> SEQ ID NO 85
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 85

Asn Asp Gly Tyr Pro Ala Trp Phe Thr Tyr
1               5                   10
```

```
<210> SEQ ID NO 86
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 86

Ser Ala Ser Gln Gly Ile Ser Asn Tyr Leu Asn
1               5                   10
```

```
<210> SEQ ID NO 87
```

```
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 87

Tyr Thr Ser Thr Leu His Ser
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 88

Gln Gln Tyr Ser Tyr Leu Pro Trp Thr
1               5

<210> SEQ ID NO 89
<211> LENGTH: 112
<212> TYPE: PRT
<213> ORGANISM: Artificial Sequence
<220> FEATURE:
<223> OTHER INFORMATION: synthetic antibody peptide construct

<400> SEQUENCE: 89

Asp Ser Val Leu Thr Gln Ser Leu Thr Ser Leu Val Val Ser Leu Gly
1               5                   10                  15

Gln Arg Ala Thr Ile Ser Cys Arg Ala Ser Glu Ser Val Asp Asn His
            20                  25                  30

Gly Asn Ser Phe Met His Trp Tyr Gln Gln Lys Pro Gly Gln Pro Pro
        35                  40                  45

Lys Leu Leu Ile Phe Leu Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Gly Asp Glu Gly Ala Thr Tyr Tyr Cys His Gln Ile Asn
                85                  90                  95

Ala His Pro Tyr Thr Phe Gly Gly Gly Thr Lys Leu Glu Ile Lys Arg
            100                 105                 110

<210> SEQ ID NO 90
<211> LENGTH: 120
<212> TYPE: PRT
<213> ORGANISM: Artificial Sequence
<220> FEATURE:
<223> OTHER INFORMATION: synthetic antibody peptide construct

<400> SEQUENCE: 90

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Val Gly Val Gly Trp Ile Arg Gln Pro Ser Gly Lys Gly Leu Glu
        35                  40                  45

Trp Leu Ala His Ile Trp Trp Asp Asp Lys Tyr Tyr Lys Ser Ala
    50                  55                  60

Leu Lys Ser Arg Leu Thr Ile Ser Lys Asp Thr Ser Lys Asn Gln Val
65                  70                  75                  80
```

```
Phe Leu Lys Ile Ala Asn Val Asp Thr Ala Asp Thr Ala Thr Tyr Phe
                85                  90                  95
Cys Ala Arg Leu Lys Leu Gly Pro Tyr Tyr Phe Asp Tyr Trp Gly Gln
            100                 105                 110
Gly Thr Thr Leu Thr Val Ser Ser
        115                 120

<210> SEQ ID NO 91
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 91

Gly Phe Ser Leu Ser Thr Phe Gly Val
1               5

<210> SEQ ID NO 92
<211> LENGTH: 5
<212> TYPE: PRT
<213> ORGANISM: Artificial Sequence
<220> FEATURE:
<223> OTHER INFORMATION: synthetic antibody peptide construct

<400> SEQUENCE: 92

Trp Trp Asp Asp Asp
1               5

<210> SEQ ID NO 93
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 93

Leu Lys Leu Gly Pro Tyr Tyr Phe Asp Tyr
1               5                   10

<210> SEQ ID NO 94
<211> LENGTH: 15
<212> TYPE: PRT
<213> ORGANISM: Artificial Sequence
<220> FEATURE:
<223> OTHER INFORMATION: synthetic antibody peptide construct

<400> SEQUENCE: 94

Arg Ala Ser Glu Ser Val Asp Asn His Gly Asn Ser Phe Met His
1               5                   10                  15

<210> SEQ ID NO 95
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 95

Leu Ala Ser Asn Leu Glu Ser
1               5

<210> SEQ ID NO 96
<211> LENGTH: 9
<212> TYPE: PRT
```

<213> ORGANISM: Artificial Sequence
<220> FEATURE:
<223> OTHER INFORMATION: synthetic antibody peptide construct

<400> SEQUENCE: 96

```
His Gln Ile Asn Ala His Pro Tyr Thr
1               5
```

<210> SEQ ID NO 97
<211> LENGTH: 106
<212> TYPE: PRT
<213> ORGANISM: Artificial Sequence
<220> FEATURE:
<223> OTHER INFORMATION: synthetic antibody peptide construct

<400> SEQUENCE: 97

```
Gln Ile Val Leu Thr Gln Ser Pro Ala Ile Met Ser Ala Ser Pro Gly
1               5                   10                  15

Glu Lys Val Thr Met Thr Cys Ser Ala Arg Ser Ser Val Asp Tyr Met
                20                  25                  30

Tyr Trp Tyr Gln Gln Lys Pro Gly Ser Ser Pro Arg Leu Leu Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Val Arg Val Glu Ala Glu
65                  70                  75                  80

Asp Ala Ala Thr Tyr Tyr Cys Gln Gln Trp Asn Thr Tyr Pro Leu Thr
                85                  90                  95

Phe Gly Ala Gly Thr Lys Leu Glu Leu Lys
            100                 105
```

<210> SEQ ID NO 98
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 98

```
Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
                20                  25                  30

Tyr Met Ser Trp Val Arg Gln Thr Pro Glu Lys Arg Leu Glu Trp Val
            35                  40                  45

Ala Thr Ile Ser Asn Ser Gly Gly Ser Thr Tyr Tyr Ala Asp Ser Val
        50                  55                  60

Lys Asp Arg Phe Thr Ile Ser Arg Asp Ser Ala Lys Asn Thr Leu Tyr
65                  70                  75                  80

Leu Gln Met Asn Ser Leu Ile Ser Glu Asp Thr Ala Val Tyr Tyr Cys
                85                  90                  95

Ala Leu Tyr Tyr Gly Asn Phe Gly Phe Asp Tyr Trp Gly Gln Gly Thr
            100                 105                 110

Ser Leu Thr Val Ser Ser
        115
```

<210> SEQ ID NO 99
<211> LENGTH: 7
<212> TYPE: PRT
<213> ORGANISM: Artificial Sequence -continued

```
<220> FEATURE:
<223> OTHER INFORMATION: synthetic antibody peptide construct

<400> SEQUENCE: 99

Gly Phe Thr Phe Ser Ser Tyr
1               5

<210> SEQ ID NO 100
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 100

Ser Asn Ser Gly Gly Ser
1               5

<210> SEQ ID NO 101
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 101

Tyr Tyr Gly Asn Phe Gly Phe Asp Tyr
1               5

<210> SEQ ID NO 102
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 102

Ser Ala Arg Ser Ser Val Asp Tyr Met Tyr
1               5                   10

<210> SEQ ID NO 103
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 103

Ala Thr Ser Asn Leu Ala Ser
1               5

<210> SEQ ID NO 104
<211> LENGTH: 9
<212> TYPE: PRT
<213> ORGANISM: Artificial Sequence
<220> FEATURE:
<223> OTHER INFORMATION: synthetic antibody peptide construct

<400> SEQUENCE: 104

Gln Gln Trp Asn Thr Tyr Pro Leu Thr
1               5

<210> SEQ ID NO 105
<211> LENGTH: 109
<212> TYPE: PRT
<213> ORGANISM: Artificial Sequence
<220> FEATURE:
```

<223> OTHER INFORMATION: synthetic antibody peptide construct

<400> SEQUENCE: 105

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Ser Gly Gln Ser Pro Lys Leu Leu Ile
        35                  40                  45

Tyr Trp Ala Ser Thr Arg His Thr Glu Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Tyr Pro Leu
                85                  90                  95

Tyr Thr Phe Gly Gly Gly Thr Lys Leu Glu Ile Lys Arg
            100                 105

<210> SEQ ID NO 106
<211> LENGTH: 104
<212> TYPE: PRT
<213> ORGANISM: Artificial Sequence
<220> FEATURE:
<223> OTHER INFORMATION: synthetic antibody peptide construct

<400> SEQUENCE: 106

Thr Val Val Asp Ser Gly Lys Cys Arg Ser Lys Gly Phe Gly Tyr Thr
1               5                   10                  15

Leu Gly Gly Cys Gly Val Leu Trp Ser Lys Gln Arg Pro Gly Gln Gly
            20                  25                  30

Leu Glu Trp Ile Gly Glu Ile Asn Pro Ser Asn Gly Phe Thr Asn Tyr
        35                  40                  45

Asn Glu Lys Phe Asn Tyr Lys Ala Thr Leu Thr Val Asp Lys Ser Ser
    50                  55                  60

Ser Thr Ala Tyr Met Gln Leu Ser Ser Leu Thr Ser Ala Asp Ser Ala
65                  70                  75                  80

Val Tyr Tyr Cys Thr Thr Gly His Tyr Phe Asp Tyr Trp Gly Gln
                85                  90                  95

Gly Thr Thr Leu Thr Val Ser Ser
            100

<210> SEQ ID NO 107
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 107

Gly Tyr Thr Leu Gly Gly Cys
1               5

<210> SEQ ID NO 108
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 108

Asn Pro Ser Asn Gly Phe
1               5

<210> SEQ ID NO 109
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 109

Gly Gly His Tyr Phe Asp Tyr
1               5

<210> SEQ ID NO 110
<211> LENGTH: 11
<212> TYPE: PRT
<213> ORGANISM: Artificial Sequence
<220> FEATURE:
<223> OTHER INFORMATION: synthetic antibody peptide construct

<400> SEQUENCE: 110

Lys Ala Ser Gln Asp Val Gly Thr Ala Val Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: synthetic antibody peptide construct

<400> SEQUENCE: 111

Trp Ala Ser Thr Arg His Thr
1               5

<210> SEQ ID NO 112
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 112

Gln Gln Tyr Ser Ser Tyr Pro Leu Tyr Thr
1               5                   10

<210> SEQ ID NO 113
<211> LENGTH: 356
<212> TYPE: PRT
<213> ORGANISM: Artificial Sequence
<220> FEATURE:
<223> OTHER INFORMATION: synthetic antibody peptide construct

<400> SEQUENCE: 113

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

```
Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln
        355

<210> SEQ ID NO 114
<211> LENGTH: 350
<212> TYPE: PRT
<213> ORGANISM: Artificial Sequence
<220> FEATURE:
<223> OTHER INFORMATION: synthetic antibody peptide construct

<400> SEQUENCE: 114

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80
```

```
Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu His Val Val Tyr
    290                 295                 300

Glu Lys Glu Pro Gly Glu Glu Leu Leu Ile Pro Cys Thr Val Tyr Phe
305                 310                 315                 320

Ser Phe Leu Met Asp Ser Arg Asn Glu Val Trp Trp Thr Ile Asp Gly
                325                 330                 335

Lys Lys Pro Asp Asp Ile Thr Ile Asp Val Thr Ile Asn Glu
            340                 345                 350

<210> SEQ ID NO 115
<211> LENGTH: 113
<212> TYPE: PRT
<213> ORGANISM: Artificial Sequence
<220> FEATURE:
<223> OTHER INFORMATION: synthetic antibody peptide construct

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Gly Tyr Ser Ser Met His Trp Tyr Gln Gln Lys Pro Gly Lys Ala Pro
        35                  40                  45

Lys Leu Leu Ile Tyr Tyr Ala Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His His Ser Trp
                85                  90                  95
```

```
Gly Ile Pro Met Tyr Thr Phe Gly Gln Gly Thr Lys Leu Glu Ile Lys
                100                 105                 110
Arg

<210> SEQ ID NO 116
<211> LENGTH: 113
<212> TYPE: PRT
<213> ORGANISM: Artificial Sequence
<220> FEATURE:
<223> OTHER INFORMATION: synthetic antibody peptide construct

<400> SEQUENCE: 116

Asp Ile Gln Leu Thr Gln Ser Pro Ser Ser Leu Ser Ala Ser Val Gly
1               5                   10                  15

Asp Arg Ala Thr Ile Thr Cys Arg Ala Ser Gln Ser Val Ser Thr Ser
            20                  25                  30

Gly Tyr Ser Ser Met His Trp Tyr Gln Gln Lys Pro Gly Lys Ala Pro
        35                  40                  45

Lys Leu Leu Ile Tyr Tyr Ala Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Pro Glu Asp Phe Ala Thr Tyr Tyr Cys His His Ser Trp
                85                  90                  95

Gly Ile Pro Met Tyr Thr Phe Gly Gln Gly Thr Lys Leu Glu Ile Lys
                100                 105                 110

Arg

<210> SEQ ID NO 117
<211> LENGTH: 113
<212> TYPE: PRT
<213> ORGANISM: Artificial Sequence
<220> FEATURE:
<223> OTHER INFORMATION: synthetic antibody peptide construct

<400> SEQUENCE: 117

Asp Ile Gln Leu Thr Gln Ser Pro Ser Ser Leu Ser Ala Ser Val Gly
1               5                   10                  15

Asp Arg Ala Thr Ile Thr Cys Arg Ala Ser Gln Ser Val Ser Thr Ser
            20                  25                  30

Gly Tyr Ser Ser Met His Trp Tyr Gln Gln Lys Pro Gly Lys Ala Pro
        35                  40                  45

Lys Leu Leu Ile Lys Tyr Ala Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Pro Glu Asp Phe Ala Thr Tyr Tyr Cys His His Ser Trp
                85                  90                  95

Gly Ile Pro Met Tyr Thr Phe Gly Gln Gly Thr Lys Leu Glu Ile Lys
                100                 105                 110

Arg

<210> SEQ ID NO 118
<211> LENGTH: 123
<212> TYPE: PRT
<213> ORGANISM: Artificial Sequence
<220> FEATURE:
<223> OTHER INFORMATION: synthetic antibody peptide construct
```

<400> SEQUENCE: 118

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Ile Thr Tyr
            20                  25                  30
Trp Met Asn Trp Val Arg Gln Ala Pro Gly Gln Gly Leu Glu Trp Met
        35                  40                  45
Gly Gln Ile Phe Pro Ala Ser Gly Thr Thr Tyr Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Thr Asp Phe Tyr Arg Tyr Asp Gly Tyr Ala Leu Asp Tyr
            100                 105                 110
Trp Gly Gln Gly Thr Leu Val Thr Val Ser Ser
        115                 120
```

<210> SEQ ID NO 119
<211> LENGTH: 123
<212> TYPE: PRT
<213> ORGANISM: Artificial Sequence
<220> FEATURE:
<223> OTHER INFORMATION: synthetic antibody peptide construct

<400> SEQUENCE: 119

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Ile Thr Tyr
            20                  25                  30
Trp Met Asn Trp Val Arg Gln Ala Pro Gly Gln Gly Leu Glu Trp Val
        35                  40                  45
Gly Gln Ile Phe Pro Ala Ser Gly Thr Thr Tyr Tyr Ala Gln Lys Phe
    50                  55                  60
Gln Gly Arg Val Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Thr Asp Phe Tyr Arg Tyr Asp Gly Tyr Ala Leu Asp Tyr
            100                 105                 110
Trp Gly Gln Gly Thr Leu Val Thr Val Ser Ser
        115                 120
```

<210> SEQ ID NO 120
<211> LENGTH: 123
<212> TYPE: PRT
<213> ORGANISM: Artificial Sequence
<220> FEATURE:
<223> OTHER INFORMATION: synthetic antibody peptide construct

<400> SEQUENCE: 120

```
Gln Val Gln Leu Val Gln Ser Gly Ala Glu Val Lys Lys Pro Gly Ala
1               5                   10                  15
Ser Val Lys Leu Ser Cys Lys Ala Ser Gly Tyr Ile Phe Ile Thr Tyr
            20                  25                  30
Trp Met Asn Trp Val Arg Gln Ala Pro Gly Gln Gly Leu Glu Trp Val
        35                  40                  45
```

```
Gly Gln Ile Phe Pro Ala Ser Gly Thr Thr Tyr Tyr Ala Gln Lys Phe
        50                  55                  60

Gln Gly Arg Ala Thr Leu Thr Val Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Asp Phe Tyr Arg Tyr Asp Gly Gly Tyr Ala Leu Asp Tyr
                100                 105                 110

Trp Gly Gln Gly Thr Leu Leu Thr Val Ser Ser
        115                 120

<210> SEQ ID NO 121
<211> LENGTH: 123
<212> TYPE: PRT
<213> ORGANISM: Artificial Sequence
<220> FEATURE:
<223> OTHER INFORMATION: synthetic antibody peptide construct

<400> SEQUENCE: 121

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
                20                  25                  30

Trp Met Asn Trp Val Arg Gln Ala Pro Gly Gln Gly Leu Glu Trp Val
        35                  40                  45

Gly Gln Ile Phe Pro Ala Ser Gly Thr Thr Tyr Tyr Ala Gln Lys Phe
        50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Asp Phe Tyr Arg Tyr Glu Gly Gly Tyr Ala Leu Asp Tyr
                100                 105                 110

Trp Gly Gln Gly Thr Leu Val Thr Val Ser Ser
        115                 120

<210> SEQ ID NO 122
<211> LENGTH: 108
<212> TYPE: PRT
<213> ORGANISM: Artificial Sequence
<220> FEATURE:
<223> OTHER INFORMATION: synthetic antibody peptide construct

<400> SEQUENCE: 122

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser His Asn Trp Pro His
                85                  90                  95

Thr Phe Gly Gln Gly Thr Lys Leu Glu Ile Lys Arg
```

```
                   100                 105

<210> SEQ ID NO 123
<211> LENGTH: 116
<212> TYPE: PRT
<213> ORGANISM: Artificial Sequence
<220> FEATURE:
<223> OTHER INFORMATION: synthetic antibody peptide construct

<400> SEQUENCE: 123

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Lys Phe
    50                  55                  60

Gln Gly Arg Phe Thr Phe Thr Leu Asp Thr Ser Thr Ser Thr Ala Tyr
65                  70                  75                  80

Leu Glu Ile Arg Ser Leu Arg Ser Asp Asp Thr Ala Val Tyr Tyr Cys
                85                  90                  95

Ala Arg Tyr Tyr Gly Asn Phe Asp Tyr Trp Gly Gln Gly Thr Leu Leu
            100                 105                 110

Thr Val Ser Ser
        115

<210> SEQ ID NO 124
<211> LENGTH: 214
<212> TYPE: PRT
<213> ORGANISM: Artificial Sequence
<220> FEATURE:
<223> OTHER INFORMATION: synthetic antibody peptide construct

<400> SEQUENCE: 124

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser His Asn Trp Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 125
<211> LENGTH: 445
<212> TYPE: PRT
<213> ORGANISM: Artificial Sequence
<220> FEATURE:
<223> OTHER INFORMATION: synthetic antibody peptide construct

<400> SEQUENCE: 125

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Lys Phe
    50                  55                  60

Gln Gly Arg Phe Thr Phe Thr Leu Asp Thr Ser Thr Ser Thr Ala Tyr
65                  70                  75                  80

Leu Glu Ile Arg Ser Leu Arg Ser Asp Asp Thr Ala Val Tyr Tyr Cys
                85                  90                  95

Ala Arg Tyr Tyr Gly Asn Phe Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Cys Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 126
<211> LENGTH: 111
<212> TYPE: PRT
<213> ORGANISM: Artificial Sequence
<220> FEATURE:
<223> OTHER INFORMATION: synthetic antibody peptide construct

<400> SEQUENCE: 126

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 127
<211> LENGTH: 116
<212> TYPE: PRT
<213> ORGANISM: Artificial Sequence
<220> FEATURE:
<223> OTHER INFORMATION: synthetic antibody peptide construct

<400> SEQUENCE: 127

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80
```

Leu Gln Ile Asn Asn Leu Lys Asn Glu Asp Thr Ala Thr Tyr Phe Cys
            85                  90                  95

Ala Arg Tyr Tyr Gly Tyr Phe Asp Tyr Trp Gly Gln Gly Thr Thr Leu
            100                 105                 110

Thr Val Ser Ser
        115

<210> SEQ ID NO 128
<211> LENGTH: 106
<212> TYPE: PRT
<213> ORGANISM: Artificial Sequence
<220> FEATURE:
<223> OTHER INFORMATION: synthetic antibody peptide construct

<400> SEQUENCE: 128

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Ile
            20                  25                  30

His Trp Tyr Arg Gln Lys Pro Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ile Asn Met Glu Ala Glu
65                  70                  75                  80

Asp Ala Ala Thr Tyr Tyr Cys His Gln Arg Thr Tyr Tyr Pro Leu Thr
                85                  90                  95

Phe Gly Gly Gly Thr Arg Leu Glu Leu Lys
            100                 105

<210> SEQ ID NO 129
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 129

Lys Trp Ser Trp Trp Ser Leu Gly Gly Gly Leu Ala Lys Pro Gly Gly
1               5                   10                  15

Ser Leu Lys Leu Ser Cys Thr Ala Ser Gly Phe Thr Phe Thr Ser Tyr
            20                  25                  30

Val Met Ser Trp Val Arg Gln Ser Pro Glu Lys Arg Leu Glu Trp Val
        35                  40                  45

Ala Glu Ile Ser Arg Gly Gly Ser His Thr Tyr Tyr Ser Asp Thr Val
    50                  55                  60

Thr Gly Arg Phe Thr Ile Ser Arg Asp Asn Ala Asn Asn Ala Leu Tyr
65                  70                  75                  80

Leu Glu Met Ser Ser Val Arg Ser Ala Asp Thr Ala Met Tyr Phe Cys
                85                  90                  95

Thr Arg Ala Tyr Gly Asn Ser Glu Met Asp Phe Trp Gly Gln Gly Thr
            100                 105                 110

Ser Val Thr Val Ser Ser
        115

<210> SEQ ID NO 130
<211> LENGTH: 106
<212> TYPE: PRT

<213> ORGANISM: Artificial Sequence
<220> FEATURE:
<223> OTHER INFORMATION: synthetic antibody peptide construct

<400> SEQUENCE: 130

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ile Tyr Ile
            20                  25                  30
Tyr Trp Phe Gln Gln Lys Pro Gly Ser Ser Pro Arg Leu Leu Ile Tyr
        35                  40                  45
Asp Thr Ser Asn Leu Ala Ser Gly Val Pro Leu Arg Phe Ser Gly Ser
    50                  55                  60
Gly Ser Gly Thr Ser Tyr Ser Leu Thr Ile Ser Arg Met Glu Thr Glu
65                  70                  75                  80
Asp Val Ser Thr Tyr Tyr Cys Gln Gln Trp Asn Ser Tyr Pro Pro Thr
                85                  90                  95
Phe Gly Gly Gly Thr Lys Leu Glu Ile Lys
            100                 105
```

<210> SEQ ID NO 131
<211> LENGTH: 118
<212> TYPE: PRT
<213> ORGANISM: Artificial Sequence
<220> FEATURE:
<223> OTHER INFORMATION: synthetic antibody peptide construct

<400> SEQUENCE: 131

```
Glu Val Gln Leu Val Glu Ser Gly Gly Gly Leu Val Lys Pro Gly Gly
1               5                   10                  15
Ser Leu Lys Leu Ser Cys Ala Ala Ser Gly Phe Ser Phe Ser Ser Tyr
            20                  25                  30
Gly Met Ser Trp Val Arg Gln Ser Pro Glu Lys Arg Leu Glu Trp Val
        35                  40                  45
Ala Glu Ile Thr Ser Gly Gly Ser His Thr Tyr Tyr Pro Asp Thr Val
    50                  55                  60
Thr Gly Arg Phe Thr Ile Ser Arg Asp Asn Ala Lys Asn Thr Leu Tyr
65                  70                  75                  80
Leu Glu Met Ser Ser Leu Arg Ser Glu Asp Thr Ala Met Tyr Tyr Cys
                85                  90                  95
Ser Arg Ser Tyr Gly Asn Tyr Val Met Asp Tyr Trp Gly Gln Gly Thr
            100                 105                 110
Ser Val Thr Val Ser Ser
        115
```

<210> SEQ ID NO 132
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 132

```
Gly Tyr Thr Phe Thr Asn Tyr Gly Met His
1               5                   10
```

<210> SEQ ID NO 133
<211> LENGTH: 10
<212> TYPE: PRT
<213> ORGANISM: Artificial Sequence

```
<220> FEATURE:
<223> OTHER INFORMATION: synthetic antibody peptide construct

<400> SEQUENCE: 133

Trp Ile Asn Thr Tyr Thr Gly Glu Pro Thr
1               5                   10

<210> SEQ ID NO 134
<211> LENGTH: 116
<212> TYPE: PRT
<213> ORGANISM: Artificial Sequence
<220> FEATURE:
<223> OTHER INFORMATION: synthetic antibody peptide construct

<400> SEQUENCE: 134

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ser Pro Gly Gly Leu Lys Trp Met
        35                  40                  45

Gly Trp Ile Asn Thr Tyr Thr Gly Glu Pro Thr Tyr Ala Asp Asp Phe
50                  55                  60

Lys Gly Arg Phe Gly Phe Ser Leu Glu Thr Ser Ala Ser Ser Ala Tyr
65                  70                  75                  80

Leu Gln Ile Asn Asp Leu Lys Asn Glu Asp Met Ala Thr Tyr Phe Cys
                85                  90                  95

Ala Arg Tyr Tyr Gly Asn Phe Asp Tyr Trp Gly Gln Gly Thr Thr Leu
            100                 105                 110

Thr Val Ser Ser
        115

<210> SEQ ID NO 135
<211> LENGTH: 6
<212> TYPE: PRT
<213> ORGANISM: Artificial Sequence
<220> FEATURE:
<223> OTHER INFORMATION: synthetic antibody peptide construct

<400> SEQUENCE: 135

Val Pro Ala Pro Arg Tyr
1               5

<210> SEQ ID NO 136
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 136

Ile Ser His Ser Arg Thr Glu Asp Glu Thr
1               5                   10

<210> SEQ ID NO 137
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 137

Gly Leu Ser Tyr Ser Ser Leu Lys Asn Val
```

```
<210> SEQ ID NO 138
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 138

Ala Ser Ser Lys Ile His Ser Gly Thr Gly
1               5                   10

<210> SEQ ID NO 139
<211> LENGTH: 10
<212> TYPE: PRT
<213> ORGANISM: Artificial Sequence
<220> FEATURE:
<223> OTHER INFORMATION: synthetic antibody peptide construct

<400> SEQUENCE: 139

Pro Ile Leu Pro Gly Ser Phe Trp Asn Arg
1               5                   10
```